(12) United States Patent
Grandi et al.

(10) Patent No.: US 9,764,027 B2
(45) Date of Patent: Sep. 19, 2017

(54) OUTER MEMBRANE VESICLES

(71) Applicant: GlaxoSmithKline Biologicals SA, Rixensart (BE)

(72) Inventors: Guido Grandi, Segrate (IT); Immaculada Margarit Y Ros, Siena (IT); Emiliano Chiarot, Monteriggioni (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/424,839

(22) PCT Filed: Sep. 18, 2013

(86) PCT No.: PCT/EP2013/069415
§ 371 (c)(1),
(2) Date: Feb. 27, 2015

(87) PCT Pub. No.: WO2014/044728
PCT Pub. Date: Mar. 27, 2014

(65) Prior Publication Data
US 2015/0231232 A1  Aug. 20, 2015

Related U.S. Application Data

(60) Provisional application No. 61/702,296, filed on Sep. 18, 2012, provisional application No. 61/799,311, filed on Mar. 15, 2013.

(51) Int. Cl.
*A61K 39/39*  (2006.01)
*A61K 39/00*  (2006.01)

(52) U.S. Cl.
CPC .... *A61K 39/39* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 5,916,588 | A | 6/1999 | Popescu et al. |
| 6,080,725 | A | 6/2000 | Marciani |
| 6,090,406 | A | 7/2000 | Popescu et al. |
| 6,180,111 | B1 | 1/2001 | Stein et al. |
| 6,207,646 | B1 | 3/2001 | Krieg et al. |
| 6,239,116 | B1 | 5/2001 | Krieg et al. |
| 6,355,253 | B1 | 3/2002 | Zlotnick |
| 6,429,199 | B1 | 8/2002 | Krieg et al. |
| 6,451,317 | B1 | 9/2002 | Blake et al. |
| 6,936,261 | B2 | 8/2005 | Granoff et al. |
| 7,018,636 | B1 | 3/2006 | Bhattacharjee et al. |
| 7,384,645 | B2 | 6/2008 | Foster et al. |
| 7,628,995 | B2 | 12/2009 | Bos et al. |
| 7,754,218 | B2 | 7/2010 | Contorni et al. |
| 7,838,014 | B2 | 11/2010 | Biemans et al. |
| 8,007,815 | B1 | 8/2011 | Granoff et al. |
| 8,029,807 | B2 | 10/2011 | Bos et al. |
| 8,663,656 | B2 | 3/2014 | Pizza |
| 8,808,711 | B2 | 8/2014 | Oster et al. |
| RE45,137 | E | 9/2014 | O'Hagan et al. |
| 8,968,748 | B2 | 3/2015 | Granoff et al. |
| 2006/0029621 | A1 | 2/2006 | Granoff et al. |
| 2006/0240045 | A1 | 10/2006 | Berthet et al. |
| 2007/0014805 | A1 | 1/2007 | Klucker et al. |
| 2007/0059329 | A1 | 3/2007 | Norals et al. |
| 2011/0182942 | A1 | 7/2011 | Zollinger |
| 2011/0262484 | A1 | 10/2011 | Feavers |

FOREIGN PATENT DOCUMENTS

| | | |
|---|---|---|
| EP | 0011243 B1 | 4/1982 |
| EP | 0109942 A2 | 5/1984 |
| EP | 0109942 B1 | 3/1991 |
| EP | 0626169 A2 | 11/1994 |
| EP | 0689454 A1 | 1/1996 |
| EP | 0735898 A1 | 10/1996 |
| EP | 0761231 A1 | 3/1997 |
| EP | 0689454 B1 | 9/1997 |
| EP | 0835318 A2 | 4/1998 |
| EP | 0735898 B1 | 3/1999 |
| EP | 0626169 B1 | 7/1999 |
| EP | 0761231 B1 | 1/2000 |
| EP | 1741443 A2 | 1/2007 |
| WO | WO-90/14837 A1 | 12/1990 |

(Continued)

OTHER PUBLICATIONS

Muralinath et al. (Infect. Immun., 79:887-894, 2011).*
Yother et al., J. Bacteriol., 174:601-609, 1992.*
Kang et al., Infect. Immun., 70:1739-1749, 2002.*
"VA-MENGOC-BC," Product information from S.C.S. Farmacia Manes, Argentina. Cited in International Search Report dated Aug. 23, 2000 for PCT/US99/11977. 1 page.
Arigita, C. at al. "Stability of mono- and trivalent meningococcal outer membrane vesicle vaccines," Vaccine, vol. 22, No. 5-0, 2004, pp. 630-643.
Artenstein, M.S. (1975). "Control of Meningococcal Meningitis with Meningococcal Vaccines." Yale J. Biol. Med. 48(3):197-200.
Beveridge, (1999) "Structures of gram-negative cell walls and their derived membrane vesicles." J. Bacteriol. 181(16):4725-4733.
Bjune et al., "Effect of outer membrane vesicle vaccine against group B meningococcal disease in Norway," Lancet 338(8775):1093-1096,1991.
Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.

(Continued)

*Primary Examiner* — Brian J Gangle

(57) ABSTRACT

The present invention provides an outer membrane vesicle (OMV) from a Gram-negative bacterium, comprising at least one heterologous protein that is free in the lumen of the OMV, wherein the OMV is capable of eliciting an immune response to the heterologous protein when administered to a mammal. The invention also provides methods for preparing the OMVs of the invention, pharmaceutical compositions comprising the OMVs of the invention, especially immunogenic compositions and vaccines, and methods of generating an antibody immune response in a mammal using OMVs.

16 Claims, 19 Drawing Sheets

(56) References Cited

FOREIGN PATENT DOCUMENTS

| | | |
|---|---|---|
| WO | WO-94/00153 A1 | 1/1994 |
| WO | WO-95/11700 A1 | 5/1995 |
| WO | WO-95/17211 A1 | 6/1995 |
| WO | WO-96/11711 A1 | 4/1996 |
| WO | WO-96/33739 A1 | 10/1996 |
| WO | WO-98/40100 A1 | 9/1998 |
| WO | WO-98/42375 A1 | 10/1998 |
| WO | WO-98/57659 A1 | 12/1998 |
| WO | WO-99/27960 A1 | 6/1999 |
| WO | WO-99/40936 A2 | 8/1999 |
| WO | WO-99/44636 A2 | 9/1999 |
| WO | WO-99/61053 A1 | 12/1999 |
| WO | WO-99/62923 A2 | 12/1999 |
| WO | WO-00/07621 A2 | 2/2000 |
| WO | WO-01/34642 A2 | 5/2001 |
| WO | WO-01/91788 A1 | 12/2001 |
| WO | WO-01/95935 A1 | 12/2001 |
| WO | WO-02/02606 A2 | 1/2002 |
| WO | WO-02/09643 A2 | 2/2002 |
| WO | WO-02/26757 A2 | 4/2002 |
| WO | WO-02/34771 A2 | 5/2002 |
| WO | WO-03/018054 A1 | 3/2003 |
| WO | WO-03/035836 A2 | 5/2003 |
| WO | WO-2004/019977 A2 | 3/2004 |
| WO | WO-2004/054611 A1 | 7/2004 |
| WO | WO-2004/084938 A1 | 10/2004 |
| WO | WO-2005/002619 A2 | 1/2005 |
| WO | WO-2005/004908 A1 | 1/2005 |
| WO | WO-2005/032582 A2 | 4/2005 |
| WO | WO-2005/064021 A2 | 7/2005 |
| WO | WO-2005/097181 A1 | 10/2005 |
| WO | WO-2005/111066 A2 | 11/2005 |
| WO | WO-2006/046143 A2 | 5/2006 |
| WO | WO-2006/089264 A2 | 8/2006 |
| WO | WO-2006/091517 A2 | 8/2006 |
| WO | WO-2006/110413 A2 | 10/2006 |
| WO | WO-2006/110603 A1 | 10/2006 |
| WO | WO-2006/113373 A2 | 10/2006 |
| WO | WO-2006/138004 A2 | 12/2006 |
| WO | WO-2007/049155 A2 | 5/2007 |
| WO | WO-2008/020330 A2 | 2/2008 |
| WO | WO-2009/016515 A2 | 2/2009 |
| WO | WO-2009/031043 A2 | 3/2009 |
| WO | WO-2009/104092 A2 | 8/2009 |
| WO | WO-2009/109860 A2 | 9/2009 |
| WO | WO-2009/158142 A1 | 12/2009 |
| WO | WO-2010/010983 A1 | 1/2010 |
| WO | WO-2010/119343 A2 | 10/2010 |
| WO | WO-2011/036562 A1 | 3/2011 |

OTHER PUBLICATIONS

CECMED (Dec. 2, 2011), "Resumen de las Caracteristicas del Producto: VA-MENGOC-BC," Ministerio de Salud Publica de Cuba, 4 pages. (3 page English translation included).

Chen, D J et al. (2010), "Delivery of foreign antigens by engineered outer membrane vesicle vaccines." PNAS 107(7):3099-3104.

Collins (2011). "Gram-negative outer membrane vesicles in vaccine development," Discov Med, 12(62):7-15.

Corbel, "Control testing of combined vaccines: a consideration of potential problems and approaches," *Biologicals* 22(4):353-360, 1994.

Dalseg et al. (May 14, 1999). "Outer membrane vesicles from group B meningococci are strongly immunogenic when given intranasally to mice" Vaccine 17(19):2336-2345.

De Kleijn, ED. et al. "Immunogenicity and safety of a hexavalent meningococcal outer membrane-vesicle vaccine in children of 2-3 and 7-8 years of age," Vaccine, 18:1456-1466(2000).

de Moraes JC, et al. (1992). Protective efficacy of a serogroup B meningococcal vaccine in Sao Paulo, Brazil. Lancet 340: 1074-1078.

Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).

Debbag et al., "Evaluation of Adverse Reactions Associated to Antimeningococcal BC Vaccination in 16,700 Children" Clinical Infectious Diseases, vol. 21, pp. 790-A420 (Sep. 1995).

Decision revoking EP1534326, filed in Opposition against EP1534326, dated Jan. 15, 2016, 3 pages.

Decision revoking EP1644035, filed in Opposition against EP1644035, dated Jan. 20, 2014, 14 pages.

Declaration from Christiane Feron, filed in opposition against EP1534326, dated Sep. 28, 2009, 3 pages.

Devoe et al. (1973). "Release of endotoxin in the form of cell wall blebs during in vitro growth of Neisseria meningitidis," J Exp Med, 138(5):1156-67.

Ellis et al. (2010). "Virulence and immunomodulatory roles of bacterial outer membrane vesicles," Microbiol Mol Biol Rev, 74(1):81-94.

Experimental data regarding OMV expression following OMV extraction, filed in opposition against EP1534326, dated Oct. 2, 2009, 1 page.

Experimental data: expression of NspA, fHBP and GNA2132 in N. meningitidis, filed in opposition against EP1534326, dated Aug. 4, 2010. 2 pages.

Ferrari et al. (2006). "Outer membrane vesicles from group B Neisseria meningitidis delta gna33 mutant: proteomic and immunological comparison with detergent-derived outer membrane vesicles," Proteomics, 6(6):1856-66.

Findlay, et al. (2005). "Surface expression, single-channel analysis and membrane topology of recombinant Chlamydia trachomatis Major Outer Membrane Protein." BMC Microbiology, 5:5.

Frasch et al. (2001). "Outer Membrane Protein Vesicle Vaccines for Meningococcal Disease," Chapter 7 in "Methods in Molecular Medicine, Meningococcal Vaccines: Methods and Protocols," Pollard et al. (Ed), Humana Press, Totowa, New Jersey, vol. 66, pp. 81-107.

Fredrikson et al. (1991). Production, characterization and control of MenB-vaccine "Folkehelsa": an outer membrane vesicle vaccine against group B meningococcal disease. NIPH Annals 14:67-79.

Fukasawa et al. (1999) "Neisseria meningitidis serogroup C polysaccharide and serogroup B outer membrane vesicle conjugate as a bivalent meningococcus vaccine candidate." Vaccine 17:2951-2958.

Fukasawa et al. (2004). "Adjuvant can improve protection induced by OMV vaccine against Neisseria meningitidis serogroups B/C in neonatal mice" FEMS Immunol. Med. Microbiol. 41:205-210.

Galeano et al. (1995). "Efectividad de una vacuna antimeningococcica en una cohorte de itagui, Colombia, 1995," Epidemiologico de Antioquia 20(2), 8 pages. (9 page English translation included).

Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).

Gil et al. (2009). "Proteomic study via a non-gel based approach of meningococcal outer membrane vesicle vaccine obtained from strain CU385," Human Vaccines 5(5):347-356.

Henry, et al.(2004). "Improved methods for producing outer membrane vesicles in Gram-negative bacteria," Research in Microbiology, 155:437-446.

Hoiby et al. (1991). "Bactericidal antibodies after vaccination with the Norwegian meningococcal serogroup B outer membrane vesicle vaccine: a brief survey," NIPH Annals 14(2):147-155.

Hoiby et al. (1991). "The Norwegian meningococcal serogroup B outer membrane vesicle vaccine protection trials: case tracing, meningococcal antigen detection and serological diagnosis," NIPH Annals, 14(2):107-123.

Holst et al. (2003). "Serum bactericidal activity correlates with the vaccine efficacy of outer membrane vesicle vaccines against Neisseria meningitidis serogroup B disease," Vaccine 21(7-8):734-737.

Holst et al. (2009). "Properties and clinical performance of vaccines containing outer membrane vesicles from Neisseria meningitidis," Vaccine; 27 Suppl 2:B3-12.

Interlocutory decision in opposition proceedings, filed in opposition against EP1534326, dated Mar. 25, 2010, 11 pages.

(56) References Cited

OTHER PUBLICATIONS

International Preliminary Examination Report mailed Aug. 23, 2000, for international patent application No. PCT/US99/11977, filed May 28, 1999, 7 pages.
Katial et al. (2002). "Immunogenicity and Safety Testing of a Group B Intranasal Meningococcal Native Outer Membrane Vesicle Vaccine," Infection and Immunity 70(2):702-707.
Ketsy, et al. (2004). "Incorporation of heterologous outer membrane and periplasmic proteins into *Escherichia coli* outer membrane vesicles." J Biol Chem, 279(3):2069-2076.
Koeberling et al. (2007). "Improved immunogenicity of a H44/76 group B outer membrane vesicle vaccine with over-expressed genome-derived Neisserial antigen 1870," Vaccine 25(10):1912-1920.
List of Journals from SpringerProtocols website about Methods in Molecular Biology, filed in Opposition against EP1644035, dated Oct. 18, 2014, 5 pages.
McLeod et al. (2000). "Structural relationships and sialylation among meningococcal L1, L8, and L3,7 lipooligosaccharide serotypes," J Biol Chem, 275(13):9716-24.
Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.
Norheim et al. (2004). "Immunogenicity and bactericidal activity in mice of an outer membrane protein vesicle vaccine against Neisseria meningitidis serogroup A disease," Vaccine, 22: 2171-2180.
Norheim et al. (2005). "Development and characterisation of outer membrane vesicle vaccines against serogroup A Neisseria meningitidis" Vaccine 23(29):3762-3774.
Notice of Appeal by Carpmaels & Ransford, filed in Opposition against EP1644035, dated Mar. 24, 2014, 1 page.
Notice of Appeal by GlaxoSmithKline Biologicals S.A., filed in relation to EP1534326, dated Jun. 3, 2010, 2 pages.
Notice of opposition by GlaxoSmithKline Biologicals S.A., filed in opposition against EP1534326, dated Mar. 3, 2008, 19 pages.
Notice of Opposition, filed in Opposition against EP1644035, dated May 24, 2012, 15 pages.
O'Hallahan J, et al. 2004. The strategy to control New Zealand's epidemic of Group B meningococcal disease. PIDJ 23: S293-S298.
Ochoa, Rolando (2008). "Main projects on research, development and manufacturing of human vaccines," excerpt from presentation at BioQatar Symposium 2008, 4 slides.
Oster et al. (2007). "Immunogenicity and safety of a strain-specific MenB OMV vaccine delivered to under 5-year olds in New Zealand," Vaccine, 25:3075-9.
Parkhill et al. (2000). "Complete DNA Sequence of a Serogroup A Strain of Neisseria meningitides Z2491," Nature, 404(6777):502-506.
Patentee's response to Notice of Opposition, filed in Opposition against EP1644035, dated Mar. 12, 2013, 9 pages.
Patentee's response to opposition, filed in opposition against EP1534326, dated Jan. 19, 2009, 11 pages.
Peeters et al. (1996). "Phase I clinical trial with a hexavalent PorA containing meningococcal outer membrane vesicle vaccine," Vaccine 14(10):1009-1015.
Perez et al. (2010). "Community acquired bacterial meningitis in Cuba: a follow up of a decade," BMC Infectious Diseases 10:130, 9 pages.
Perkins et al. (1998). "Immunogenicity of two efficacious outer membrane protein-based serogroup B meningococcal vaccines among young adults in Iceland," *The Journal of Infectious Disease* 177:683-691.
Poolman et al. (1986). "Class 1/3 outer membrane protein vaccine against group B, type 15, subtype 16 meningococci." Dev. Biol. Stand. Abstract only. 63:147-52.
Reply to Statement of Grounds of Appeal by Nederlandsch Octrooibureau, filed in Opposition against EP1644035, dated Oct. 15, 2014, 8 pages.
Rodriguez et al. (1999). "The epidemiological impact of antimeningococcal B vaccination in Cuba," Mem Inst Oswaldo Cruz 94(4):433-440.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Rosenqvist et al., "Effect of Aluminum Hydroxide and Meningococcal Serogroup C Capsular Polysaccharide on the Immunogenicity and Reactogenicity of a Group B Neisseria meningitidis Outer Membrane Vesicle Vaccine", Developments in Biological Standardization, vol. 92, pp. 323-333, (1998).
Sacchi et al. (2001). "Serosubtypes and PorA types of Neisseria meningitidis serogroup B isolated in Brazil during 1997--1998: overview and implications for vaccine development," J Clin Microbiol, 39(8):2897-903.
Sierra GV, et al. (1991). Vaccine against group B Neisseria meningitidis: protection trial and mass vaccination results in Cuba. NIPH Ann 14: 195-207.
Slide printout by Carpmaels & Ransford, filed in opposition against EP1534326, dated Nov. 23, 2009, 2 pages.
Statement of Grounds of Appeal by Carpmaels & Ransford, filed in Opposition against EP1644035, dated May 30, 2014, 5 pages.
Statement of Grounds of Appeal by GlaxoSmithKline Biologicals S.A., filed in relation to EP1534326, dated Aug. 4, 2010, 24 pages.
Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.
van de Waterbeemd (2012). "Identification and optimization of critical process parameters for the production of NOMV vaccine against Neisseria meningitidis," Vaccine, 30(24):3683-90.
Van der Ley & Steeghs (2003) "Lessons from an LPS-deficient Neisseria meningitidis mutant" Journal of Endotoxin Research 9(2):124-128.
Van der Ley et al. (1992). "Construction of a Multivalent Meningococcal Vaccine Strain Based on the Class I Outer Membrane Protein," *Infection and Immunity* 60(8): 3516-3161.
Verheul et al. (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
Vermont et al. (2003). "Meningococcal serogroup B infections: a search for a broadly protective vaccine," Expert Rev Vaccines, 2(5):673-81.
Wedege et al. (2003). "Antibody specificities and effect of meningococcal carriage in Icelandic teenagers receiving the Norwegian serogroup B outer membrane vesicle vaccine," Infect. Immun. 71:3775-3781.
Williams et al., (2007) "Proteomic analysis of outer membranes and vesicles from wild-type serogroup B Neisseria meningitidis and a lipopolysaccharide-deficient mutant" Infection and Immunity 75(3):1364-1372.
Wilson & Walker (Eds.) (1994). "Wilson Principles and techniques of practical biochemistry: Editors: Bryan L. Williams and Keith Wilson," Cambridge University Press, Cambridge, fourth edition, p. 309.
Written submission in preparation to oral proceedings by Carpmaels & Ransford, filed in Opposition against EP1644035, dated Oct. 18, 2013, 2 pages.
Written submission in preparation to oral proceedings by GlaxoSmithKline Biologicals S.A., filed in opposition against EP1534326, dated Sep. 30, 2009, 24 pages.
Written submission in preparation to oral proceedings by Nederlandsch Octrooibureau, filed in Opposition against EP1644035, dated Oct. 18, 2013, 6 pages.
Zollinger et al. (2010). "Design and evaluation in mice of a broadly protective meningococcal group B native outer membrane vesicle vaccine," Vaccine, 28(31):5057-5067.

(56) References Cited

OTHER PUBLICATIONS

Chiarot et al. (2013) "Targeted Amino Acid Substitutions Impair Streptolysin O Toxicity and Group A Streptococcus Virulence," mBio, 4(1):1-9.

* cited by examiner

SEQUENCE LISTING

<160> NUMBER OF SEQ ID NOS: 75

<210> SEQ ID NO 1
<211> LENGTH: 63
<212> TYPE: DNA
<213> ORGANISM: Artificial Sequence
<220> FEATURE:
<223> OTHER INFORMATION: OmpA signal sequence

<400> SEQUENCE: 1
atgaaaaaga cagctatcgc gattgcagtg gcactggctg gtttcgctac cgtagcgcag    60
gcc                                                                  63

<210> SEQ ID NO 2
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: n
<222> LOCATION: 1, 3, 5, 7, 9, 11, 13, 15, 17, 19, 21, 23, 25
<223> OTHER INFORMATION: inosine

<400> SEQUENCE: 2
ncncncncnc ncncncncnc ncncnc                                         26

<210> SEQ ID NO 3
<211> LENGTH: 11
<212> TYPE: PRT
<213> ORGANISM: Artificial Sequence
<220> FEATURE:
<223> OTHER INFORMATION: polycationic polymer

<400> SEQUENCE: 3

Lys Leu Lys Leu Leu Leu Leu Leu Lys Leu Lys
1               5                   10

<210> SEQ ID NO 4
<211> LENGTH: 40
<212> TYPE: DNA
<213> ORGANISM: Artificial Sequence
<220> FEATURE:
<223> OTHER INFORMATION: Oligonucleotide primer GAS25-F

<400> SEQUENCE: 4
accgtagcgc aggccaacaa acaaaacact gctagtacag                          40

<210> SEQ ID NO 5
<211> LENGTH: 41
<212> TYPE: DNA
<213> ORGANISM: Artificial Sequence
<220> FEATURE:
<223> OTHER INFORMATION: Oligonucleotide primer GAS25-R

<400> SEQUENCE: 5
gtgatggtga tgttactact tataagtaat cgaaccatat g                        41

<210> SEQ ID NO 6
<211> LENGTH: 47
<212> TYPE: DNA
<213> ORGANISM: Artificial Sequence
<220> FEATURE:
<223> OTHER INFORMATION: Oligonucleotide primer SpyCEP-F3

<400> SEQUENCE: 6

-continued accgtagcgc aggccgcagc agatgagcta agcacaatga gcgaacc        47

<210> SEQ ID NO 7
<211> LENGTH: 54
<212> TYPE: DNA
<213> ORGANISM: Artificial Sequence
<220> FEATURE:
<223> OTHER INFORMATION: Oligonucleotide primer SpyCEP-R3

<400> SEQUENCE: 7
gtgatggtga tgttattagg cttttgctgt tgctgaggtc gttgacttgg ttgg        54

<210> SEQ ID NO 8
<211> LENGTH: 39
<212> TYPE: DNA
<213> ORGANISM: Artificial Sequence
<220> FEATURE:
<223> OTHER INFORMATION: Oligonucleotide primer Bla-omp-F

<400> SEQUENCE: 8
accgtagcgc aggcccggta agatccttga gatttttcg        39

<210> SEQ ID NO 9
<211> LENGTH: 39
<212> TYPE: DNA
<213> ORGANISM: Artificial Sequence
<220> FEATURE:
<223> OTHER INFORMATION: Oligonucleotide primer Bla-omp-R

<400> SEQUENCE: 9
gtgatggtga tgttattacc aatgcttaat cagtgaggc        39

<210> SEQ ID NO 10
<211> LENGTH: 31
<212> TYPE: DNA
<213> ORGANISM: Artificial Sequence
<220> FEATURE:
<223> OTHER INFORMATION: Oligonucleotide primer fHbp-F

<400> SEQUENCE: 10
accgtagcgc aggccgtcgc cgccgacatc g        31

<210> SEQ ID NO 11
<211> LENGTH: 35
<212> TYPE: DNA
<213> ORGANISM: Artificial Sequence
<220> FEATURE:
<223> OTHER INFORMATION: Oligonucleotide primer fHbp-R

<400> SEQUENCE: 11
gtgatggtga tgttattatt gcttggcggc aaggc        35

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer omprev

<400> SEQUENCE: 12
ggcctgcgct acggtagcga aa        22

<210> SEQ ID NO 13
<211> LENGTH: 32
<212> TYPE: DNA
<213> ORGANISM: Artificial Sequence

```
<220> FEATURE:
<223> OTHER INFORMATION: Oligonucleotide primer nohisflag

<400> SEQUENCE: 13
taacatcacc atcaccatca cgattacaaa ga                           32

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer tolR-1

<400> SEQUENCE: 14
tctggaatcg aactctctcg                                         20

<210> SEQ ID NO 15
<211> LENGTH: 42
<212> TYPE: DNA
<213> ORGANISM: Artificial Sequence
<220> FEATURE:
<223> OTHER INFORMATION: Oligonucleotide primer tolR-2

<400> SEQUENCE: 15
attttgagac acaacgtggc tttcatggct taccccttgt tg                42

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide primer tolR-3

<400> SEQUENCE: 16
ttcacgaggc agacctcata aacatctgcg tttcccttg                    39

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer tolR-4

<400> SEQUENCE: 17
ttgcttctgc tttaactcgg                                         20

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide primer ompA-1

<400> SEQUENCE: 18
gatcggttgg ttggcagat                                          19

<210> SEQ ID NO 19
<211> LENGTH: 43
<212> TYPE: DNA
<213> ORGANISM: Artificial Sequence
<220> FEATURE:
<223> OTHER INFORMATION: Oligonucleotide primer ompA-2

<400> SEQUENCE: 19
caccaggatt tatttattct gcgttttgc gcctcgttat cat                43
```

<210> SEQ ID NO 20
<211> LENGTH: 39
<212> TYPE: DNA
<213> ORGANISM: Artificial Sequence
<220> FEATURE:
<223> OTHER INFORMATION: Oligonucleotide primer ompA-3

<400> SEQUENCE: 20
tactgcgatg agtggcaggc gcaggcttaa gttctcgtc                    39

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer ompA-4

<400> SEQUENCE: 21
aaaatcttga aagcggttgg                                         20

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide primer PUC4K-rev

<400> SEQUENCE: 22
aaagccacgt tgtgtctc                                           18

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide primer PUC4K-for

<400> SEQUENCE: 23
tgaggtctgc ctcgtgaa                                           18

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer CMR-for

<400> SEQUENCE: 24
cgcagaataa ataaatcctg gtg                                     23

<210> SEQ ID NO 25
<211> LENGTH: 19
<212> TYPE: DNA
<213> ORGANISM: Artificial Sequence
<220> FEATURE:
<223> OTHER INFORMATION: Oligonucleotide primer CMR-rev

<400> SEQUENCE: 25
cctgccactc atcgcagta                                          19

<210> SEQ ID NO 26
<211> LENGTH: 39
<212> TYPE: DNA
<213> ORGANISM: Artificial Sequence
<220> FEATURE:
<223> OTHER INFORMATION: Oligonucleotide primer Spy0269-F

<400> SEQUENCE: 26
accgtagcgc aggccgatga tagagcctca ggagaaacg                                 39

<210> SEQ ID NO 27
<211> LENGTH: 38
<212> TYPE: DNA
<213> ORGANISM: Artificial Sequence
<220> FEATURE:
<223> OTHER INFORMATION: Oligonucleotide primer Spy0269-R

<400> SEQUENCE: 27
gtgatggtga tgttatcact tagattcctt acggaacc                                  38

<210> SEQ ID NO 28
<211> LENGTH: 46
<212> TYPE: DNA
<213> ORGANISM: Artificial Sequence
<220> FEATURE:
<223> OTHER INFORMATION: Oligonucleotide primer Spy0269-fus3

<400> SEQUENCE: 28
gattacttat aagtagagaa ggagatatac atatgaaaaa gacagc                         46

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer Slo-fus-F

<400> SEQUENCE: 29
aacaaacaaa acactgctag tacag                                                25

<210> SEQ ID NO 30
<211> LENGTH: 38
<212> TYPE: DNA
<213> ORGANISM: Artificial Sequence
<220> FEATURE:
<223> OTHER INFORMATION: Oligonucleotide primer Slo-fus-R3

<400> SEQUENCE: 30
tatactcctt ctctacttat aagtaatcga accatatg                                  38

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer Spy0269-fus-R

<400> SEQUENCE: 31
tcacttagat tccttacgga acc                                                  23

<210> SEQ ID NO 32
<211> LENGTH: 44
<212> TYPE: DNA
<213> ORGANISM: Artificial Sequence
<220> FEATURE:
<223> OTHER INFORMATION: Oligonucleotide primer Spycep-fus-F

<400> SEQUENCE: 32
aaggaatcta agtgagaagg agatatacat atgaaaaaga cagc                           44

<210> SEQ ID NO 33

<211> LENGTH: 1768
<212> TYPE: DNA
<213> ORGANISM: Artificial Sequence
<220> FEATURE:
<223> OTHER INFORMATION: vector sequence pET-21_slo-dm

<400> SEQUENCE: 33

```
taatacgact cactataggg gaattgtgag cggataacaa ttcccctcta gaaataattt      60
tgtttaactt taagaaggag atatacatat gaaaaagaca gctatcgcga ttgcagtggc     120
actggctggt ttcgctaccg tagcgcaggc caacaaacaa aacactgcta gtacagaaac     180
cacaacgaca aatgagcaac caaagccaga agtagtgagc taactactg aaaaagcagg      240
tcagaaaacg gatgatatgc ttaactctaa cgatatgatt aagcttgctc ccaaagaaat     300
gccactagaa tctgcagaaa agaagaaaa aaagtcagaa gacaaaaaaa agagcgaaga     360
agatcacact gaagaaatca atgacaagat ttattcacta aattataatg agcttgaagt     420
acttgctaaa aatggtgaaa ccattgaaaa ttttgttcct aaagaaggcg ttaagaaagc     480
tgataaattt attgtcattg aaagaaagaa aaaaatatc aacactacac cagtcgatat      540
ttccattatt gactctgtca ctgataggac ctatccagca gcccttcagc tggctaataa     600
aggttttacc gaaacaaac cagacgcggt agtcaccaag cgaaacccac aaaaaatcca     660
tattgattta ccaggtatgg gagacaaagc aacggttgag gtcaatgacc ctacctatgc     720
caatgtttca acagctattg ataatcttgt taaccaatgg catgataatt attctggtgg     780
taatacgctt cctgccagaa cacaatatac tgaatcaatg gtatattcta agtcacagat     840
tgaggcagct ctaaatgtta atagcaaaat cttagatggt actttaggca ttgatttcaa     900
gtcgatttca aaaggtgaaa agaaggtgat gattgcagca tacaagcaaa ttttttacac     960
cgtatcagca aaccttccta ataatcctgc ggatgtgttt gataaatcgg tgacctttaa    1020
agagttgcaa cgaaaaggtg tcagcaatga agctccgcca ctctttgtga gtaacgtagc    1080
ctatggtcga actgttttttg tcaaactaga acaagttct aaaagtaatg atgttgaagc    1140
ggcctttagt gcagctctaa aaggaacaga tgttaaaact aatggaaaat attctgatat    1200
cttagaaaat agctcattta cagctgtcgt tttaggagga gatgctgcag agcacaataa    1260
ggtagtcaca aaagactttg atgttattag aaacgttatc aaagacaatg ctaccttcag    1320
tagaaaaaac ctagcttatc ctatttcata caccagtgtt ttccttaaaa ataataaaat    1380
tgcgggtgtc aataacagaa ctgaatacgt tgaaacaaca tctaccgagt acactagtgg    1440
aaaaattaac ctgtctctatc aaggcgcgta tgttgctcaa tatgaaatcc tttgggatga    1500
aatcaattat gatgacaaag gaaaagaagt gattacaaaa cgacgttggg acaacaactg    1560
gtatagtaag acatcaccat ttagcacagt tatcccacta ggagctaatt cacgaaatat    1620
ccgtatcatg gctagagagt gcactggctt agctttcgaa tggtggcgaa aagtgatcga    1680
cgaaagagat gtgaaactgt ctaaagaaat caatgtcaat atctcaggat caaccttgag    1740
cccatatggt tcgattactt ataagtag                                        1768
```

<210> SEQ ID NO 34
<211> LENGTH: 4898
<212> TYPE: DNA
<213> ORGANISM: Artificial Sequence
<220> FEATURE:
<223> OTHER INFORMATION: vector sequence pET-21_spycep

<400> SEQUENCE: 34

```
taatacgact cactataggg gaattgtgag cggataacaa ttcccctcta gaaataattt      60
```

```
tgtttaactt taagaaggag atatacatat gaaaaagaca gctatcgcga ttgcagtggc    120
actggctggt ttcgctaccg tagcgcaggc cgcagcagat gagctaagca caatgagcga    180
accaacaatc acgaatcacg ctcaacaaca agcgcaacat ctcaccaata cagagttgag    240
ctcagctgaa tcaaaatctc aagacacatc acaaatcact ctcaagacaa atcgtgaaaa    300
agagcaatca caagatctag tctctgagcc aaccacaact gagctagctg acacagatgc    360
agcatcaatg gctaatacag gttctgatgc gactcaaaaa agcgcttctt taccgccagt    420
caatacagat gttcacgatt gggtaaaaac caaggagct gggacaagg gatacaaagg      480 acaaggcaag gttgtcgcag ttattgacac agggatcgat ccggcccatc aaagcatgcg    540
catcagtgat gtatcaactg ctaaagtaaa atcaaaagaa gacatgctag cacgccaaaa    600
agccgccggt attaattatg ggagttggat aaatgataaa gttgttttg cacataatta     660 tgtggaaaat agcgataata tcaaagaaaa tcaattcgag gattttgatg aggactggga    720
aaactttgag tttgatgcag aggcagagcc aaaagccatc aaaaaacaca agatctatcg    780
tccccaatca acccaggcac cgaaagaaac tgttatcaaa acagaagaaa cagatggttc    840
acatgatatt gactggacac aaacagacga tgacaccaaa tacgagtcac acggtatgca    900
tgtgacaggt attgtagccg gtaatagcaa agaagccgct gctactggag aacgcttttt    960
aggaattgca ccagaggccc aagtcatgtt catgcgtgtt tttgccaacg acatcatggg   1020
atcagctgaa tcactcttta tcaaagctat cgaagatgcc gtggctttag gagcagatgt   1080
gatcaacctg agtcttggaa ccgctaatgg ggcacagctt agtggcagca agcctctaat   1140
ggaagcaatt gaaaaagcta aaaaagccgg tgtatcagtt gttgtagcag caggaaatga   1200
gcgcgtctat ggatctgacc atgatgatcc attggcgaca aatccagact atggtttggt   1260
cggttctccc tcaacaggtc gaacaccaac atcagtggca gctataaaca gtaagtgggt   1320
gattcaacgt ctaatgacgg tcaaagaatt agaaaaccgt gccgatttaa accatggtaa   1380
agccatctat tcagagtctg tcgactttaa agacataaaa gatagcctag ttatgataa    1440 atcgcatcaa tttgcttatg tcaaagagtc aactgatgcg ggttataacg cacaagacgt   1500
taaaggtaaa attgctttaa ttgaacgtga tcccaataaa acctatgacg aaatgattgc   1560
tttggctaag aaacatggag ctctgggagt acttattttt aataacaagc tggtcaatc    1620 aaaccgctca atgcgtctaa cagctaatgg gatggggata ccatctgctt tcatatcgca   1680
cgaatttggt aaggccatgt cccaattaaa tggcaatggt acaggaagtt tagagtttga   1740
cagtgtggtc tcaaaagcac cgagtcaaaa aggcaatgaa atgaatcatt tttcaaattg   1800
gggcctaact tctgatggct atttaaaacc tgacattact gcaccaggtg gcgatatcta   1860
ttctacctat aacgataacc actatggtag ccaaacagga acaagtatgg cctctcctca   1920
gattgctggc gccagccttt tggtcaaaca ataacctagaa aagactcagc caaacttgcc   1980
aaaagaaaaa attgctgata tcgttaagaa cctattgatg agcaatgctc aaattcatgt   2040
taatccagag acaaaaacga ccacctcacc gcgtcagcaa ggggcaggat tacttaatat   2100
tgacggagct gtcactagcg gcctttatgt gacaggaaaa gacaactatg gcagtatatc   2160
attaggcaac atcacagata cgatgacgtt tgatgtgact gttcacaacc taagcaataa   2220
agacaaaaca ttcgttatg acacagaatt gctaacagat catgtagacc cacaaaaggg    2280
ccgcttcact ttgacttctc actccttaaa aacgtaccaa ggaggagaag ttacagtccc   2340
agccaatgga aaagtgactg taagggttac catggatgtc tcacagttca caaaagagct   2400
```

```
aacaaaacag atgccaaatg gttactatct agaaggtttt gtccgcttta gagatagtca    2460
agatgaccaa ctaaatagag taaacattcc ttttgttggt tttaaagggc aatttgaaaa    2520
cttagcagtt gcagaagagt ccatttacag attaaaatct caaggcaaaa ctggttttta    2580
ctttgatgaa tcaggtccaa aagacgatat ctatgtcggt aaacacttta caggacttgt    2640
cactcttggt tcagagacca atgtgtcaac caaaacgatt tctgacaatg gtctacacac    2700
acttggcacc tttaaaaatg cagatggcaa atttatctta gaaaaaaatg cccaaggaaa    2760
ccctgtctta gccatttctc caaatggtga caacaaccaa gattttgcag ccttcaaagg    2820
tgttttcttg agaaaatatc aaggcttaaa agcaagtgtc taccatgcta gtgacaagga    2880
acacaaaaat ccactgtggg tcagcccaga aagctttaaa ggagataaaa actttaatag    2940
tgacattaga tttgcaaaat caacgaccct gttaggcaca gcattttctg aaaatcgtt    3000 aacaggagct gaattaccag atgggcatta tcattatgtg gtgtcttatt acccagatgt    3060
ggtcggtgcc aaacgtcaag aaatgacatt tgacatgatt ttagaccgac aaaaaccggt    3120
actatcacaa gcaacatttg atcctgaaac aaaccgattc aaaccagaac ccctaaaaga    3180
ccgtggatta gctggtgttc gcaaagacag tgtcttttat ctagaaagaa aagacaacaa    3240
gccttataca gttacgataa acgatagcta caaatatgtc tcagtagaag acaataaaac    3300
atttgtggag cgacaagctg atggcagctt tatcttgccg cttgataaag caaaattagg    3360
ggatttctat tacatggtcg aggattttgc agggaacgtg gccatcgcta agttaggaga    3420
tcacttacca caaacattag gtaaaacacc aattaaactt aagcttacag acggtaatta    3480
tcagaccaaa gaaacgctta agataatct tgaaatgaca cagtctgaca caggtctagt    3540
cacaaatcaa gcccagctag cagtggtgca ccgcaatcag ccgcaaagcc agctaacaaa    3600
gatgaatcag gatttcttta tctcaccaaa cgaagatggg aataaagact ttgtggcctt    3660
taaaggcttg aaaaataacg tgtataatga cttaacggtt aacgtatacg ctaaagatga    3720
ccaccaaaaa caaccccta tctggtctag tcaagcaggc gctagtgtat ccgctattga    3780
aagtacagcc tggtatggca taacagcccg aggaagcaag gtgatgccag gtgattatca    3840
gtatgttgtg acctatcgtg acgaacatgg taaagaacat caaaagcagt acaccatatc    3900
tgtgaatgac aaaaaaccaa tgatcactca gggacgtttt gataccatta atggcgttga    3960
ccactttact cctgacaaga caaaagccct tgactcatca ggcattgtcc gcgaagaagt    4020
cttttacttg gccaagaaaa atggccgtaa atttgatgtg acagaaggta agatggtat    4080 cacagttagt gacaataagg tgtatatccc taaaaatcca gatggttctt acaccatttc    4140
aaaaagagat ggtgtcacac tgtcagatta ttactacctt gtcgaagata gagctggtaa    4200
tgtgtctttt gctaccttgc gtgacctaaa agcggtcgga aaagacaaag cagtagtcaa    4260
ttttggatta gacttaccgg tccctgaaga caaacaaata gtgaacttta cctaccttgt    4320
gcgggatgca gatggtaaac cgattgaaaa cctagagtat tataataact caggtaacag    4380
tcttatcttg ccatacggca aatacacggt cgaattgttg acctatgaca ccaatgcagc    4440
caaactagag tcagataaaa tcgtttcctt taccttgtca gctgataaca acttccaaca    4500
agttaccttt aagataacga tgttagcaac ttctcaaata actgcccact tgatcatct    4560 tttgccagaa ggcagtcgcg ttagccttaa aacagctcaa gatcagctaa tcccgcttga    4620
acagtccttg tatgtgccta aagcttatgg caaaaccgtt caagaaggca cttacgaagt    4680
tgttgtcagc ctgcctaaag gctaccgtat cgaaggcaac acaaaggtga ataccctacc    4740
aaatgaagtg cacgaactat cattacgcct tgtcaaagta ggagatgcct cagattcaac    4800
```

```
tggtgatcat aaggttatgt caaaaaataa ttcacaggct ttgacagcct ctgccacacc    4860
aaccaagtca acgacctcag caacagcaaa agccctaa                           4898

<210> SEQ ID NO 35
<211> LENGTH: 2665
<212> TYPE: DNA
<213> ORGANISM: Artificial Sequence
<220> FEATURE:
<223> OTHER INFORMATION: vector sequence pET-21_spy_0269

<400> SEQUENCE: 35
taatacgact cactataggg gaattgtgag cggataacaa ttcccctcta gaaataattt     60
tgtttaactt taagaaggag atatacatat gaaaaagaca gctatcgcga ttgcagtggc    120
actggctggt ttcgctaccg tagcgcaggc cgatgataga gcctcaggag aaacgaaggc    180
gagtaatact cacgacgata gtttaccaaa accagaaaca attcaagagg caaaggcaac    240
tattgatgca gttgaaaaaa ctctcagtca acaaaaagca gaactgacag agcttgctac    300
cgctctgaca aaaactactg ctgaaatcaa ccacttaaaa gagcagcaag ataatgaaca    360
aaaagcttta acctctgcac aagaaattta cactaatact cttgcaagta gtgaggagac    420
gctattagcc caaggagccg aacatcaaag agagttaaca gctactgaaa cagagcttca    480
taatgctcaa gcagatcaac attcaaaaga gactgcattg tcagaacaaa agctagcat     540 ttcagcagaa actactcgag ctcaagattt agtggaacaa gtcaaaacgt ctgaacaaaa    600
tattgctaag ctcaatgcta tgattagcaa tcctgatgct atcactaaag cagctcaaac    660
ggctaatgat aatacaaaag cattaagctc agaattggag aaggctaaag ctgacttaga    720
aaatcaaaaa gctaaagtta aaaagcaatt gactgaagag ttggcagctc agaaagctgc    780
tctagcagaa aaagaggcag aacttagtcg tcttaaatcc tcagctccgt ctactcaaga    840
tagcattgtg ggtaataata ccatgaaagc accgcaaggc tatcctcttg aagaacttaa    900
aaaattagaa gctagtggtt atattggatc agctagttac aataattatt acaaagagca    960
tgcagatcaa attattgcca agctagtcc aggtaatcaa ttaaatcaat accaagatat   1020
tccagcagat cgtaatcgct tgttgatcc cgataatttg acaccagaag tgcaaaatga   1080
gctagcgcag tttgcagctc acatgattaa tagtgtaaga agacaattag gtctaccacc   1140
agttactgtt acagcaggat cacaagaatt tgcaagatta cttagtacca gctataagaa   1200
aactcatggt aatacaagac catcatttgt ctacggacag ccaggggtat cagggcatta   1260
tggtgttggg cctcatgata aaactattat tgaagactct gccggagcgt cagggctcat   1320
tcgaaatgat gataacatgt acgagaatat cggtgctttt aacgatgtgc atactgtgaa   1380
tggtattaaa cgtggtattt atgacagtat caagtatatg ctctttacag atcatttaca   1440
cggaaataca tacggccatg ctattaactt tttacgtgta gataaacata accctaatgc   1500
gcctgtttac cttggatttt caaccagcaa tgtaggatct ttgaatgaac actttgtaat   1560
gtttccagag tctaacattg ctaaccatca acgctttaat aagacccta taaaagccgt   1620 tggaagtaca aaagattatg cccaaagagt aggcactgta tctgatacta ttgcagcgat   1680
caaaggaaaa gtaagctcat tagaaaatcg tttgtcggct attcatcaag aagctgatat   1740
tatggcagcc caagctaaag taagtcaact tcaaggtaaa ttagcaagca cacttaagca   1800
gtcagacagc ttaaatctcc aagtgagaca attaaatgat actaaaggtt ctttgagaac   1860
agaattacta gcagctaaag caaaacaagc acaactcgaa gctactcgtg atcaatcatt   1920
```

| | |
|---|---|
| agctaagcta gcatcgttga aagccgcact gcaccagaca gaagccttag cagagcaagc | 1980 |
| cgcagccaga gtgacagcac tggtggctaa aaaagctcat ttgcaatatc taagggactt | 2040 |
| taaattgaat cctaaccgcc ttcaagtgat acgtgagcgc attgataata ctaagcaaga | 2100 |
| tttggctaaa actacctcat cttttgttaaa tgcacaagaa gctttagcag ccttacaagc | 2160 |
| taaacaaagc agtctagaag ctactattgc taccacagaa caccagttga ctttgcttaa | 2220 |
| aaccttagct aacgaaaagg aatatcgcca cttagacgaa gatatagcta ctgtgcctga | 2280 |
| tttgcaagta gctccacctc ttacgggcgt aaaaccgcta tcatatagta agatagatac | 2340 |
| tactccgctt gttcaagaaa tggttaaaga acgaaacaa ctattagaag cttcagcaag | 2400 |
| attagctgct gaaaatacaa gtcttgtagc agaagcgctt gttggccaaa cctctgaaat | 2460 |
| ggtagcaagt aatgccattg tgtctaaaat cacatcttcg attactcagc cctcatctaa | 2520 |
| gacatcttat ggctcaggat cttctacaac gagcaatctc atttctgatg ttgatgaaag | 2580 |
| tactcaaaga gctcttaaag caggagtcgt catgttggca gctgtcggcc tcacaggatt | 2640 |
| taggttccgt aaggaatcta agtga | 2665 |

<210> SEQ ID NO 36
<211> LENGTH: 898
<212> TYPE: DNA
<213> ORGANISM: Artificial Sequence
<220> FEATURE:
<223> OTHER INFORMATION: vector sequence pET-21_fhbp

<400> SEQUENCE: 36

| | |
|---|---|
| taatacgact cactataggg gaattgtgag cggataacaa ttcccctcta gaaataattt | 60 |
| tgtttaactt taagaaggag atatacatat gaaaaagaca gctatcgcga ttgcagtggc | 120 |
| actggctggt ttcgctaccg tagcgcaggc cgtcgccgcc gacatcggtg cggggcttgc | 180 |
| cgatgcacta accgcaccgc tcgaccataa agacaaaggt ttgcagtctt tgacgctgga | 240 |
| tcagtccgtc aggaaaaacg agaaactgaa gctggcggca aaggtgcgg aaaaaactta | 300 |
| tggaaacggt gacagcctca atacgggcaa attgaagaac gacaaggtca gccgtttcga | 360 |
| cttttatccgc caaatcgaag tggacgggca gctcattacc ttggagagtg gagagttcca | 420 |
| agtatacaaa caaagccatt ccgccttaac cgcctttcag accgagcaaa tacaagattc | 480 |
| ggagcattcc gggaagatgg ttgcgaaacg ccagttcaga atcggcgaca tagcgggcga | 540 |
| acatacatct tttgacaagc ttcccgaagg cggcagggcg acatatcgcg ggacggcgtt | 600 |
| cggttcagac gatgccggcg gaaaactgac ctacaccata gatttcgccg ccaagcaggg | 660 |
| aaacggcaaa atcgaacatt tgaaatcgcc agaactcaat gtcgacctgg ccgccgccga | 720 |
| tatcaagccg gatggaaaac gccatgccgt catcagcggt tccgtccttt acaaccaagc | 780 |
| cgagaaaggc agttactccc tcggtatctt tggcggaaaa gcccaggaag ttgccggcag | 840 |
| cgcggaagtg aaaaccgtaa acggcatacg ccatatcggc cttgccgcca agcaataa | 898 |

<210> SEQ ID NO 37
<211> LENGTH: 862
<212> TYPE: DNA
<213> ORGANISM: Artificial Sequence
<220> FEATURE:
<223> OTHER INFORMATION: vector sequence pET-21_Bla

<400> SEQUENCE: 37

| | |
|---|---|
| taatacgact cactataggg gaattgtgag cggataacaa ttcccctcta gaaataattt | 60 |
| tgtttaactt taagaaggag atatacatat gaaaaagaca gctatcgcga ttgcagtggc | 120 |

```
actggctggt tcgctaccg tagcgcaggc cagcggtaag atccttgaga gttttcgccc     180
cgaagaacgt tttccaatga tgagcacttt taaagttctg ctatgtggcg cggtattatc    240
ccgtgttgac gccgggcaag agcaactcgg tcgccgcata cactattctc agaatgactt    300
ggttgagtac tcaccagtca cagaaaagca tcttacggat ggcatgacag taagagaatt    360
atgcagtgct gccataacca tgagtgataa cactgcggcc aacttacttc tgacaacgat    420
cggaggaccg aaggagctaa ccgcttttt gcacaacatg ggggatcatg taactcgcct     480
tgatcgttgg gaaccggagc tgaatgaagc cataccaaac gacgagcgtg acaccacgat    540
gcctgcagca atggcaacaa cgttgcgcaa actattaact ggcgaactac ttactctagc   600
ttcccggcaa caattaatag actggatgga ggcggataaa gttgcaggac cacttctgcg    660
ctcggccctt ccggctggct ggtttattgc tgataaatct ggagccggtg agcgtgggtc   720
tcgcggtatc attgcagcac tggggccaga tggtaagccc tcccgtatcg tagttatcta   780
cacgacgggg agtcaggcaa ctatggatga acgaaataga cagatcgctg atataggtgc   840
ctcactgatt aagcattggt aa                                            862

<210> SEQ ID NO 38
<211> LENGTH: 4361
<212> TYPE: DNA
<213> ORGANISM: Artificial Sequence
<220> FEATURE:
<223> OTHER INFORMATION: vector sequence pET-slo+spy0269

<400> SEQUENCE: 38
taatacgact cactataggg gaattgtgag cggataacaa ttcccctcta gaaataattt    60
tgtttaactt taagaaggag atatacatat gaaaaagaca gctatcgcga ttgcagtggc   120
actggctggt ttcgctaccg tagcgcaggc caacaaacaa aacactgcta gtacagaaac   180
cacaacgaca aatgagcaac caaagccaga aagtagtgag ctaactactg aaaaagcagg   240
tcagaaaacg gatgatatgc ttaactctaa cgatatgatt aagcttgctc ccaaagaaat   300
gccactagaa tctgcagaaa aagaagaaaa aaagtcagaa gacaaaaaaa agagcgaaga   360
agatcacact gaagaaatca atgacaagat ttattcacta aattataatg agcttgaagt   420
acttgctaaa aatggtgaaa ccattgaaaa ttttgttcct aaagaaggcg ttaagaaagc   480
tgataaattt attgtcattg aaagaaagaa aaaaatatc aacactacac cagtcgatat    540
ttccattatt gactctgtca ctgataggac ctatccagca gcccttcagc tggctaataa    600
aggttttacc gaaaacaaac cagacgcggt agtcaccaag cgaaacccac aaaaaatcca    660
tattgattta ccaggtatgg gagacaaagc aacggttgag gtcaatgacc ctacctatgc   720
caatgtttca acagctattg ataatcttgt taaccaatgg catgataatt attctggtgg    780
taatacgctt cctgccagaa cacaatatac tgaatcaatg gtatattcta agtcacagat    840
tgaggcagct ctaaatgtta atagcaaaat cttagatggt actttaggca ttgatttcaa    900
gtcgatttca aaaggtgaaa agaaggtgat gattgcagca tacaagcaaa tttttttacac   960 cgtatcagca aaccttccta ataatcctgc ggatgtgttt gataaatcgg tgacctttaa   1020
agagttgcaa cgaaaaggtg tcagcaatga agctccgcca ctctttgtga gtaacgtagc   1080
ctatggtcga actgttttg tcaaactaga aacaagttct aaaagtaatg atgttgaagc    1140
ggcctttagt gcagctctaa aaggaacaga tgttaaaact aatggaaaat attctgatat   1200
cttagaaaat agctcattta cagctgtcgt tttaggagga gatgctgcag agcacaataa   1260
```

```
ggtagtcaca aaagactttg atgttattag aaacgttatc aaagacaatg ctaccttcag    1320
tagaaaaaac ctagcttatc ctatttcata caccagtgtt ttccttaaaa ataataaaat    1380
tgcgggtgtc aataacagaa ctgaatacgt tgaaacaaca tctaccgagt acactagtgg    1440
aaaaattaac ctgtctcatc aaggcgcgta tgttgctcaa tatgaaatcc tttgggatga    1500
aatcaattat gatgacaaag gaaaagaagt gattacaaaa cgacgttggg acaacaactg    1560
gtatagtaag acatcaccat ttagcacagt tatcccacta ggagctaatt cacgaaatat    1620
ccgtatcatg gctagagagt gcactggctt agctttcgaa tggtggcgaa agtgatcga    1680 cgaaagagat gtgaaactgt ctaaagaaat caatgtcaat atctcaggat caaccttgag    1740
cccatatggt tcgattactt ataagtagag aaggagatat acatatgaaa aagacagcta    1800
tcgcgattgc agtggcactg gctggtttcg ctaccgtagc gcaggccgat gatagagcct    1860
caggagaaac gaaggcgagt aatactcacg acgatagttt accaaaacca gaaacaattc    1920
aagaggcaaa ggcaactatt gatgcagttg aaaaaactct cagtcaacaa aaagcagaac    1980
tgacagagct tgctaccgct ctgacaaaaa ctactgctga atcaaccac ttaaaagagc     2040 agcaagataa tgaacaaaaa gctttaacct ctgcacaaga aatttacact aatactcttg    2100
caagtagtga ggagacgcta ttagcccaag gagccgaaca tcaaagagag ttaacagcta    2160
ctgaaacaga gcttcataat gctcaagcag atcaacattc aaaagagact gcattgtcag    2220
aacaaaaagc tagcatttca gcagaaacta ctcgagctca agatttagtg aacaagtca    2280 aaacgtctga acaaaatatt gctaagctca atgctatgat tagcaatcct gatgctatca    2340
ctaaagcagc tcaaacggct aatgataata caaaagcatt aagctcagaa ttggagaagg    2400
ctaaagctga cttagaaaat caaaaagcta agttaaaaa gcaattgact gaagagttgg      2460
cagctcagaa agctgctcta gcagaaaaag aggcagaact tagtcgtctt aaatcctcag    2520
ctccgtctac tcaagatagc attgtgggta ataataccat gaaagcaccg caaggctatc    2580
ctcttgaaga acttaaaaaa ttagaagcta gtggttatat tggatcagct agttacaata    2640
attattacaa agagcatgca gatcaaatta ttgccaaagc tagtccaggt aatcaattaa    2700
atcaatacca agatattcca gcagatcgta atcgctttgt tgatcccgat aatttgacac    2760
cagaagtgca aaatgagcta gcgcagtttg cagctcacat gattaatagt gtaagaagac    2820
aattaggtct accaccagtt actgttacag caggatcaca agaatttgca agattactta    2880
gtaccagcta taagaaaact catggtaata caagaccatc atttgtctac ggacagccag    2940
gggtatcagg gcattatggt gttgggcctc atgataaaac tattattgaa gactctgccg    3000
gagcgtcagg gctcattcga aatgatgata acatgtacga gaatatcggt gcttttaacg    3060
atgtgcatac tgtgaatggt attaaacgtg gtatttatga cagtatcaag tatatgctct    3120
ttacagatca tttacacgga aatacatacg gccatgctat taacttttta cgtgtagata    3180
aacataaccc taatgcgcct gtttaccttg gattttcaac cagcaatgta ggatctttga    3240
atgaacactt tgtaatgttt ccagagtcta acattgctaa ccatcaacgc tttaataaga    3300
cccctataaa agccgttgga agtacaaaag attatgccca agagtaggc actgtatctg      3360 atactattgc agcgatcaaa ggaaaagtaa gctcattaga aaatcgtttg tcggctattc    3420
atcaagaagc tgatattatg gcagcccaag ctaaagtaag tcaacttcaa ggtaaattag    3480
caagcacact taagcagtca gacagcttaa atctccaagt gagacaatta aatgatacta    3540
aaggttcttt gagaacagaa ttactagcag ctaaagcaaa acaagcacaa ctcgaagcta    3600
ctcgtgatca atcattagct aagctagcat cgttgaaagc cgcactgcac cagacagaag    3660
```

-continued

```
ccttagcaga gcaagccgca gccagagtga cagcactggt ggctaaaaaa gctcatttgc    3720
aatatctaag ggactttaaa ttgaatccta accgccttca agtgatacgt gagcgcattg    3780
ataatactaa gcaagatttg gctaaaacta cctcatcttt gttaaatgca caagaagctt    3840
tagcagcctt acaagctaaa caaagcagtc tagaagctac tattgctacc acagaacacc    3900
agttgacttt gcttaaaacc ttagctaacg aaaggaata tcgccactta gacgaagata    3960
tagctactgt gcctgatttg caagtagctc cacctcttac gggcgtaaaa ccgctatcat    4020
atagtaagat agatactact ccgcttgttc aagaaatggt taaagaaacg aaacaactat    4080
tagaagcttc agcaagatta gctgctgaaa atacaagtct tgtagcagaa gcgcttgttg    4140
gccaaacctc tgaaatggta gcaagtaatg ccattgtgtc taaaatcaca tcttcgatta    4200
ctcagccctc atctaagaca tcttatggct caggatcttc tacaacgagc aatctcatttt   4260
ctgatgttga tgaaagtact caaagagctc ttaaagcagg agtcgtcatg ttggcagctg    4320
tcggcctcac aggatttagg ttccgtaagg aatctaagtg a                        4361
```

<210> SEQ ID NO 39
<211> LENGTH: 1581
<212> TYPE: PRT
<213> ORGANISM: Artificial Sequence
<220> FEATURE:
<223> OTHER INFORMATION: GAS57 (D151A-DS617A)

<400> SEQUENCE: 39

```
Met Ala Asp Glu Leu Ser Thr Met Ser Glu Pro Thr Ile Thr Asn His
1               5                   10                  15

Ala Gln Gln Gln Ala Gln His Leu Thr Asn Thr Glu Leu Ser Ser Ala
                20                  25                  30

Glu Ser Lys Ser Gln Asp Thr Ser Gln Ile Thr Leu Lys Thr Asn Arg
            35                  40                  45

Glu Lys Glu Gln Ser Gln Asp Leu Val Ser Glu Pro Thr Thr Thr Glu
        50                  55                  60

Leu Ala Asp Thr Asp Ala Ala Ser Met Ala Asn Thr Gly Ser Asp Ala
65                  70                  75                  80

Thr Gln Lys Ser Ala Ser Leu Pro Pro Val Asn Thr Asp Val His Asp
                85                  90                  95

Trp Val Lys Thr Lys Gly Ala Trp Asp Lys Gly Tyr Lys Gly Gln Gly
                100                 105                 110

Lys Val Val Ala Val Ile Ala Thr Gly Ile Asp Pro Ala His Gln Ser
            115                 120                 125

Met Arg Ile Ser Asp Val Ser Thr Ala Lys Val Lys Ser Lys Glu Asp
        130                 135                 140

Met Leu Ala Arg Gln Lys Ala Ala Gly Ile Asn Tyr Gly Ser Trp Ile
145                 150                 155                 160

Asn Asp Lys Val Val Phe Ala His Asn Tyr Val Glu Asn Ser Asp Asn
                165                 170                 175

Ile Lys Glu Asn Gln Phe Glu Asp Phe Asp Glu Asp Trp Glu Asn Phe
            180                 185                 190

Glu Phe Asp Ala Glu Ala Glu Pro Lys Ala Ile Lys Lys His Lys Ile
        195                 200                 205

Tyr Arg Pro Gln Ser Thr Gln Ala Pro Lys Glu Thr Val Ile Lys Thr
    210                 215                 220

Glu Glu Thr Asp Gly Ser His Asp Ile Asp Trp Thr Gln Thr Asp Asp
225                 230                 235                 240
```

-continued

Asp Thr Lys Tyr Glu Ser His Gly Met His Val Thr Gly Ile Val Ala
            245                 250                 255

Gly Asn Ser Lys Glu Ala Ala Thr Gly Glu Arg Phe Leu Gly Ile
        260                 265                 270

Ala Pro Glu Ala Gln Val Met Phe Met Arg Val Phe Ala Asn Asp Ile
    275                 280                 285

Met Gly Ser Ala Glu Ser Leu Phe Ile Lys Ala Ile Glu Asp Ala Val
    290                 295                 300

Ala Leu Gly Ala Asp Val Ile Asn Leu Ser Leu Gly Thr Ala Asn Gly
305                 310                 315                 320

Ala Gln Leu Ser Gly Ser Lys Pro Leu Met Glu Ala Ile Glu Lys Ala
                325                 330                 335

Lys Lys Ala Gly Val Ser Val Val Ala Ala Gly Asn Glu Arg Val
            340                 345                 350

Tyr Gly Ser Asp His Asp Asp Pro Leu Ala Thr Asn Pro Asp Tyr Gly
        355                 360                 365

Leu Val Gly Ser Pro Ser Thr Gly Arg Thr Pro Thr Ser Val Ala Ala
    370                 375                 380

Ile Asn Ser Lys Trp Val Ile Gln Arg Leu Met Thr Val Lys Glu Leu
385                 390                 395                 400

Glu Asn Arg Ala Asp Leu Asn His Gly Lys Ala Ile Tyr Ser Glu Ser
                405                 410                 415

Val Asp Phe Lys Asp Ile Lys Asp Ser Leu Gly Tyr Asp Lys Ser His
            420                 425                 430

Gln Phe Ala Tyr Val Lys Glu Ser Thr Asp Ala Gly Tyr Asn Ala Gln
        435                 440                 445

Asp Val Lys Gly Lys Ile Ala Leu Ile Glu Arg Asp Pro Asn Lys Thr
    450                 455                 460

Tyr Asp Glu Met Ile Ala Leu Ala Lys Lys His Gly Ala Leu Gly Val
465                 470                 475                 480

Leu Ile Phe Asn Asn Lys Pro Gly Gln Ser Asn Arg Ser Met Arg Leu
                485                 490                 495

Thr Ala Asn Gly Met Gly Ile Pro Ser Ala Phe Ile Ser His Glu Phe
            500                 505                 510

Gly Lys Ala Met Ser Gln Leu Asn Gly Asn Gly Thr Gly Ser Leu Glu
        515                 520                 525

Phe Asp Ser Val Val Ser Lys Ala Pro Ser Gln Lys Gly Asn Glu Met
    530                 535                 540

Asn His Phe Ser Asn Trp Gly Leu Thr Ser Asp Gly Tyr Leu Lys Pro
545                 550                 555                 560

Asp Ile Thr Ala Pro Gly Gly Asp Ile Tyr Ser Thr Tyr Asn Asp Asn
                565                 570                 575

His Tyr Gly Ser Gln Thr Gly Thr Ala Met Ala Ser Pro Gln Ile Ala
            580                 585                 590

Gly Ala Ser Leu Leu Val Lys Gln Tyr Leu Glu Lys Thr Gln Pro Asn
        595                 600                 605

Leu Pro Lys Glu Lys Ile Ala Asp Ile Val Lys Asn Leu Leu Met Ser
    610                 615                 620

Asn Ala Gln Ile His Val Asn Pro Glu Thr Lys Thr Thr Ser Pro
625                 630                 635                 640

Arg Gln Gln Gly Ala Gly Leu Leu Asn Ile Asp Gly Ala Val Thr Ser
                645                 650                 655

-continued

Gly Leu Tyr Val Thr Gly Lys Asp Asn Tyr Gly Ser Ile Ser Leu Gly
                660                 665                 670

Asn Ile Thr Asp Thr Met Thr Phe Asp Val Thr Val His Asn Leu Ser
            675                 680                 685

Asn Lys Asp Lys Thr Leu Arg Tyr Asp Thr Glu Leu Leu Thr Asp His
        690                 695                 700

Val Asp Pro Gln Lys Gly Arg Phe Thr Leu Thr Ser His Ser Leu Lys
705                 710                 715                 720

Thr Tyr Gln Gly Gly Glu Val Thr Val Pro Ala Asn Gly Lys Val Thr
                725                 730                 735

Val Arg Val Thr Met Asp Val Ser Gln Phe Thr Lys Glu Leu Thr Lys
            740                 745                 750

Gln Met Pro Asn Gly Tyr Tyr Leu Glu Gly Phe Val Arg Phe Arg Asp
        755                 760                 765

Ser Gln Asp Asp Gln Leu Asn Arg Val Asn Ile Pro Phe Val Gly Phe
    770                 775                 780

Lys Gly Gln Phe Glu Asn Leu Ala Val Ala Glu Glu Ser Ile Tyr Arg
785                 790                 795                 800

Leu Lys Ser Gln Gly Lys Thr Gly Phe Tyr Phe Asp Glu Ser Gly Pro
                805                 810                 815

Lys Asp Asp Ile Tyr Val Gly Lys His Phe Thr Gly Leu Val Thr Leu
            820                 825                 830

Gly Ser Glu Thr Asn Val Ser Thr Lys Thr Ile Ser Asp Asn Gly Leu
        835                 840                 845

His Thr Leu Gly Thr Phe Lys Asn Ala Asp Gly Lys Phe Ile Leu Glu
    850                 855                 860

Lys Asn Ala Gln Gly Asn Pro Val Leu Ala Ile Ser Pro Asn Gly Asp
865                 870                 875                 880

Asn Asn Gln Asp Phe Ala Ala Phe Lys Gly Val Phe Leu Arg Lys Tyr
                885                 890                 895

Gln Gly Leu Lys Ala Ser Val Tyr His Ala Ser Asp Lys Glu His Lys
            900                 905                 910

Asn Pro Leu Trp Val Ser Pro Glu Ser Phe Lys Gly Asp Lys Asn Phe
        915                 920                 925

Asn Ser Asp Ile Arg Phe Ala Lys Ser Thr Thr Leu Leu Gly Thr Ala
    930                 935                 940

Phe Ser Gly Lys Ser Leu Thr Gly Ala Glu Leu Pro Asp Gly His Tyr
945                 950                 955                 960

His Tyr Val Val Ser Tyr Tyr Pro Asp Val Val Gly Ala Lys Arg Gln
                965                 970                 975

Glu Met Thr Phe Asp Met Ile Leu Asp Arg Gln Lys Pro Val Leu Ser
            980                 985                 990

Gln Ala Thr Phe Asp Pro Glu Thr Asn Arg Phe Lys Pro Glu Pro Leu
        995                 1000                1005

Lys Asp Arg Gly Leu Ala Gly Val Arg Lys Asp Ser Val Phe Tyr Leu
    1010                1015                1020

Glu Arg Lys Asp Asn Lys Pro Tyr Thr Val Thr Ile Asn Asp Ser Tyr
1025                1030                1035                1040

Lys Tyr Val Ser Val Glu Asp Asn Lys Thr Phe Val Glu Arg Gln Ala
                1045                1050                1055

Asp Gly Ser Phe Ile Leu Pro Leu Asp Lys Ala Lys Leu Gly Asp Phe
            1060                1065                1070

Tyr Tyr Met Val Glu Asp Phe Ala Gly Asn Val Ala Ile Ala Lys Leu

-continued

```
            1075                1080                1085
Gly Asp His Leu Pro Gln Thr Leu Gly Lys Thr Pro Ile Lys Leu Lys
        1090                1095                1100

Leu Thr Asp Gly Asn Tyr Gln Thr Lys Glu Thr Leu Lys Asp Asn Leu
1105                1110                1115                1120

Glu Met Thr Gln Ser Asp Thr Gly Leu Val Thr Asn Gln Ala Gln Leu
            1125                1130                1135

Ala Val Val His Arg Asn Gln Pro Gln Ser Gln Leu Thr Lys Met Asn
        1140                1145                1150

Gln Asp Phe Phe Ile Ser Pro Asn Glu Asp Gly Asn Lys Asp Phe Val
        1155                1160                1165

Ala Phe Lys Gly Leu Lys Asn Asn Val Tyr Asn Asp Leu Thr Val Asn
        1170                1175                1180

Val Tyr Ala Lys Asp Asp His Gln Lys Gln Thr Pro Ile Trp Ser Ser
1185                1190                1195                1200

Gln Ala Gly Ala Ser Val Ser Ala Ile Glu Ser Thr Ala Trp Tyr Gly
            1205                1210                1215

Ile Thr Ala Arg Gly Ser Lys Val Met Pro Gly Asp Tyr Gln Tyr Val
        1220                1225                1230

Val Thr Tyr Arg Asp Glu His Gly Lys Glu His Gln Lys Gln Tyr Thr
        1235                1240                1245

Ile Ser Val Asn Asp Lys Lys Pro Met Ile Thr Gln Gly Arg Phe Asp
        1250                1255                1260

Thr Ile Asn Gly Val Asp His Phe Thr Pro Asp Lys Thr Lys Ala Leu
1265                1270                1275                1280

Asp Ser Ser Gly Ile Val Arg Glu Glu Val Phe Tyr Leu Ala Lys Lys
            1285                1290                1295

Asn Gly Arg Lys Phe Asp Val Thr Glu Gly Lys Asp Gly Ile Thr Val
        1300                1305                1310

Ser Asp Asn Lys Val Tyr Ile Pro Lys Asn Pro Asp Gly Ser Tyr Thr
        1315                1320                1325

Ile Ser Lys Arg Asp Gly Val Thr Leu Ser Asp Tyr Tyr Tyr Leu Val
        1330                1335                1340

Glu Asp Arg Ala Gly Asn Val Ser Phe Ala Thr Leu Arg Asp Leu Lys
1345                1350                1355                1360

Ala Val Gly Lys Asp Lys Ala Val Val Asn Phe Gly Leu Asp Leu Pro
            1365                1370                1375

Val Pro Glu Asp Lys Gln Ile Val Asn Phe Thr Tyr Leu Val Arg Asp
        1380                1385                1390

Ala Asp Gly Lys Pro Ile Glu Asn Leu Glu Tyr Tyr Asn Asn Ser Gly
        1395                1400                1405

Asn Ser Leu Ile Leu Pro Tyr Gly Lys Tyr Thr Val Glu Leu Leu Thr
        1410                1415                1420

Tyr Asp Thr Asn Ala Ala Lys Leu Glu Ser Asp Lys Ile Val Ser Phe
1425                1430                1435                1440

Thr Leu Ser Ala Asp Asn Asn Phe Gln Gln Val Thr Phe Lys Ile Thr
            1445                1450                1455

Met Leu Ala Thr Ser Gln Ile Thr Ala His Phe Asp His Leu Leu Pro
        1460                1465                1470

Glu Gly Ser Arg Val Ser Leu Lys Thr Ala Gln Asp Gln Leu Ile Pro
        1475                1480                1485

Leu Glu Gln Ser Leu Tyr Val Pro Lys Ala Tyr Gly Lys Thr Val Gln
        1490                1495                1500
```

```
Glu Gly Thr Tyr Glu Val Val Ser Leu Pro Lys Gly Tyr Arg Ile
1505                1510                1515                1520

Glu Gly Asn Thr Lys Val Asn Thr Leu Pro Asn Glu Val His Glu Leu
            1525                1530                1535

Ser Leu Arg Leu Val Lys Val Gly Asp Ala Ser Asp Ser Thr Gly Asp
        1540                1545                1550

His Lys Val Met Ser Lys Asn Asn Ser Gln Ala Leu Thr Ala Ser Ala
    1555                1560                1565

Thr Pro Thr Lys Ser Thr Thr Ser Ala Thr Ala Lys Ala
        1570            1575                1580

<210> SEQ ID NO 40
<211> LENGTH: 4746
<212> TYPE: DNA
<213> ORGANISM: Artificial Sequence
<220> FEATURE:
<223> OTHER INFORMATION: Encodes 34-1613aa of SEQ ID NO: 39

<400> SEQUENCE: 40
atggcagatg agctaagcac aatgagcgaa ccaacaatca cgaatcacgc tcaacaacaa     60
gcgcaacatc tcaccaatac agagttgagc tcagctgaat caaaatctca agacacatca    120
caaatcactc tcaagacaaa tcgtgaaaaa gagcaatcac aagatctagt ctctgagcca    180
accacaactg agctagctga cacagatgca gcatcaatgg ctaatacagg ttctgatgcg    240
actcaaaaaa gcgcttcttt accgccagtc aatacagatg ttcacgattg gtaaaaaacc    300
aaaggagctt gggacaaggg atacaaagga caaggcaagg ttgtcgcagt tattgccaca    360
gggatcgatc cggcccatca aagcatgcgc atcagtgatg tatcaactgc taaagtaaaa    420
tcaaaagaag acatgctagc acgccaaaaa gccgccggta ttaattatgg agttggata     480 aatgataaag ttgttttgc acataattat gtggaaaata gcgataatat caaagaaaat    540
caattcgagg attttgatga ggactgggaa aactttgagt ttgatgcaga ggcagagcca    600
aaagccatca aaaacacaa gatctatcgt ccccaatcaa cccaggcacc gaaagaaact    660
gttatcaaaa cagaagaaac agatggttca catgatattg actggacaca aacagacgat    720
gacaccaaat acgagtcaca cggtatgcat gtgacaggta ttgtagccgg taatagcaaa    780
gaagccgctg ctactggaga cgctttttta ggaattgcac cagaggccca agtcatgttc    840
atgcgtgttt ttgccaacga catcatggga tcagctgaat cactctttat caaagctatc    900
gaagatgccg tggctttagg agcagatgtg atcaacctga gtcttggaac cgctaatggg    960
gcacagctta gtggcagcaa gcctctaatg gaagcaattg aaaaagctaa aaaagccggt   1020
gtatcagttg ttgtagcagc aggaaatgag gcgtctatg gatctgacca tgatgatcca   1080
ttggcgacaa atccagacta tggtttggtc ggttctccct caacaggtcg aacaccaaca   1140
tcagtggcag ctataaacag taagtgggtg attcaacgtc taatgacggt caaagaatta   1200
gaaaaccgtg ccgatttaaa ccatggtaaa gccatctatt cagagtctgt cgactttaaa   1260
gacataaaag atagcctagg ttatgataaa tcgcatcaat ttgcttatgt caaagagtca   1320
actgatgcgg ttataacgc acaagacgtt aaaggtaaaa ttgctttaat tgaacgtgat   1380
cccaataaaa cctatgacga aatgattgct ttggctaaga acatggagc tctgggagta   1440 cttatttta ataacaagcc tggtcaatca aaccgctcaa tgcgtctaac agctaatggg   1500
atggggatac catctgcttt catatcgcac gaatttggta aggccatgtc ccaattaaat   1560
ggcaatggta caggaagttt agagtttgac agtgtggtct caaaagcacc gagtcaaaaa   1620
```

```
ggcaatgaaa tgaatcattt ttcaaattgg ggcctaactt ctgatggcta tttaaaacct    1680
gacattactg caccaggtgg cgatatctat tctacctata acgataacca ctatggtagc    1740
caaacaggaa cagctatggc ctctcctcag attgctggcg ccagccttt ggtcaaacaa     1800 tacctagaaa agactcagcc aaacttgcca aagaaaaaa ttgctgatat cgttaagaac     1860
ctattgatga gcaatgctca aattcatgtt aatccagaga caaaaacgac cacctcaccg    1920
cgtcagcaag gggcaggatt acttaatatt gacggagctg tcactagcgg cctttatgtg    1980
acaggaaaag acaactatgg cagtatatca ttaggcaaca tcacagatac gatgacgttt    2040
gatgtgactg ttcacaacct aagcaataaa gacaaaacat tacgttatga cacagaattg    2100
ctaacagatc atgtagaccc acaaagggc cgcttcactt tgacttctca ctccttaaaa     2160
acgtaccaag gaggagaagt tacagtccca gccaatggaa aagtgactgt aagggttacc    2220
atggatgtct cacagttcac aaaagagcta acaaaacaga tgccaaatgg ttactatcta    2280
gaaggttttg tccgctttag agatagtcaa gatgaccaac taaatagagt aaacattcct    2340
tttgttggtt ttaaagggca atttgaaaac ttagcagttg cagaagagtc catttacaga    2400
ttaaaatcac aaggcaaaac tggttttac tttgatgaat caggtccaaa agacgatatc      2460
tatgtcggta aacactttac aggacttgtc actcttggtt cagagaccaa tgtgtcaacc    2520
aaaacgattt ctgacaatgg tctacacaca cttggcacct ttaaaaatgc agatggcaaa    2580
tttatcttag aaaaaaatgc ccaaggaaac cctgtcttag ccatttctcc aaatggtgac    2640
aacaaccaag attttgcagc cttcaaaggt gttttcttga gaaatatca aggcttaaaa     2700 gcaagtgtct accatgctag tgacaaggaa cacaaaaatc cactgtgggt cagcccagaa    2760
agctttaaag gagataaaaa ctttaatagt gacattagat ttgcaaaatc aacgaccctg    2820
ttaggcacag cattttctgg aaaatcgtta acaggagctg aattaccaga tgggcattat    2880
cattatgtgg tgtcttatta cccagatgtg gtcggtgcca acgtcaaga aatgacattt      2940 gacatgattt tagaccgaca aaaaccggta ctatcacaag caacatttga tcctgaaaca    3000
aaccgattca aaccagaacc cctaaaagac cgtggattag ctggtgttcg caaagacagt    3060 gtctttatc tagaaagaaa agacaacaag ccttatacag ttacgataaa cgatagctac     3120
aaatatgtct cagtagaaga caataaaaca tttgtggagc gacaagctga tggcagcttt    3180
atcttgccgc ttgataaagc aaaattaggg gatttctatt acatggtcga ggattttgca    3240
gggaacgtgg ccatcgctaa gttaggagat cacttaccac aaacattagg taaaacacca    3300
attaaactta gcttacagac ggtaattat cagaccaaag aaacgcttaa agataatctt      3360
gaaatgacac agtctgacac aggtctagtc acaaatcaag cccagctagc agtggtgcac    3420
cgcaatcagc cgcaaagcca gctaacaaag atgaatcagg atttctttat ctcaccaaac    3480
gaagatggga ataaagactt tgtggccttt aaaggcttga aaataacgt gtataatgac      3540 ttaacggtta acgtatacgc taaagatgac caccaaaaac aaaccctat ctggtctagt      3600 caagcaggcg ctagtgtatc cgctattgaa agtacagcct ggtatggcat aacagcccga    3660
ggaagcaagg tgatgccagg tgattatcag tatgttgtga cctatcgtga cgaacatggt    3720
aaagaacatc aaaagcagta caccatatct gtgaatgaca aaaaaccaat gatcactcag    3780
ggacgttttg ataccattaa tggcgttgac cactttactc ctgacaagac aaaagccctt    3840
gactcatcag gcattgtccg cgaagaagtc ttttacttgg ccaagaaaaa tggccgtaaa    3900
tttgatgtga cagaaggtaa agatggtatc acagttagtg acaataaggt gtatatccct    3960
```

-continued

| | |
|---|---|
| aaaaatccag atggttctta caccatttca aaaagagatg gtgtcacact gtcagattat | 4020 |
| tactaccttg tcgaagatag agctggtaat gtgtcttttg ctaccttgcg tgacctaaaa | 4080 |
| gcggtcggaa aagacaaagc agtagtcaat tttggattag acttaccggt ccctgaagac | 4140 |
| aaacaaatag tgaactttac ctaccttgtg cgggatgcag atggtaaacc gattgaaaac | 4200 |
| ctagagtatt ataataactc aggtaacagt cttatcttgc catacggcaa atacacggtc | 4260 |
| gaattgttga cctatgacac caatgcagcc aaactagagt cagataaaat cgtttccttt | 4320 |
| accttgtcag ctgataacaa cttccaacaa gttacccttta agataacgat gttagcaact | 4380 |
| tctcaaataa ctgcccactt tgatcatctt ttgccagaag gcagtcgcgt tagccttaaa | 4440 |
| acagctcaag atcagctaat cccgcttgaa cagtccttgt atgtgcctaa agcttatggc | 4500 |
| aaaaccgttc aagaaggcac ttacgaagtt gttgtcagcc tgcctaaagg ctaccgtatc | 4560 |
| gaaggcaaca caaaggtgaa taccctacca aatgaagtgc acgaactatc attacgcctt | 4620 |
| gtcaaagtag gagatgcctc agattcaact ggtgatcata aggttatgtc aaaaaataat | 4680 |
| tcacaggctt tgacagcctc tgccacacca accaagtcaa cgacctcagc aacagcaaaa | 4740 |
| gcctaa | 4746 |

<210> SEQ ID NO 41
<211> LENGTH: 543
<212> TYPE: PRT
<213> ORGANISM: Artificial Sequence
<220> FEATURE:
<223> OTHER INFORMATION: GAS25 (W535F-P427L)

<400> SEQUENCE: 41

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
            245                 250                 255

Ile Ser Lys Gly Glu Lys Lys Val Met Ile Ala Ala Tyr Lys Gln Ile
        260                 265                 270

Phe Tyr Thr Val Ser Ala Asn Leu Pro Asn Asn Pro Ala Asp Val Phe
    275                 280                 285

Asp Lys Ser Val Thr Phe Lys Glu Leu Gln Arg Lys Gly Val Ser Asn
290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
            325                 330                 335

Phe Ser Ala Ala Leu Lys Gly Thr Asp Val Lys Thr Asn Gly Lys Tyr
        340                 345                 350

Ser Asp Ile Leu Glu Asn Ser Ser Phe Thr Ala Val Val Leu Gly Gly
    355                 360                 365

Asp Ala Ala Glu His Asn Lys Val Val Thr Lys Asp Phe Asp Val Ile
370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
            405                 410                 415

Gly Val Asn Asn Arg Thr Glu Tyr Val Glu Thr Thr Ser Thr Glu Tyr
        420                 425                 430

Thr Ser Gly Lys Ile Asn Leu Ser His Gln Gly Ala Tyr Val Ala Gln
    435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
            485                 490                 495

Ile Met Ala Arg Glu Cys Thr Gly Leu Ala Phe Glu Trp Trp Arg Lys
        500                 505                 510

Val Ile Asp Glu Arg Asp Val Lys Leu Ser Lys Glu Ile Asn Val Asn
    515                 520                 525

Ile Ser Gly Ser Thr Leu Ser Pro Tyr Gly Ser Ile Thr Tyr Lys
    530                 535                 540

<210> SEQ ID NO 42
<211> LENGTH: 1632
<212> TYPE: DNA
<213> ORGANISM: Artificial Sequence
<220> FEATURE:
<223> OTHER INFORMATION: Encodes 32-571aa of SEQ ID NO: 41

<400> SEQUENCE: 42
atggctagcg aatcgaacaa acaaaacact gctagtacag aaaccacaac gacaaatgag     60
caaccaaagc cagaaagtag tgagctaact actgaaaaag caggtcagaa aacggatgat    120
atgcttaact ctaacgatat gattaagctt gctcccaaag aaatgccact agaatctgca    180
gaaaaagaag aaaaaaagtc agaagacaaa aaaagagcg aagaagatca cactgaagaa    240

```
atcaatgaca agatttattc actaaattat aatgagcttg aagtacttgc taaaaatggt    300
gaaaccattg aaaattttgt tcctaaagaa ggcgttaaga aagctgataa atttattgtc    360
attgaaagaa agaaaaaaaa tatcaacact acaccagtcg atatttccat tattgactct    420
gtcactgata ggacctatcc agcagccctt cagctggcta ataaaggttt taccgaaaac    480
aaaccagacg cggtagtcac caagcgaaac ccacaaaaaa tccatattga tttaccaggt    540 atggagaca aagcaacggt tgaggtcaat gaccctacct atgccaatgt ttcaacagct    600
attgataatc ttgttaacca atggcatgat aattattctg gtggtaatac gcttcctgcc    660
agaacacaat atactgaatc aatggtatat tctaagtcac agattgaggc agctctaaat    720
gttaatagca aaatcttaga tggtacttta ggcattgatt tcaagtcgat ttcaaaaggt    780
gaaaagaagg tgatgattgc agcatacaag caaatttttt acaccgtatc agcaaacctt    840
cctaataatc ctgcggatgt gtttgataaa tcggtgacct taaagagtt gcaacgaaaa    900 ggtgtcagca atgaagctcc gccactcttt gtgagtaacg tagcctatgg tcgaactgtt    960
tttgtcaaac tagaaacaag ttctaaaagt aatgatgttg aagcggcctt tagtgcagct   1020 ctaaaggaa cagatgttaa aactaatgga aaatattctg atatcttaga aaatagctca   1080
tttacagctg tcgttttagg aggagatgct gcagagcaca taaggtagt cacaaaagac   1140 tttgatgtta ttagaaacgt tatcaaagac aatgctacct tcagtagaaa aaacctagct   1200
tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
ccatttagca cagttatccc actaggagct aattcacgaa atatccgtat catggctaga   1500
gagtgcactg gcttagcttt cgaatggtgg cgaaaagtga tcgacgaaag agatgtgaaa   1560
ctgtctaaag aaatcaatgt caatatctca ggatcaacct tgagcccata tggttcgatt   1620
acttataagt ag                                                       1632
```

<210> SEQ ID NO 43
<211> LENGTH: 824
<212> TYPE: PRT
<213> ORGANISM: Artificial Sequence
<220> FEATURE:
<223> OTHER INFORMATION: GAS40

<400> SEQUENCE: 43

```
Met Ser Val Gly Val Ser His Gln Val Lys Ala Asp Asp Arg Ala Ser
1               5                   10                  15

Gly Glu Thr Lys Ala Ser Asn Thr His Asp Asp Ser Leu Pro Lys Pro
            20                  25                  30

Glu Thr Ile Gln Glu Ala Lys Ala Thr Ile Asp Ala Val Glu Lys Thr
        35                  40                  45

Leu Ser Gln Gln Lys Ala Glu Leu Thr Glu Leu Ala Thr Ala Leu Thr
    50                  55                  60

Lys Thr Thr Ala Glu Ile Asn His Leu Lys Glu Gln Gln Asp Asn Glu
65                  70                  75                  80

Gln Lys Ala Leu Thr Ser Ala Gln Glu Ile Tyr Thr Asn Thr Leu Ala
                85                  90                  95

Ser Ser Glu Glu Thr Leu Leu Ala Gln Gly Ala Glu His Gln Arg Glu
            100                 105                 110
```

Leu Thr Ala Thr Glu Thr Glu Leu His Asn Ala Gln Ala Asp Gln His
        115                 120                 125

Ser Lys Glu Thr Ala Leu Ser Glu Gln Lys Ala Ser Ile Ser Ala Glu
130                 135                 140

Thr Thr Arg Ala Gln Asp Leu Val Glu Gln Val Lys Thr Ser Glu Gln
145                 150                 155                 160

Asn Ile Ala Lys Leu Asn Ala Met Ile Ser Asn Pro Asp Ala Ile Thr
                165                 170                 175

Lys Ala Ala Gln Thr Ala Asn Asp Asn Thr Lys Ala Leu Ser Ser Glu
            180                 185                 190

Leu Glu Lys Ala Lys Ala Asp Leu Glu Asn Gln Lys Ala Lys Val Lys
        195                 200                 205

Lys Gln Leu Thr Glu Glu Leu Ala Ala Gln Lys Ala Ala Leu Ala Glu
    210                 215                 220

Lys Glu Ala Glu Leu Ser Arg Leu Lys Ser Ser Ala Pro Ser Thr Gln
225                 230                 235                 240

Asp Ser Ile Val Gly Asn Asn Thr Met Lys Ala Pro Gln Gly Tyr Pro
                245                 250                 255

Leu Glu Glu Leu Lys Lys Leu Glu Ala Ser Gly Tyr Ile Gly Ser Ala
            260                 265                 270

Ser Tyr Asn Asn Tyr Tyr Lys Glu His Ala Asp Gln Ile Ile Ala Lys
        275                 280                 285

Ala Ser Pro Gly Asn Gln Leu Asn Gln Tyr Gln Asp Ile Pro Ala Asp
    290                 295                 300

Arg Asn Arg Phe Val Asp Pro Asp Asn Leu Thr Pro Glu Val Gln Asn
305                 310                 315                 320

Glu Leu Ala Gln Phe Ala Ala His Met Ile Asn Ser Val Arg Arg Gln
                325                 330                 335

Leu Gly Leu Pro Pro Val Thr Val Thr Ala Gly Ser Gln Glu Phe Ala
            340                 345                 350

Arg Leu Leu Ser Thr Ser Tyr Lys Lys Thr His Gly Asn Thr Arg Pro
        355                 360                 365

Ser Phe Val Tyr Gly Gln Pro Gly Val Ser Gly His Tyr Gly Val Gly
    370                 375                 380

Pro His Asp Lys Thr Ile Ile Glu Asp Ser Ala Gly Ala Ser Gly Leu
385                 390                 395                 400

Ile Arg Asn Asp Asp Asn Met Tyr Glu Asn Ile Gly Ala Phe Asn Asp
                405                 410                 415

Val His Thr Val Asn Gly Ile Lys Arg Gly Ile Tyr Asp Ser Ile Lys
            420                 425                 430

Tyr Met Leu Phe Thr Asp His Leu His Gly Asn Thr Tyr Gly His Ala
        435                 440                 445

Ile Asn Phe Leu Arg Val Asp Lys His Asn Pro Asn Ala Pro Val Tyr
    450                 455                 460

Leu Gly Phe Ser Thr Ser Asn Val Gly Ser Leu Asn Glu His Phe Val
465                 470                 475                 480

Met Phe Pro Glu Ser Asn Ile Ala Asn His Gln Arg Phe Asn Lys Thr
                485                 490                 495

Pro Ile Lys Ala Val Gly Ser Thr Lys Asp Tyr Ala Gln Arg Val Gly
            500                 505                 510

Thr Val Ser Asp Thr Ile Ala Ala Ile Lys Gly Lys Val Ser Ser Leu
        515                 520                 525

Glu Asn Arg Leu Ser Ala Ile His Gln Glu Ala Asp Ile Met Ala Ala

Gln Ala Lys Val Ser Gln Leu Gln Gly Lys Leu Ala Ser Thr Leu Lys
545                 550                 555                 560

Gln Ser Asp Ser Leu Asn Leu Gln Val Arg Gln Leu Asn Asp Thr Lys
                565                 570                 575

Gly Ser Leu Arg Thr Glu Leu Leu Ala Ala Lys Ala Lys Gln Ala Gln
            580                 585                 590

Leu Glu Ala Thr Arg Asp Gln Ser Leu Ala Lys Leu Ala Ser Leu Lys
        595                 600                 605

Ala Ala Leu His Gln Thr Glu Ala Leu Ala Glu Gln Ala Ala Arg
    610                 615                 620

Val Thr Ala Leu Val Ala Lys Lys Ala His Leu Gln Tyr Leu Arg Asp
625                 630                 635                 640

Phe Lys Leu Asn Pro Asn Arg Leu Gln Val Ile Arg Glu Arg Ile Asp
                645                 650                 655

Asn Thr Lys Gln Asp Leu Ala Lys Thr Thr Ser Ser Leu Leu Asn Ala
            660                 665                 670

Gln Glu Ala Leu Ala Ala Leu Gln Ala Lys Gln Ser Ser Leu Glu Ala
        675                 680                 685

Thr Ile Ala Thr Thr Glu His Gln Leu Thr Leu Leu Lys Thr Leu Ala
    690                 695                 700

Asn Glu Lys Glu Tyr Arg His Leu Asp Glu Asp Ile Ala Thr Val Pro
705                 710                 715                 720

Asp Leu Gln Val Ala Pro Pro Leu Thr Gly Val Lys Pro Leu Ser Tyr
                725                 730                 735

Ser Lys Ile Asp Thr Thr Pro Leu Val Gln Glu Met Val Lys Glu Thr
            740                 745                 750

Lys Gln Leu Leu Glu Ala Ser Ala Arg Leu Ala Ala Glu Asn Thr Ser
        755                 760                 765

Leu Val Ala Glu Ala Leu Val Gly Gln Thr Ser Glu Met Val Ala Ser
    770                 775                 780

Asn Ala Ile Val Ser Lys Ile Thr Ser Ser Ile Thr Gln Pro Ser Ser
785                 790                 795                 800

Lys Thr Ser Tyr Gly Ser Gly Ser Ser Thr Thr Ser Asn Leu Ile Ser
                805                 810                 815

Asp Val Asp Glu Ser Thr Gln Arg
            820

<210> SEQ ID NO 44
<211> LENGTH: 2475
<212> TYPE: DNA
<213> ORGANISM: Artificial Sequence
<220> FEATURE:
<223> OTHER INFORMATION: Encodes 27-849aa of SEQ ID NO: 43

<400> SEQUENCE: 44
atgagtgtag gcgtatctca ccaagtcaaa gcagatgata gagcctcagg agaaacgaag    60
gcgagtaata ctcacgacga tagtttacca aaaccagaaa caattcaaga ggcaaaggca   120
actattgatg cagttgaaaa aactctcagt caacaaaaag cagaactgac agagcttgct   180
accgctctga caaaaactac tgctgaaatc aaccacttaa aagagcagca agataatgaa   240
caaaaagctt taacctctgc acaagaaatt tacactaata ctcttgcaag tagtgaggag   300
acgctattag cccaaggagc cgaacatcaa agagagttaa cagctactga acagagcttt   360
cataatgctc aagcagatca acattcaaaa gagactgcat tgtcagaaca aaaagctagc   420

```
atttcagcag aaactactcg agctcaagat ttagtggaac aagtcaaaac gtctgaacaa    480
aatattgcta agctcaatgc tatgattagc aatcctgatg ctatcactaa agcagctcaa    540
acggctaatg ataatacaaa agcattaagc tcagaattgg agaaggctaa agctgactta    600
gaaaatcaaa aagctaaagt taaaaagcaa ttgactgaag agttggcagc tcagaaagct    660
gctctagcag aaaagaggc agaacttagt cgtcttaaat cctcagctcc gtctactcaa    720
gatagcattg tgggtaataa taccatgaaa gcaccgcaag gctatcctct tgaagaactt    780
aaaaaattag aagctagtgg ttatattgga tcagctagtt acaataatta ttacaaagag    840
catgcagatc aaattattgc caaagctagt ccaggtaatc aattaaatca ataccaagat    900
attccagcag atcgtaatcg ctttgttgat cccgataatt tgacaccaga agtgcaaaat    960
gagctagcgc agtttgcagc tcacatgatt aatagtgtac gtcgtcaatt aggtctacca   1020
ccagttactg ttacagcagg atcacaagaa tttgcaagat tacttagtac cagctataag   1080
aaaactcatg gtaatacaag accatcattt gtctacggac agccagggggt atcagggcat  1140 tatggtgttg ggcctcatga taaaactatt attgaagact ctgccggagc gtcagggctc   1200
attcgaaatg atgataacat gtacgagaat atcggtgctt ttaacgatgt gcatactgtg   1260
aatggtatta acgtggtat ttatgacagt atcaagtata tgctctttac agatcattta    1320
cacggaaata catacggcca tgctattaac tttttacgtg tagataaaca taaccctaat   1380
gcgcctgttt accttggatt ttcaaccagc aatgtaggat ctttgaatga cactttgta   1440 atgtttccag agtctaacat tgctaaccat caacgcttta ataagacccc tataaaagcc   1500
gttggaagta caaagatta tgcccaaaga gtaggcactg tatctgatac tattgcagcg   1560
atcaaaggaa aagtaagctc attagaaaat cgtttgtcgg ctattcatca agaagctgat   1620
attatggcag cccaagctaa agtaagtcaa cttcaaggta aattagcaag cacacttaag   1680
cagtcagaca gcttaaatct ccaagtgaga caattaaatg atactaaagg ttcttttgaga  1740 acagaattac tagcagctaa agcaaaacaa gcacaactcg aagctactcg tgatcaatca   1800
ttagctaagc tagcatcgtt gaaagccgca ctgcaccaga cagaagcctt agcagagcaa   1860
gccgcagcca gagtgacagc actggtggct aaaaaagctc atttgcaata tctaagggac   1920
tttaaattga atcctaaccg ccttcaagtg atacgtgagc gcattgataa tactaagcaa   1980
gatttggcta aaactacctc atctttgtta aatgcacaag aagctttagc agccttacaa   2040
gctaaacaaa gcagtctaga agctactatt gctaccacag aacaccagtt gactttgctt   2100
aaaaccttag ctaacgaaaa ggaatatcgc cacttagacg aagatatagc tactgtgcct   2160
gatttgcaag tagctccacc tcttacgggc gtaaaaccgc tatcatatag taagatagat   2220
actactccgc ttgttcaaga aatggttaaa gaaacgaaac aactattaga agcttcagca   2280
agattagctg ctgaaaatac aagtcttgta gcagaagcgc ttgttggcca aacctctgaa   2340
atggtagcaa gtaatgccat tgtgtctaaa atcacatctt cgattactca gccctcatct   2400
aagacatctt atggctcagg atcttctaca acgagcaatc tcatttctga tgttgatgaa   2460
agtactcaac gttaa                                                    2475
```

<210> SEQ ID NO 45
<211> LENGTH: 2622
<212> TYPE: DNA
<213> ORGANISM: Artificial Sequence
<220> FEATURE:
<223> OTHER INFORMATION: GAS40variant1

```
<400> SEQUENCE: 45
atggacttag aacaaacgaa gccaaaccaa gttaagcaga aaattgcttt aacctcaaca      60
attgctttat tgagtgccag tgtaggcgta tctcaccaag tcaaagcaga tgatagagcc     120
tcaggagaaa cgaaggcgag taatactcac gacgatagtt taccaaaacc agaaacaatt     180
caagaggcaa aggcaactat tgatgcagtt gaaaaaactc tcagtcaaca aaaagcagaa     240
ctgacagagc ttgctaccgc tctgacaaaa actactgctg aaatcaacca cttaaaagag     300
cagcaagata atgaacaaaa agctttaacc tctgcacaag aaatttacac taatactctt     360
gcaagtagtg aggagacgct attagcccaa ggagccgaac atcaaagaga gttaacagct     420
actgaaacag agcttcataa tgctcaagca gatcaacatt caaaagagac tgcattgtca     480
gaacaaaaag ctagcatttc agcagaaact actcgagctc aagatttagt ggaacaagtc     540
aaaacgtctg aacaaaatat tgctaagctc aatgctatga ttagcaatcc tgatgctatc     600
actaaagcag ctcaaacggc taatgataat acaaaagcat aagctcaga attggagaag     660 gctaaagctg acttagaaaa tcaaaaagct aaagttaaaa agcaattgac tgaagagttg     720
gcagctcaga aagctgctct agcagaaaaa gaggcagaac ttagtcgtct taaatcctca     780
gctccgtcta ctcaagatag cattgtgggt aataatacca tgaaagcacc gcaaggctat     840
cctcttgaag aacttaaaaa attagaagct agtggttata ttggatcagc tagttacaat     900
aattattaca aagagcatgc agatcaaatt attgccaaag ctagtccagg taatcaatta     960
aatcaatacc aagatattcc agcagatcgt aatcgctttg ttgatcccga taatttgaca    1020
ccagaagtgc aaaatgagct agcgcagttt gcagctcaca tgattaatag tgtaagaaga    1080
caattaggtc taccaccagt tactgttaca gcaggatcac aagaatttgc aagattactt    1140
agtaccagct ataagaaaac tcatggtaat acaagaccat catttgtcta cggacagcca    1200
ggggtatcag gcattatgg tgtttgggcct catgataaaa ctattattga agactctgcc    1260
ggagcgtcag gctcattcg aaatgatgat aacatgtacg agaatatcgg tgctttaac    1320 gatgtgcata ctgtgaatgg tattaaacgt ggtatttatg acagtatcaa gtatatgctc    1380
tttacagatc atttacacgg aaatacatac ggccatgcta ttaacttttt acgtgtagat    1440
aaacataacc ctaatgcgcc tgtttacctt ggattttcaa ccagcaatgt aggatctttg    1500
aatgaacact ttgtaatgtt tccagagtct aacattgcta accatcaacg ctttaataag    1560 accccctataa aagccgttgg aagtacaaaa gattatgccc aaagagtagg cactgtatct    1620
gatactattg cagcgatcaa aggaaaagta agctcattag aaaatcgttt gtcggctatt    1680
catcaagaag ctgatattat ggcagcccaa gctaaagtaa gtcaacttca aggtaaatta    1740
gcaagcacac ttaagcagtc agacagctta aatctccaag tgagacaatt aaatgatact    1800
aaaggttctt tgagaacaga attactagca gctaaagcaa aacaagcaca actcgaagct    1860
actcgtgatc aatcattagc taagctagca tcgttgaaag ccgcactgca ccagacagaa    1920
gccttagcag agcaagccgc agccagagtg acagcactgg tggctaaaaa agctcatttg    1980
caatatctaa gggactttaa attgaatcct aaccgccttc aagtgatacg tgagcgcatt    2040
gataatacta agcaagattt ggctaaaact acctcatctt tgttaaatgc acaagaagct    2100
ttagcagcct acaagctaa acaaagcagt ctagaagcta ctattgctac cacagaacac    2160
cagttgactt tgcttaaaac cttagctaac gaaaaggaat atcgccactt agacgaagat    2220
atagctactg tgcctgattt gcaagtagct ccacctctta cgggcgtaaa accgctatca    2280
tatagtaaga tagatactac tccgcttgtt caagaaatgg ttaaagaaac gaaacaacta    2340
```

```
ttagaagctt cagcaagatt agctgctgaa aatacaagtc ttgtagcaga agcgcttgtt   2400
ggccaaacct ctgaaatggt agcaagtaat gccattgtgt ctaaaatcac atcttcgatt   2460
actcagccct catctaagac atcttatggc tcaggatctt ctacaacgag caatctcatt   2520
tctgatgttg atgaaagtac tcaaagagct cttaaagcag gagtcgtcat gttggcagct   2580
gtcggcctca caggatttag gttccgtaag gaatctaagt ga                      2622
```

<210> SEQ ID NO 46
<211> LENGTH: 2622
<212> TYPE: DNA
<213> ORGANISM: Artificial Sequence
<220> FEATURE:
<223> OTHER INFORMATION: GAS40variant2

<400> SEQUENCE: 46

```
atggacttag aacaaacgaa gccaaaccaa gttaagcaga aaattgcttt aacctcaaca     60
attgctttat tgagtgccag tgtaggcgta tctcaccaag tcaaagcaga tgatagagcc    120
tcaggagaaa cgaaggcgag taatactcac gacgatagtt taccaaaacc agaaacaatt    180
caagaggcaa aggcaactat tgatgcagtt gaaaaaactc tcagtcaaca aaagcagaa    240
ctgacagagc ttgctaccgc tctgacaaaa actactgctg aaatcaacca cttaaaagag    300
cagcaagata tgaacaaaaa agctttaacc tctgcacaag aaatttacac taatactctt    360
gcaagtagtg aggagacgct attagcccaa ggagccgaac atcaaagaga gttaacagct    420
actgaaacag agcttcataa tgctcaagca gatcaacatt caaagagac tgcattgtca     480
gaacaaaaag ctagcatttc agcagaaact actcgagctc aagatttagt ggaacaagtc    540
aaaacgtctg aacaaaatat tgctaagctc aatgctatga ttagcaatcc tgatgctatc    600
actaaagcag ctcaaacggc taatgataat acaaaagcat taagctcaga attggagaag    660
gctaaagctg acttagaaaa tcaaaaagct aaagttaaaa agcaattgac tgaagagttg    720
gcagctcaga aagctgctct agcagaaaaa gaggcagaac ttagtcgtct taaatcctca    780
gctccgtcta ctcaagatag cattgtgggt aataatacca tgaaagcacc gcaaggctat    840
cctcttgaag aacttaaaaa attagaagct agtggttata ttggatcagc tagttacaat    900
aattattaca agagcatgc agatcaaatt attgccaaag ctagtccagg taatcaatta    960
aatcaatacc aagatattcc agcagatcgt aatcgctttg ttgatcccga atttgaca    1020
ccagaagtgc aaaatgagct agcgcagttt gcagctcaca tgattaatag tgtaagaaga   1080
caattaggtc taccaccagt tactgttaca gcaggatcac aagaatttgc aagattactt   1140
agtaccagct ataagaaaac tcatggtaat acaagaccat catttgtcta cggacagcca   1200
ggggtatcag ggcattatgg tgttgggcct catgataaaa ctattattga agactctgcc   1260
ggagcgtcag ggctcattcg aaatgatgat aacatgtacg agaatatcgg tgcttttaac   1320
gatgtgcata ctgtgaatgg tattaaacgt ggtatttatg acagtatcaa gtatatgctc   1380
tttacagatc atttacacgg aaatacatac ggccatgcta ttaactttt acgtgtagat    1440
aaacataacc ctaatgcgcc tgtttacctt ggattttcaa ccagcaatgt aggatctttg   1500
aatgaacact ttgtaatgtt tccagagtct aacattgcta ccatcaacg ctttaataag   1560
accctataa agccgttgg aagtacaaaa gattatgccc aaagagtagg cactgtatct   1620
gatactattg cagcgatcaa aggaaaagta agctcattag aaaatcgttt gtcggctatt   1680
catcaagaag ctgatattat ggcagcccaa gctaaagtaa gtcaacttca aggtaaatta   1740
```

```
gcaagcacac ttaagcagtc agacagctta aatctccaag tgagacaatt aaatgatact    1800
aaaggttctt tgagaacaga attactagca gctaaagcaa acaagcaca actcgaagct    1860 actcgtgatc aatcattagc taagctagca tcgttgaaag ccgcactgca ccagacagaa    1920
gccttagcag agcaagccgc agccagagtg acagcactgg tggctaaaaa agctcatttg    1980
caatatctaa gggactttaa attgaatcct aaccgccttc aagtgatacg tgagcgcatt    2040
gataatacta agcaagattt ggctaaaact acctcatctt tgttaaatgc aagaagct    2100 ttagcagcct tacaagctaa acaaagcagt ctagaagcta ctattgctac cacagaacac    2160
cagttgactt tgcttaaaac cttagctaac gaaaaggaat atcgccactt agacgaagat    2220
atagctactg tgcctgattt gcaagtagct ccacctctta cgggcgtaaa accgctatca    2280
tatagtaaga tagatactac tccgcttgtt caagaaatgg ttaaagaaac gaaacaacta    2340
ttagaagctt cagcaagatt agctgctgaa atacaagtc ttgtagcaga agcgcttgtt    2400
ggccaaacct ctgaaatggt agcaagtaat gccattgtgt ctaaaatcac atcttcgatt    2460 actcagcccct catctaagac atcttatggc tcaggatctt ctacaacgag caatctcatt    2520
tctgatgttg atgaaagtac tcaaagagct cttaaagcag gagtcgtcat gttggcagct    2580
gtcggcctca caggatttag gttccgtaag gaatctaagt ga                       2622

<210> SEQ ID NO 47
<211> LENGTH: 1356
<212> TYPE: DNA
<213> ORGANISM: Artificial Sequence
<220> FEATURE:
<223> OTHER INFORMATION: GAS40variant3

<400> SEQUENCE: 47
gatgatagag cctcaggaga aacgaaggcg agtaatactc acgacgatag tttaccaaaa      60
ccagaaacaa ttcaagaggc aaaggcaact attgatgcag ttgaaaaaac tctcagtcaa     120
caaaaagcag aactgacaga gcttgctacc gctctgacaa aaactactgc tgaaatcaac     180
aacttaaaag agcagcaaga taatgaacaa aaagctttaa cctctgcaca agaaatttac     240
actaatactc ttgcaagtag tgaggagacg ctattagccc aaggagccga acatcaaaga     300
gagttaacag ctactgaaac agagcttcat aatgctcaag cagatcaaca ttcaaaagag     360
actgcattgt cagaacaaaa agctagcatt tcagcagaaa ctactcgagc tcaagattta     420
gtggaacaag tcaaaacgtc tgaacaaaat attgctaagc tcaatgctat gattagcaat     480
cctgatgcta tcactaaagc agctcaaacg gctaatgata atacaaaagc attaagctca     540
gaattggaga aggctaaagc tgacttagaa aatcaaaaag ctaaagttaa aaagcaattg     600
actgaagagt tggcagctca gaaagctgct ctagcagaaa aagaggcaga acttagtcgt     660
cttaaatcct cagctccgtc tactcaagat agcattgtgg gtaataatac catgaaagca     720
ccgcaaggct atcctcttga agaacttaaa aaattagaag ctagtggtta tattggatca     780
gctagttaca ataattatta caaagagcat gcagatcaaa ttattgccaa agctagtcca     840
ggtaatcaat taaatcaata ccaagatatt ccagcagatc gtaatcgctt tgttgatccc     900
gataatttga caccgaagt gcaaaatgag ctagcgcagt ttgcagctca catgattaat     960
agtgtaagaa gacaattagg tctaccacca gttactgtta cagcaggatc acaagaattt    1020
gcaagattac ttagtaccag ctataagaaa actcatggta atacaagacc atcatttgtc    1080 tacgacagc aggggtatc agggcattat ggtgttgggc ctcatgataa aactattatt    1140
gaagactctg ccggagcgtc agggctcatt cgaaatgatg ataacatgta cgagaatatc    1200
```

```
ggtgctttta acgatgtgca tactgtgaat ggtattaaac gtggtattta tgacagtatc    1260
aagtatatgc tctttacaga tcatttacac ggaaatacat acggccatgc tattaacttt    1320
ttacgtgtag ataaacgtaa ccctaatgcg cctgtt                              1356
```

<210> SEQ ID NO 48
<211> LENGTH: 1356
<212> TYPE: DNA
<213> ORGANISM: Artificial Sequence
<220> FEATURE:
<223> OTHER INFORMATION: GAS40variant4

<400> SEQUENCE: 48

```
gatgatagag cctcaggaga acgaaggcg agtaatactc acgacgatag tttaccaaaa     60
ccagaaacaa ttcaagaggc aaaggcaact attgatgcag ttgaaaaaac tctcagtcaa    120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa aagaggcaga acttagtcgt    660
cttaaatcct cagctccgtc tactcaagat agcattgtgg gtaataatac catgaaagca    720
ccgcaaggct atcctcttga agaacttaaa aaattagaag ctagtggtta tattggatca    780
gctagttaca ataattatta caagagcat gcagatcaaa ttattgccaa agctagtcca    840
ggtaatcaat taaatcaata ccaagatatt ccagcagatc gtaatcgctt tgttgatccc    900
gataatttga caccagaagt gcaaaatgag ctagcgcagt ttgcagctca catgattaat    960
agtgtaagga gacaattagg tctaccacca gttactgtca cagcaggatc acaagaattt   1020
gcaagattac ttagtaccag ctataagaaa actcatggta atacaagacc atcatttgtc   1080 tacgacagc caggggtatc agggcattat ggtgttgggc ctcatgataa aactattatt   1140
gaagactctg ccggagcgtc agggctcatt cgaaatgatg ataacatgta cgagaatatc   1200
ggtgctttta acgatgtgca tactgtgaat ggtattaaac gtggtattta tgacagtatc   1260
aagtatatgc tctttacaga tcatttacac ggaaatacat atggtcatgc tattaacttt   1320
ttacgtgtag ataaacataa ccctaaggcg cctgtt                              1356
```

<210> SEQ ID NO 49
<211> LENGTH: 1356
<212> TYPE: DNA
<213> ORGANISM: Artificial Sequence
<220> FEATURE:
<223> OTHER INFORMATION: GAS40variant5

<400> SEQUENCE: 49

```
gatgatagag cctcaggaga acgaaggcg agtaatactc acgacgatag tttaccaaaa     60
ccagaaacaa ttcaagaggc aaaggcaact attgatgcag ttgaaaaaac tctcagtcaa    120
caaaaagcag aactgacaaa gcttgctacc gctctgacaa aaactactgc tgaaatcaac    180
```

```
cacttaaaag agcagcaaga taatgaacaa aaagctttaa cctctgcaca agaaatttac      240
actaatactc ttgcaagtag tgaggagacg ctattagccc aaggagccga acatcaaaga      300
gagttaacag ctactgaaac agagcttcat aatgctcaag cagatcaaca ttcaaaagag      360
actgcattgt cagaacaaaa agctagcatt tcagcagaaa ctactcgagc tcaagattta      420
gtggaacaag tcaaaacgtc tgaacaaaat attgctaagc tcaatgctat gattagcaat      480
cctgatgcta tcactaaagc agctcaaacg gctaatgata atacaaaagc attaagctca      540
gaattggaga aggctaaagc tgacttagaa aatcaaaaag ctaaagttaa aaagcaattg      600
actgaagagt tggcagctca gaaagctgct ctagcagaaa aagaggcaga acttagtcgt      660
cttaaatcct cagctccgtc tactcaagat agcattgtgg gtaataatac catgaaagca      720
ccgcaaggct atcctcttga agaacttaaa aaattagaag ctagtggtta tattggatca      780
gctagttaca ataattatta caaagagcat gcagatcaaa ttattgccaa agctagtcca      840
ggtaatcaat taaatcaata ccaagatatt ccagcagatc gtaatcgctt tgttgatccc      900
gataatttga caccagaagt gcaaaatgag ctagcgcagt ttgcagctca catgattaat      960
agtgtaagaa gacaattagg tctaccacca gttactgtta cagcaggatc acaagaattt     1020
gcaagattac ttagtaccag ctataagaaa actcatggta atacaagacc atcatttgtc     1080
tacggacagc caggggtatc agggcattat ggtgttgggc tcatgataaa actattatt      1140 gaagactctg ccggagcgtc agggctcatt cgaaatgatg ataacatgta cgagaatatc     1200 ggtgcttta acgatgtgca tactgtgaat ggtattaaac gtggtattta tgacagtatc     1260
aagtatatgc tctttacaga tcatttacac ggaaatacat acggccatgc tattaacttt     1320
ttacgtgtag ataaacgtaa ccctaatgcg cctgtt                              1356
```

<210> SEQ ID NO 50
<211> LENGTH: 1356
<212> TYPE: DNA
<213> ORGANISM: Artificial Sequence
<220> FEATURE:
<223> OTHER INFORMATION: GAS40variant6

<400> SEQUENCE: 50

```
gatgatagag cctcaggaga aacgaaggcg agtaatactc acgacgatag tttaccaaaa       60
ccagaaacaa ttcaagaggc aaaggcaact attgaagcag ttgaaaaagc tctcagtcaa      120
caaaaagcag aactgacaga gcttgctacc gctctgacaa aaactactgc taaaatcaac      180
cacttaaaag agcagcaaga taatgaacaa aaagctttaa cctctgcaca agaaatttac      240
actaatactc ttgcaagtag tgaggagacg ctattagccc aaggagccga acatcaaaga      300
gagttaacag ctactgaaac agagcttcat aatgctcaag cagatcaaca ttcaaaagag      360
actgcattgt cagaacaaaa agctagcatt tcagcagaaa ctactcgagc tcaagattta      420
gtggaacaag tcaaaacgtc tgaacaaaat attgctaagc tcaatgctat gattagtaat      480
cctgatgcta tcactaaagc agctcaaacg gctaatgata atacaaaagc attaagctca      540
gaattggaga aggctaaagc tgacttagaa aatcaaaaag ctaaagttaa aaagcaattg      600
actgaagagt tggcagctca gaaagctgct ctagcagaaa aagaggcaga acttagtcgt      660
cttaaatcct cagctccgtc tactcaagat agcattgtgg gtaataatac catgaaagca      720
ccgcaaggct atcctcttga agaacttaaa aaattagaag ctagtggtta tattggatca      780
gctagttaca ataattatta caaagagcat gcagatcaaa ttattgccaa agctagtcca      840
ggtaatcaat taaatcaata ccaagatatt ccagcagatc gtaatcgctt tgttgatccc      900
```

```
gataatttga caccagaagt gcaaaatgag ctagcgcagt ttgcagctca catgattaat      960
agtgtaagaa gacaattagg tctaccacca gttactgtca cagcaggatc acaagaattt     1020
gcaagattac ttagtaccag ctataagaaa actcatggta atacaagacc atcatttgtc     1080
tacggacagc caggggtatc agggcattat ggtgttgggc ctcatgataa aactattatt     1140
gaagactctg ccggagcgtc agggctcatt cgaaatgatg ataacatgta cgagaatatc     1200
ggtgctttta acgatgtgca tactgtgaat ggtattaaac gtggtattta tgacagtatc     1260
aagtatatgc tctttacaga tcatttacac ggaaatacat atggccatgc tattaacttt     1320
ttacgtgtag ataaacgtaa ccctaatgcg cctgtt                              1356
```

```
<210> SEQ ID NO 51
<211> LENGTH: 1356
<212> TYPE: DNA
<213> ORGANISM: Artificial Sequence
<220> FEATURE:
<223> OTHER INFORMATION: GAS40variant7

<400> SEQUENCE: 51
```

```
gatgatagag cctcaggaga aacgaaggcg agtaatactc acgacgatag tttaccaaaa       60
ccagaaacaa ttcaagaggc aaaggcaact attgaagcag ttgaaaaagc tctcagtcaa      120
caaaaagcag aactgacaga gcttgctacc gctctgacaa aaactactgc taaaatcaac      180
cacttaaaag agcagcaaga taatgaacaa aaagctttaa cctctgcaca agaaatttac      240
actaatactc ttgcaagtag tgaggagacg ctattagccc aaggagccga acatcaaaga      300
gagttaacag ctactgaaac agagcttcat aatgctcaag cagatcaaca ttcaaaagag      360
actgcattgt cagaacaaaa agctagcatt tcagcagaaa ctactcgagc tcaagattta      420
gtggaacaag tcaaaacgtc tgaacaaaat attgctaagc tcaatgctat gattagtaat      480
cctgatgcta tcactaaagc agctcaaacg gctaatgata tacaaaagc attaagctca      540 gaattggaga aggctaaagc tgacttagaa aatcaaaaag ctaaagttaa aaagcaattg      600
actgaagagt tggcagctca gaaagctgct ctagcagaaa aagaggcaga acttagtcgt      660
cttaaatcct cagctccgtc tactcaagat agcattgtgg gtaataatac catgaaagca      720
ccgcaaggct atcctcttga agaacttaaa aaattagaag ctagtggtta tattggatca      780
gctagttaca ataattatta caaagagcat gcagatcaaa ttattgccaa agctagtcca      840
ggtaatcaat aaatcaata ccaagatatt ccagcagatc gtaatcgctt tgttgatccc      900
gataatttga caccagaagt gcaaaatgag ctagcgcagt ttgcagctca catgattaat      960
agtgtaagaa gacaattagg tctaccacca gttactgtca cagcaggatc acaagaattt     1020
gcaagattac ttagtaccag ctataagaaa actcatggta atacaagacc atcatttgtc     1080
tacggacagc caggggtatc agggcattat ggtgttgggc ctcatgataa aactattatt     1140
gaagactctg ccggagcgtc agggctcatt cgaaatgatg ataacatgta cgagaatatc     1200
ggtgctttta acgatgtgca tactgtgaat ggtattaaac gtggtattta tgacagtatc     1260
aagtatatgc tctttacaga tcatttacac ggaaatacat atggccatgc tattaacttt     1320
ttacgtgtag ataaacgtaa ccctaatgcg cctgtt                              1356
```

```
<210> SEQ ID NO 52
<211> LENGTH: 1356
<212> TYPE: DNA
<213> ORGANISM: Artificial Sequence
<220> FEATURE:
```

<223> OTHER INFORMATION: GAS40variant8

<400> SEQUENCE: 52

```
gatgatagag cctcaggaga acgaaggcg agtaatactc acgacgatag tttaccaaaa      60
ccagaaacaa ttcaagaggc aaaggcaact attgatgcag ttgaaaaaac tctcagtcaa     120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa agagggcaga acttagtcgt    660
cttaaatcct cagctccgtc tactcaagat agcattgtgg gtaataatac catgaaagca    720
ccgcaaggct atcctcttga gaacttaaaa aattagaag ctagtggtta tattggatca    780
gctagttaca ataattatta caaagagcat gcagatcaaa ttattgccaa agctagtcca    840
ggtaatcaat taaatcaata ccaagatatt ccagcagatc gtaatcgctt tgttgatccc    900
gataatttga caccagaagt gcaaaatgag ctagcgcagt ttgcagctca catgattaat    960
agtgtaagaa gacaattagg tctaccacca gttactgtta cagcaggatc acaagaattt   1020
gcaagattac ttagtaccag ctataagaaa actcatggta atacaagacc atcatttgtc   1080
tacgacagc caggggtatc agggcattat ggtgttgggc tcatgataaa actattatt    1140
gaagactctg ccggagcgtc agggctcatt cgaaatgatg ataacatgta cgagaatatc   1200
ggtgcttta cgatgtgca tactgtgaat ggtattaaac gtggtattta tgacagtatc    1260
aagtatatgc tctttacaga tcatttacac ggaaatacat acggccatgc tattaacttt   1320
ttacgtgtag ataaacgtaa ccctaatgcg cctgtt                                  1356
```

<210> SEQ ID NO 53
<211> LENGTH: 1356
<212> TYPE: DNA
<213> ORGANISM: Artificial Sequence
<220> FEATURE:
<223> OTHER INFORMATION: GAS40variant9

<400> SEQUENCE: 53

```
gatgatagag cctcaggaga acgaaggcg agtaatactc acgacgatag tttaccaaaa      60
ccagaaacaa ttcaagaggc aaaggcaact attgatgcag ttgaaaaaac tctcagtcaa     120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
```

```
actgaagagt tggcagctca gaaagctgct ctagcagaaa aagaggcaga acttagtcgt      660
cttaaatcct cagctccgtc tactcaagat agcattgtgg gtaataatac catgaaagca      720
ccgcaaggct atcctcttga agaacttaaa aaattagaag ctagtggtta tattggatca      780
gctagttaca ataattatta caaagagcat gcagatcaaa ttattgccaa agctagtcca      840
ggtaatcaat taaatcaata ccaagatatt ccagcagatc gtaatcgctt tgttgatccc      900
gataatttga caccagaagt gcaaaatgag ctagcgcagt ttgcagctca catgattaat      960
agtgtaagaa gacaattagg tctaccacca gttactgtta cagcaggatc acaagaattt     1020
gcaagattac ttagtaccag ctataagaaa actcatggta atacaagacc atcatttgtc     1080
tacggacagc caggggtatc agggcattat ggtgttgggc ctcatgataa aactattatt     1140
gaagactctg ccggagcgtc agggctcatt cgaaatgatg ataacatgta cgagaatatc     1200
ggtgctttta acgatgtgca tactgtgaat ggtattaaac gtggtattta tgacagtatc     1260
aagtatatgc tctttacaga tcatttacac ggaaatacat acggccatgc tattaacttt     1320
ttacgtgtag ataaacataa ccctaatgcg cctgtt                               1356
```

<210> SEQ ID NO 54
<211> LENGTH: 1356
<212> TYPE: DNA
<213> ORGANISM: Artificial Sequence
<220> FEATURE:
<223> OTHER INFORMATION: GAS40variant10

<400> SEQUENCE: 54

```
gatgatagag cctcaggaga acgaaggcg agtaatactc acgacgatag tttaccaaaa        60
ccagaaacaa ttcaagaggc aaaggcaact attgatgcag ttgaaaaaac tctcagtcaa      120
caaaaagcag aactgacaga gcttgctacc gctctgacaa aaactactgc tgaaatcaac      180
cacttaaaag agcagcaaga taatgaacaa aaagctttaa cctctgcaca agaaatttac      240
actaatactc ttgcaagtag tgaggagacg ctattagccc aaggagccga acatcaaaga      300
gagttaacag ctactgaaac agagcttcat aatgctcaag tagatcaaca ttcaaaagag      360
actgcattgt cagaacaaaa agctagcatt tcagcagaaa ctactcgagc tcaagattta      420
gtggaacaag tcaaaacgtc tgaacaaaat attgctaagc tcaatgctat gattagcaat      480
cctgatgcta tcactaaagc agctcaaacg gctaatgata tacaaaagc attaagctca      540 gaattggaga aggctaaagc tgacttagaa aatcaaaaag ctaaagttaa aaagcaattg      600
actgaagagt tggcagctca gaaagctgct ctagcagaaa aagaggcaga acttagtcgt      660
cttaaatcct cagctccgtc tactcaagat agcattgtgg gtaataatac catgaaagca      720
ccgcaaggct atcctcttga agaacttaaa aaattagaag ctagtggtta tattggatca      780
gctagttaca ataattatta caaagagcat gcagatcaaa ttattgccaa agctagtcca      840
ggtaatcaat taaatcaata ccaagatatt ccagcagatc gtaatcgctt tgttgatccc      900
gataatttga caccagaagt gcaaaatgag ctagcgcagt ttgcagctca catgattaat      960
agtgtaagaa gacaattagg tctaccacca gttactgtta cagcaggatc acaagaattt     1020
gcaagattac ttagtaccag ctataagaag actcatggta atacaagacc atcatttgtc     1080
tacggacagc caggggtatc agggcattat ggtgttgggc ctcatgataa aactattatt     1140
gaagactctg ccggagcgtc agggctcatt cgaaatgatg ataacatgta cgagaatatc     1200
ggtgctttta acgatgtgca tactgtgaat ggtattaaac gtggtattta tgacagtatc     1260
```

| aagtatatgc tctttacaga tcatttacac ggaaatacat acggccatgc tattaacttt | 1320 |
| ttacgtgtag ataaacgtaa ccctaatgcg cctgtt | 1356 |

<210> SEQ ID NO 55
<211> LENGTH: 1356
<212> TYPE: DNA
<213> ORGANISM: Artificial Sequence
<220> FEATURE:
<223> OTHER INFORMATION: GAS40variant11

<400> SEQUENCE: 55

| gatgatagag cctcaggaga aacgaaggcg agtaatactc acgacgatag tttaccaaaa | 60 |
| ccagaaacaa ttcaagaggc aaaggcaact attgatgcag ttgaaaaaac tctcagtcaa | 120 |
| caaaaagcag aactgacaga gcttgctacc gctctgacaa aaactactgc tgaaatcaac | 180 |
| cacttaaaag agcagcaaga taatgaacaa aaagctttaa cctctgcaca agaaatttac | 240 |
| actaatactc ttgcaagtag tgaggagacg ctattagccc aaggagccga acatcaaaga | 300 |
| gagttaacag ctactgaaac agagcttcat aatgctcaag cagatcaaca ttcaaaagag | 360 |
| actgcattgt cagaacaaaa agctagcatt tcagcagaaa ctactcgagc tcaagattta | 420 |
| gtggaacaag tcaaaacgtc tgaacaaaat attgctaagc tcaatgctat gattagcaat | 480 |
| cctgatgcta tcactaaagc agctcaaacg gctaatgata atacaaaagc attaagctca | 540 |
| gaattggaga aggctaaagc tgacttagaa aatcaaaaag ctaaagttaa aaagcaattg | 600 |
| actgaagagt tggcagctca gaaagctgct ctagcagaaa aagaggcaga acttagtcgt | 660 |
| cttaaatcct cagctccgtc tactcaagat agcattgtgg gtaataatac catgaaagca | 720 |
| ccgcaaggct atcctcttga agaacttaaa aaattagaag ctagtggtta tattggatca | 780 |
| gctagttaca ataattatta caaagagcat gcagatcaaa ttattgccaa agctagtcca | 840 |
| ggtaatcaat taaatcaata ccaagatatt ccagcagatc gtaatcgctt tgttgatccc | 900 |
| gataatttga caccagaagt gcaaaatgag ctagcgcagt ttgcagctca catgattaat | 960 |
| agtgtaagga gacaattagg tctaccacca gttactgtta cagcaggatc acaagaattt | 1020 |
| gcaagattac ttagtaccag ctataagaaa actcatggta atacaagacc atcatttgtc | 1080 |
| tacggacaac caggggtatc agggcattat ggtgttgggc tcatgataaa aactattatt | 1140 |
| gaagactctg ccggagcgtc agggctcatt cgaaatgatg ataacatgta cgagaatatc | 1200 |
| ggtgctttta acgatgtgca tactgtgaat ggtattaaac gtggtattta tgacagtatc | 1260 |
| aagtatatgc tctttacaga tcatttacac ggaaatacat atggccatgc tattaacttt | 1320 |
| ttacgtgtag ataaacgtaa ccctaatgcg cctgtt | 1356 |

<210> SEQ ID NO 56
<211> LENGTH: 1356
<212> TYPE: DNA
<213> ORGANISM: Artificial Sequence
<220> FEATURE:
<223> OTHER INFORMATION: GAS40variant12

<400> SEQUENCE: 56

| gatgatagag cctcaggaga aacgaaggcg agtaatactc acgacgatag tttaccaaaa | 60 |
| ccagaaacaa ttcaagaggc aaaggcaact attgaagcag ttgaaaaaac tctcagtcaa | 120 |
| caaaaagcag aactgacaga gcttgctacc gctctgacaa aaactactgc tgaaatcaac | 180 |
| cacttaaaag agcagcaaga taacgaacaa aaagctttaa cctctgcaca agaaatttac | 240 |
| actaatactc ttgcaagtag tgaggagacg ctattagccc aaggagccga acatcaaaga | 300 |

```
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa agaggcaga acttagtcgt    660 cttaaatcct cagctccgtc tactcaagat agcattgtgg gtaataatac catgaaagca    720
ccgcaaggct atcctcttga agaacttaaa aaattagaag ctagtggtta tattggatca    780
gctagttaca ataattatta caaagagcat gcagatcaaa ttattgccaa agctagtcca    840
ggtaatcaat taaatcaata ccaagatatt ccagcagatc gtaatcgctt tgttgatccc    900
gataatttga caccagaagt gcaaaatgag ctagcgcagt ttgcagctca catgattaat    960
agtgtaagaa gacaattagg tctaccacca gttactgtca cagcaggatc acaagaattt   1020
gcaagattac ttagtaccag ctataagaaa actcatggta atacaagacc atcatttgtc   1080 tacgacagc caggggtatc agggcattat ggtgttgggc ctcatgataa aactattatt   1140
gaagactctg ccggagcgtc agggctcatt cgaaatgatg ataacatgta cgagaatatc   1200
ggtgctttta cgatgtgca tactgtgaat ggtattaaac gtggtattta tgacagtatc   1260
aagtatatgc tctttacaga tcatttacac ggaaatacat atggccatgc tattaacttt   1320
ttacgtgtag ataaacgtaa ccctaatgcg cctgtt                             1356

<210> SEQ ID NO 57
<211> LENGTH: 1356
<212> TYPE: DNA
<213> ORGANISM: Artificial Sequence
<220> FEATURE:
<223> OTHER INFORMATION: GAS40variant13

<400> SEQUENCE: 57
gatgatagag cctcaggaga aacgaaggcg agtaatactc acgacgatag tttaccaaaa     60
ccagaaacaa ttcaagaggc aaaggcaact attgatgcag ttgaaaaaac tctcagtcaa    120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa agaggcaga acttagtcgt    660 cttaaatcct cagctccgtc tactcaagat agcattgtgg gtaataatac catgaaagca    720
ccgcaaggct atcctcttga agaacttaaa aaattagaag ctagtggtta tattggatca    780
gctagttaca ataattatta caaagagcat gcagatcaaa ttattgccaa agctagtcca    840
ggtaatcaat taaatcaata ccaagatatt ccagcagatc gtaatcgctt tgttgatccc    900
gataatttga caccagaagt gcaaaatgag ctagcgcagt ttgcagctca catgattaat    960
```

-continued

```
agtgtaagaa gacaattagg tctaccacca gttactgtta cagcaggatc acaagaattt   1020
gcaagattac ttagtaccag ctataagaaa actcatggta atacaagacc atcatttgtc   1080
tacggacagc cagggtatc agggcattat ggtgttgggc ctcatgataa aactattatt   1140
gaagactctg ccggagcgtc agggctcatt cgaaatgatg ataacatgta cgagaatatc   1200
ggtgctttta acgatgtgca tactgtgaat ggtattaaac gtggtattta tgacagtatc   1260
aagtatatgc tctttacaga tcatttacac ggaaatacat acggccatgc tattaacttt   1320
ttacgtgtag ataaacataa ccctaatgcg cctgtt                              1356
```

<210> SEQ ID NO 58
<211> LENGTH: 452
<212> TYPE: PRT
<213> ORGANISM: Artificial Sequence
<220> FEATURE:
<223> OTHER INFORMATION: GAS40VariantA

<400> SEQUENCE: 58

```
Asp Asp Arg Ala Ser Gly Glu Thr Lys Ala Ser Asn Thr His Asp Asp
  1               5                  10                  15

Ser Leu Pro Lys Pro Glu Thr Ile Gln Glu Ala Lys Ala Thr Ile Asp
             20                  25                  30

Ala Val Glu Lys Thr Leu Ser Gln Gln Lys Ala Glu Leu Thr Glu Leu
         35                  40                  45

Ala Thr Ala Leu Thr Lys Thr Thr Ala Glu Ile Asn His Leu Lys Glu
     50                  55                  60

Gln Gln Asp Asn Glu Gln Lys Ala Leu Thr Ser Ala Gln Glu Ile Tyr
 65                  70                  75                  80

Thr Asn Thr Leu Ala Ser Ser Glu Glu Thr Leu Leu Ala Gln Gly Ala
                 85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
```

```
              290                 295                 300
Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
                340                 345                 350

Gly Asn Thr Arg Pro Ser Phe Val Tyr Gly Gln Pro Gly Val Ser Gly
                355                 360                 365

His Tyr Gly Val Gly Pro His Asp Lys Thr Ile Ile Glu Asp Ser Ala
                370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
                420                 425                 430

Thr Tyr Gly His Ala Ile Asn Phe Leu Arg Val Asp Lys His Asn Pro
                435                 440                 445

Asn Ala Pro Val
    450

<210> SEQ ID NO 59
<211> LENGTH: 452
<212> TYPE: PRT
<213> ORGANISM: Artificial Sequence
<220> FEATURE:
<223> OTHER INFORMATION: GAS40VariantB

<400> SEQUENCE: 59

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
                20                  25                  30

Ala Val Glu Lys Thr Leu Ser Gln Gln Lys Ala Glu Leu Thr Glu Leu
            35                  40                  45

Ala Thr Ala Leu Thr Lys Thr Thr Ala Glu Ile Asn Asn Leu Lys Glu
50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
                100                 105                 110

Gln Ala Asp Gln His Ser Lys Glu Thr Ala Leu Ser Glu Gln Lys Ala
            115                 120                 125

Ser Ile Ser Ala Glu Thr Thr Arg Ala Gln Asp Leu Val Glu Gln Val
130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
```

```
            195                 200                 205
Ala Ala Leu Ala Glu Lys Glu Ala Glu Leu Ser Arg Leu Lys Ser Ser
210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
                260                 265                 270

Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
        290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
                340                 345                 350

Gly Asn Thr Arg Pro Ser Phe Val Tyr Gly Gln Pro Gly Val Ser Gly
            355                 360                 365

His Tyr Gly Val Gly Pro His Asp Lys Thr Ile Ile Glu Asp Ser Ala
        370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
                420                 425                 430

Thr Tyr Gly His Ala Ile Asn Phe Leu Arg Val Asp Lys Arg Asn Pro
            435                 440                 445

Asn Ala Pro Val
    450

<210> SEQ ID NO 60
<211> LENGTH: 452
<212> TYPE: PRT
<213> ORGANISM: Artificial Sequence
<220> FEATURE:
<223> OTHER INFORMATION: GAS40VariantC

<400> SEQUENCE: 60

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
                20                  25                  30

Ala Val Glu Lys Thr Leu Ser Gln Gln Lys Ala Glu Leu Thr Glu Leu
            35                  40                  45

Ala Thr Ala Leu Thr Lys Thr Thr Ala Glu Ile Asn His Leu Lys Glu
        50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
```

```
            100                 105                 110
Gln Ala Asp Gln His Ser Lys Glu Thr Ala Leu Ser Glu Gln Lys Ala
            115                 120                 125
Ser Ile Ser Ala Glu Thr Thr Arg Ala Gln Asp Leu Val Glu Gln Val
        130                 135                 140
Lys Thr Ser Glu Gln Asn Ile Ala Lys Leu Asn Ala Met Ile Ser Asn
145                 150                 155                 160
Pro Asp Ala Ile Thr Lys Ala Ala Gln Thr Ala Asn Asp Asn Thr Lys
                165                 170                 175
Ala Leu Ser Ser Glu Leu Glu Lys Ala Lys Ala Asp Leu Glu Asn Gln
            180                 185                 190
Lys Ala Lys Val Lys Gln Leu Thr Glu Glu Leu Ala Ala Gln Lys
        195                 200                 205
Ala Ala Leu Ala Glu Lys Glu Ala Glu Leu Ser Arg Leu Lys Ser Ser
        210                 215                 220
Ala Pro Ser Thr Gln Asp Ser Ile Val Gly Asn Asn Thr Met Lys Ala
225                 230                 235                 240
Pro Gln Gly Tyr Pro Leu Glu Glu Leu Lys Lys Leu Glu Ala Ser Gly
                245                 250                 255
Tyr Ile Gly Ser Ala Ser Tyr Asn Asn Tyr Tyr Lys Glu His Ala Asp
            260                 265                 270
Gln Ile Ile Ala Lys Ala Ser Pro Gly Asn Gln Leu Asn Gln Tyr Gln
        275                 280                 285
Asp Ile Pro Ala Asp Arg Asn Arg Phe Val Asp Pro Asp Asn Leu Thr
        290                 295                 300
Pro Glu Val Gln Asn Glu Leu Ala Gln Phe Ala Ala His Met Ile Asn
305                 310                 315                 320
Ser Val Arg Arg Gln Leu Gly Leu Pro Pro Val Thr Val Thr Ala Gly
                325                 330                 335
Ser Gln Glu Phe Ala Arg Leu Leu Ser Thr Ser Tyr Lys Lys Thr His
            340                 345                 350
Gly Asn Thr Arg Pro Ser Phe Val Tyr Gly Gln Pro Gly Val Ser Gly
        355                 360                 365
His Tyr Gly Val Gly Pro His Asp Lys Thr Ile Ile Glu Asp Ser Ala
    370                 375                 380
Gly Ala Ser Gly Leu Ile Arg Asn Asp Asp Asn Met Tyr Glu Asn Ile
385                 390                 395                 400
Gly Ala Phe Asn Asp Val His Thr Val Asn Gly Ile Lys Arg Gly Ile
                405                 410                 415
Tyr Asp Ser Ile Lys Tyr Met Leu Phe Thr Asp His Leu His Gly Asn
            420                 425                 430
Thr Tyr Gly His Ala Ile Asn Phe Leu Arg Val Asp Lys His Asn Pro
        435                 440                 445
Lys Ala Pro Val
    450

<210> SEQ ID NO 61
<211> LENGTH: 452
<212> TYPE: PRT
<213> ORGANISM: Artificial Sequence
<220> FEATURE:
<223> OTHER INFORMATION: GAS40VariantD

<400> SEQUENCE: 61

Asp Asp Arg Ala Ser Gly Glu Thr Lys Ala Ser Asn Thr His Asp Asp
```

-continued

```
1               5                   10                  15
Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Lys Leu
            35                  40                  45

Ala Thr Ala Leu Thr Lys Thr Thr Ala Glu Ile Asn His Leu Lys Glu
            50                  55                  60

Gln Gln Asp Asn Glu Gln Lys Ala Leu Thr Ser Ala Gln Glu Ile Tyr
65                      70                  75                  80

Thr Asn Thr Leu Ala Ser Ser Glu Glu Thr Leu Leu Ala Gln Gly Ala
                    85                  90                  95

Glu His Gln Arg Glu Leu Thr Ala Thr Glu Thr Leu His Asn Ala
                    100                 105                 110

Gln Ala Asp Gln His Ser Lys Glu Thr Ala Leu Ser Glu Gln Lys Ala
                    115                 120                 125

Ser Ile Ser Ala Glu Thr Thr Arg Ala Gln Asp Leu Val Glu Gln Val
            130                 135                 140

Lys Thr Ser Glu Gln Asn Ile Ala Lys Leu Asn Ala Met Ile Ser Asn
145                     150                 155                 160

Pro Asp Ala Ile Thr Lys Ala Ala Gln Thr Ala Asn Asp Asn Thr Lys
                    165                 170                 175

Ala Leu Ser Ser Glu Leu Glu Lys Ala Lys Ala Asp Leu Glu Asn Gln
                    180                 185                 190

Lys Ala Lys Val Lys Lys Gln Leu Thr Glu Glu Leu Ala Ala Gln Lys
                    195                 200                 205

Ala Ala Leu Ala Glu Lys Glu Ala Glu Leu Ser Arg Leu Lys Ser Ser
            210                 215                 220

Ala Pro Ser Thr Gln Asp Ser Ile Val Gly Asn Asn Thr Met Lys Ala
225                     230                 235                 240

Pro Gln Gly Tyr Pro Leu Glu Glu Leu Lys Lys Leu Glu Ala Ser Gly
                    245                 250                 255

Tyr Ile Gly Ser Ala Ser Tyr Asn Asn Tyr Lys Glu His Ala Asp
                    260                 265                 270

Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
            290                 295                 300

Pro Glu Val Gln Asn Glu Leu Ala Gln Phe Ala Ala His Met Ile Asn
305                     310                 315                 320

Ser Val Arg Arg Gln Leu Gly Leu Pro Pro Val Thr Val Thr Ala Gly
                    325                 330                 335

Ser Gln Glu Phe Ala Arg Leu Leu Ser Thr Ser Tyr Lys Lys Thr His
                    340                 345                 350

Gly Asn Thr Arg Pro Ser Phe Val Tyr Gly Gln Pro Gly Val Ser Gly
                    355                 360                 365

His Tyr Gly Val Gly Pro His Asp Lys Thr Ile Ile Glu Asp Ser Ala
            370                 375                 380

Gly Ala Ser Gly Leu Ile Arg Asn Asp Asp Asn Met Tyr Glu Asn Ile
385                     390                 395                 400

Gly Ala Phe Asn Asp Val His Thr Val Asn Gly Ile Lys Arg Gly Ile
                    405                 410                 415

Tyr Asp Ser Ile Lys Tyr Met Leu Phe Thr Asp His Leu His Gly Asn
                    420                 425                 430
```

-continued

Thr Tyr Gly His Ala Ile Asn Phe Leu Arg Val Asp Lys Arg Asn Pro
            435                 440                 445

Asn Ala Pro Val
    450

<210> SEQ ID NO 62
<211> LENGTH: 452
<212> TYPE: PRT
<213> ORGANISM: Artificial Sequence
<220> FEATURE:
<223> OTHER INFORMATION: GAS40VariantE

<400> SEQUENCE: 62

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
            20                  25                  30

Ala Val Glu Lys Ala Leu Ser Gln Gln Lys Ala Glu Leu Thr Glu Leu
        35                  40                  45

Ala Thr Ala Leu Thr Lys Thr Thr Ala Lys Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

```
Ser Gln Glu Phe Ala Arg Leu Leu Ser Thr Ser Tyr Lys Lys Thr His
                340                 345                 350

Gly Asn Thr Arg Pro Ser Phe Val Tyr Gly Gln Pro Gly Val Ser Gly
            355                 360                 365

His Tyr Gly Val Gly Pro His Asp Lys Thr Ile Ile Glu Asp Ser Ala
370                 375                 380

Gly Ala Ser Gly Leu Ile Arg Asn Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450

<210> SEQ ID NO 63
<211> LENGTH: 452
<212> TYPE: PRT
<213> ORGANISM: Artificial Sequence
<220> FEATURE:
<223> OTHER INFORMATION: GAS40VariantF

<400> SEQUENCE: 63

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
                20                  25                  30

Ala Val Glu Lys Ala Leu Ser Gln Gln Lys Ala Glu Leu Thr Glu Leu
            35                  40                  45

Ala Thr Ala Leu Thr Lys Thr Thr Ala Lys Ile Asn His Leu Lys Glu
        50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240
```

```
Pro Gln Gly Tyr Pro Leu Glu Leu Lys Lys Leu Glu Ala Ser Gly
            245                 250                 255

Tyr Ile Gly Ser Ala Ser Tyr Asn Asn Tyr Tyr Lys Glu His Ala Asp
        260                 265                 270

Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450

<210> SEQ ID NO 64
<211> LENGTH: 452
<212> TYPE: PRT
<213> ORGANISM: Artificial Sequence
<220> FEATURE:
<223> OTHER INFORMATION: GAS40VariantG

<400> SEQUENCE: 64

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Gly Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140
```

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
            290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450

<210> SEQ ID NO 65
<211> LENGTH: 452
<212> TYPE: PRT
<213> ORGANISM: Artificial Sequence
<220> FEATURE:
<223> OTHER INFORMATION: GAS40VariantH

<400> SEQUENCE: 65

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

-continued

```
Ala Thr Ala Leu Thr Lys Thr Ala Glu Ile Asn His Leu Lys Glu
 50                  55                  60

Gln Gln Asp Asn Glu Gln Lys Ala Leu Thr Ser Ala Gln Glu Ile Tyr
 65                  70                  75                  80

Thr Asn Thr Leu Ala Ser Ser Glu Glu Thr Leu Leu Ala Gln Gly Ala
                 85                  90                  95

Glu His Gln Arg Glu Leu Thr Ala Thr Glu Thr Glu Leu His Asn Ala
                100                 105                 110

Gln Ala Asp Gln His Ser Lys Glu Thr Ala Leu Ser Glu Gln Lys Ala
            115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
                180                 185                 190

Lys Ala Lys Val Lys Lys Gln Leu Thr Glu Glu Leu Ala Ala Gln Lys
            195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
                260                 265                 270

Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
                340                 345                 350

Gly Asn Thr Arg Pro Ser Phe Val Tyr Gly Gln Pro Gly Val Ser Gly
            355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
                420                 425                 430

Thr Tyr Gly His Ala Ile Asn Phe Leu Arg Val Asp Lys His Asn Pro
            435                 440                 445

Asn Ala Pro Val
450
```

<210> SEQ ID NO 66
<211> LENGTH: 452
<212> TYPE: PRT
<213> ORGANISM: Artificial Sequence
<220> FEATURE:
<223> OTHER INFORMATION: GAS40VariantI

<400> SEQUENCE: 66

```
Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Thr Leu Leu Ala Gln Gly Ala
                    85                  90                  95

Glu His Gln Arg Glu Leu Thr Ala Thr Glu Thr Glu Leu His Asn Ala
            100                 105                 110

Gln Val Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365
```

His Tyr Gly Val Gly Pro His Asp Lys Thr Ile Ile Glu Asp Ser Ala
    370                 375                 380

Gly Ala Ser Gly Leu Ile Arg Asn Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
                420                 425                 430

Thr Tyr Gly His Ala Ile Asn Phe Leu Arg Val Asp Lys Arg Asn Pro
            435                 440                 445

Asn Ala Pro Val
    450

<210> SEQ ID NO 67
<211> LENGTH: 452
<212> TYPE: PRT
<213> ORGANISM: Artificial Sequence
<220> FEATURE:
<223> OTHER INFORMATION: GAS40VariantJ

<400> SEQUENCE: 67

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
                20                  25                  30

Ala Val Glu Lys Thr Leu Ser Gln Gln Lys Ala Glu Leu Thr Glu Leu
            35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65              70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Gly Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

```
Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
            325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
            355                 360                 365

His Tyr Gly Val Gly Pro His Asp Lys Thr Ile Ile Glu Asp Ser Ala
            370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
            435                 440                 445

Asn Ala Pro Val
    450

<210> SEQ ID NO 68
<211> LENGTH: 452
<212> TYPE: PRT
<213> ORGANISM: Artificial Sequence
<220> FEATURE:
<223> OTHER INFORMATION: GAS40VariantK

<400> SEQUENCE: 68

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175
```

```
Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
            275                 280                 285

Asp Ile Pro Ala Asp Arg Asn Arg Phe Val Asp Pro Asp Asn Leu Thr
            290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
                340                 345                 350

Gly Asn Thr Arg Pro Ser Phe Val Tyr Gly Gln Pro Gly Val Ser Gly
            355                 360                 365

His Tyr Gly Val Gly Pro His Asp Lys Thr Ile Ile Glu Asp Ser Ala
            370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
            435                 440                 445

Asn Ala Pro Val
450

<210> SEQ ID NO 69
<211> LENGTH: 872
<212> TYPE: PRT
<213> ORGANISM: Artificial Sequence
<220> FEATURE:
<223> OTHER INFORMATION: GAS40variantAA

<400> SEQUENCE: 69

Met Asp Leu Glu Gln Thr Lys Pro Asn Gln Val Lys Gln Lys Ile Ala
1               5                   10                  15

Leu Thr Ser Thr Ile Ala Leu Leu Ser Ala Ser Val Gly Val Ser His
            20                  25                  30

Gln Val Lys Ala Asp Asp Arg Ala Ser Gly Glu Thr Lys Ala Ser Asn
        35                  40                  45

Thr His Asp Asp Ser Leu Pro Lys Pro Glu Thr Ile Gln Glu Ala Lys
    50                  55                  60

Ala Thr Ile Asp Ala Val Glu Lys Thr Leu Ser Gln Gln Lys Ala Glu
65                  70                  75                  80
```

-continued

```
Leu Thr Glu Leu Ala Thr Ala Leu Thr Lys Thr Thr Ala Glu Ile Asn
            85                  90                  95

His Leu Lys Glu Gln Gln Asp Asn Glu Gln Lys Ala Leu Thr Ser Ala
        100                 105                 110

Gln Glu Ile Tyr Thr Asn Thr Leu Ala Ser Ser Glu Glu Thr Leu Leu
        115                 120                 125

Ala Gln Gly Ala Glu His Gln Arg Glu Leu Thr Ala Thr Glu Thr Glu
    130                 135                 140

Leu His Asn Ala Gln Ala Asp Gln His Ser Lys Glu Thr Ala Leu Ser
145                 150                 155                 160

Glu Gln Lys Ala Ser Ile Ser Ala Glu Thr Thr Arg Ala Gln Asp Leu
                165                 170                 175

Val Glu Gln Val Lys Thr Ser Glu Gln Asn Ile Ala Lys Leu Asn Ala
            180                 185                 190

Met Ile Ser Asn Pro Asp Ala Ile Thr Lys Ala Ala Gln Thr Ala Asn
        195                 200                 205

Asp Asn Thr Lys Ala Leu Ser Ser Glu Leu Glu Lys Ala Lys Ala Asp
    210                 215                 220

Leu Glu Asn Gln Lys Ala Lys Val Lys Lys Gln Leu Thr Glu Glu Leu
225                 230                 235                 240

Ala Ala Gln Lys Ala Ala Leu Ala Glu Lys Glu Ala Glu Leu Ser Arg
                245                 250                 255

Leu Lys Ser Ser Ala Pro Ser Thr Gln Asp Ser Ile Val Gly Asn Asn
            260                 265                 270

Thr Met Lys Ala Pro Gln Gly Tyr Pro Leu Glu Glu Leu Lys Lys Leu
        275                 280                 285

Glu Ala Ser Gly Tyr Ile Gly Ser Ala Ser Tyr Asn Asn Tyr Tyr Lys
    290                 295                 300

Glu His Ala Asp Gln Ile Ile Ala Lys Ala Ser Pro Gly Asn Gln Leu
305                 310                 315                 320

Asn Gln Tyr Gln Asp Ile Pro Ala Asp Arg Asn Arg Phe Val Asp Pro
                325                 330                 335

Asp Asn Leu Thr Pro Glu Val Gln Asn Glu Leu Ala Gln Phe Ala Ala
            340                 345                 350

His Met Ile Asn Ser Val Arg Arg Gln Leu Gly Leu Pro Pro Val Thr
        355                 360                 365

Val Thr Ala Gly Ser Gln Glu Phe Ala Arg Leu Leu Ser Thr Ser Tyr
    370                 375                 380

Lys Lys Thr His Gly Asn Thr Arg Pro Ser Phe Val Tyr Gly Gln Pro
385                 390                 395                 400

Gly Val Ser Gly His Tyr Gly Val Gly Pro His Asp Lys Thr Ile Ile
                405                 410                 415

Glu Asp Ser Ala Gly Ala Ser Gly Leu Ile Arg Asn Asp Asp Asn Met
            420                 425                 430

Tyr Glu Asn Ile Gly Ala Phe Asn Asp Val His Thr Val Asn Gly Ile
        435                 440                 445

Lys Arg Gly Ile Tyr Asp Ser Ile Lys Tyr Met Leu Phe Thr Asp His
    450                 455                 460

Leu His Gly Asn Thr Tyr Gly His Ala Ile Asn Phe Leu Arg Val Asp
465                 470                 475                 480

Lys His Asn Pro Asn Ala Pro Val Tyr Leu Gly Phe Ser Thr Ser Asn
                485                 490                 495

Val Gly Ser Leu Asn Glu His Phe Val Met Phe Pro Glu Ser Asn Ile
```

```
                500                 505                 510
Ala Asn His Gln Arg Phe Asn Lys Thr Pro Ile Lys Ala Val Gly Ser
            515                 520                 525

Thr Lys Asp Tyr Ala Gln Arg Val Gly Thr Val Ser Asp Thr Ile Ala
530                 535                 540

Ala Ile Lys Gly Lys Val Ser Ser Leu Glu Asn Arg Leu Ser Ala Ile
545                 550                 555                 560

His Gln Glu Ala Asp Ile Met Ala Ala Gln Ala Lys Val Ser Gln Leu
                565                 570                 575

Gln Gly Lys Leu Ala Ser Thr Leu Lys Gln Ser Asp Ser Leu Asn Leu
            580                 585                 590

Gln Val Arg Gln Leu Asn Asp Thr Lys Gly Ser Leu Arg Thr Glu Leu
        595                 600                 605

Leu Ala Ala Lys Ala Lys Gln Ala Gln Leu Glu Ala Thr Arg Asp Gln
    610                 615                 620

Ser Leu Ala Lys Leu Ala Ser Leu Lys Ala Ala Leu His Gln Thr Glu
625                 630                 635                 640

Ala Leu Ala Glu Gln Ala Ala Ala Arg Val Thr Ala Leu Val Ala Lys
                645                 650                 655

Lys Ala His Leu Gln Tyr Leu Arg Asp Phe Lys Leu Asn Pro Asn Arg
            660                 665                 670

Leu Gln Val Ile Arg Glu Arg Ile Asp Asn Thr Lys Gln Asp Leu Ala
        675                 680                 685

Lys Thr Thr Ser Ser Leu Leu Asn Ala Gln Glu Ala Leu Ala Ala Leu
    690                 695                 700

Gln Ala Lys Gln Ser Ser Leu Glu Ala Thr Ile Ala Thr Thr Glu His
705                 710                 715                 720

Gln Leu Thr Leu Leu Lys Thr Leu Ala Asn Glu Lys Glu Tyr Arg His
                725                 730                 735

Leu Asp Glu Asp Ile Ala Thr Val Pro Asp Leu Gln Val Ala Pro Pro
            740                 745                 750

Leu Thr Gly Val Lys Pro Leu Ser Tyr Ser Lys Ile Asp Thr Thr Pro
        755                 760                 765

Leu Val Gln Glu Met Val Lys Glu Thr Lys Gln Leu Leu Glu Ala Ser
    770                 775                 780

Ala Arg Leu Ala Ala Glu Asn Thr Ser Leu Val Ala Glu Ala Leu Val
785                 790                 795                 800

Gly Gln Thr Ser Glu Met Val Ala Ser Asn Ala Ile Val Ser Lys Ile
                805                 810                 815

Thr Ser Ser Ile Thr Gln Pro Ser Ser Lys Thr Ser Tyr Gly Ser Gly
            820                 825                 830

Ser Ser Thr Thr Ser Asn Leu Ile Ser Asp Val Asp Glu Ser Thr Gln
        835                 840                 845

Arg Ala Leu Lys Ala Gly Trp Met Leu Ala Ala Val Gly Leu Thr Gly
    850                 855                 860

Phe Arg Phe Arg Lys Glu Ser Lys
865                 870

<210> SEQ ID NO 70
<211> LENGTH: 873
<212> TYPE: PRT
<213> ORGANISM: Artificial Sequence
<220> FEATURE:
<223> OTHER INFORMATION: WildTypeGAS40
```

```
<400> SEQUENCE: 70

Met Asp Leu Glu Gln Thr Lys Pro Asn Gln Val Lys Gln Lys Ile Ala
1               5                   10                  15

Leu Thr Ser Thr Ile Ala Leu Leu Ser Ala Ser Val Gly Val Ser His
            20                  25                  30

Gln Val Lys Ala Asp Asp Arg Ala Ser Gly Glu Thr Lys Ala Ser Asn
        35                  40                  45

Thr His Asp Asp Ser Leu Pro Lys Pro Glu Thr Ile Gln Glu Ala Lys
    50                  55                  60

Ala Thr Ile Asp Ala Val Glu Lys Thr Leu Ser Gln Gln Lys Ala Glu
65                  70                  75                  80

Leu Thr Glu Leu Ala Thr Ala Leu Thr Lys Thr Thr Ala Glu Ile Asn
                85                  90                  95

His Leu Lys Glu Gln Gln Asp Asn Glu Gln Lys Ala Leu Thr Ser Ala
            100                 105                 110

Gln Glu Ile Tyr Thr Asn Thr Leu Ala Ser Ser Glu Glu Thr Leu Leu
        115                 120                 125

Ala Gln Gly Ala Glu His Gln Arg Glu Leu Thr Ala Thr Glu Thr Glu
    130                 135                 140

Leu His Asn Ala Gln Ala Asp Gln His Ser Lys Glu Thr Ala Leu Ser
145                 150                 155                 160

Glu Gln Lys Ala Ser Ile Ser Ala Glu Thr Thr Arg Ala Gln Asp Leu
                165                 170                 175

Val Glu Gln Val Lys Thr Ser Glu Gln Asn Ile Ala Lys Leu Asn Ala
            180                 185                 190

Met Ile Ser Asn Pro Asp Ala Ile Thr Lys Ala Ala Gln Thr Ala Asn
        195                 200                 205

Asp Asn Thr Lys Ala Leu Ser Ser Glu Leu Glu Lys Ala Lys Ala Asp
    210                 215                 220

Leu Glu Asn Gln Lys Ala Lys Val Lys Lys Gln Leu Thr Glu Glu Leu
225                 230                 235                 240

Ala Ala Gln Lys Ala Ala Leu Ala Glu Lys Glu Ala Glu Leu Ser Arg
                245                 250                 255

Leu Lys Ser Ser Ala Pro Ser Thr Gln Asp Ser Ile Val Gly Asn Asn
            260                 265                 270

Thr Met Lys Ala Pro Gln Gly Tyr Pro Leu Glu Glu Leu Lys Lys Leu
        275                 280                 285

Glu Ala Ser Gly Tyr Ile Gly Ser Ala Ser Tyr Asn Asn Tyr Tyr Lys
    290                 295                 300

Glu His Ala Asp Gln Ile Ile Ala Lys Ala Ser Pro Gly Asn Gln Leu
305                 310                 315                 320

Asn Gln Tyr Gln Asp Ile Pro Ala Asp Arg Asn Arg Phe Val Asp Pro
                325                 330                 335

Asp Asn Leu Thr Pro Glu Val Gln Asn Glu Leu Ala Gln Phe Ala Ala
            340                 345                 350

His Met Ile Asn Ser Val Arg Arg Gln Leu Gly Leu Pro Pro Val Thr
        355                 360                 365

Val Thr Ala Gly Ser Gln Glu Phe Ala Arg Leu Leu Ser Thr Ser Tyr
    370                 375                 380

Lys Lys Thr His Gly Asn Thr Arg Pro Ser Phe Val Tyr Gly Gln Pro
385                 390                 395                 400

Gly Val Ser Gly His Tyr Gly Val Gly Pro His Asp Lys Thr Ile Ile
                405                 410                 415
```

```
Glu Asp Ser Ala Gly Ala Ser Gly Leu Ile Arg Asn Asp Asn Met
                420                 425                 430

Tyr Glu Asn Ile Gly Ala Phe Asn Asp Val His Thr Val Asn Gly Ile
            435                 440                 445

Lys Arg Gly Ile Tyr Asp Ser Ile Lys Tyr Met Leu Phe Thr Asp His
450                 455                 460

Leu His Gly Asn Thr Tyr Gly His Ala Ile Asn Phe Leu Arg Val Asp
465                 470                 475                 480

Lys His Asn Pro Asn Ala Pro Val Tyr Leu Gly Phe Ser Thr Ser Asn
                485                 490                 495

Val Gly Ser Leu Asn Glu His Phe Val Met Phe Pro Glu Ser Asn Ile
                500                 505                 510

Ala Asn His Gln Arg Phe Asn Lys Thr Pro Ile Lys Ala Val Gly Ser
                515                 520                 525

Thr Lys Asp Tyr Ala Gln Arg Val Gly Thr Val Ser Asp Thr Ile Ala
                530                 535                 540

Ala Ile Lys Gly Lys Val Ser Ser Leu Glu Asn Arg Leu Ser Ala Ile
545                 550                 555                 560

His Gln Glu Ala Asp Ile Met Ala Ala Gln Ala Lys Val Ser Gln Leu
                565                 570                 575

Gln Gly Lys Leu Ala Ser Thr Leu Lys Gln Ser Asp Ser Leu Asn Leu
                580                 585                 590

Gln Val Arg Gln Leu Asn Asp Thr Lys Gly Ser Leu Arg Thr Glu Leu
                595                 600                 605

Leu Ala Ala Lys Ala Lys Gln Ala Gln Leu Glu Ala Thr Arg Asp Gln
                610                 615                 620

Ser Leu Ala Lys Leu Ala Ser Leu Lys Ala Ala Leu His Gln Thr Glu
625                 630                 635                 640

Ala Leu Ala Glu Gln Ala Ala Ala Arg Val Thr Ala Leu Val Ala Lys
                645                 650                 655

Lys Ala His Leu Gln Tyr Leu Arg Asp Phe Lys Leu Asn Pro Asn Arg
                660                 665                 670

Leu Gln Val Ile Arg Glu Arg Ile Asp Asn Thr Lys Gln Asp Leu Ala
                675                 680                 685

Lys Thr Thr Ser Ser Leu Leu Asn Ala Gln Glu Ala Leu Ala Ala Leu
690                 695                 700

Gln Ala Lys Gln Ser Ser Leu Glu Ala Thr Ile Ala Thr Thr Glu His
705                 710                 715                 720

Gln Leu Thr Leu Leu Lys Thr Leu Ala Asn Glu Lys Glu Tyr Arg His
                725                 730                 735

Leu Asp Glu Asp Ile Ala Thr Val Pro Asp Leu Gln Val Ala Pro Pro
                740                 745                 750

Leu Thr Gly Val Lys Pro Leu Ser Tyr Ser Lys Ile Asp Thr Thr Pro
                755                 760                 765

Leu Val Gln Glu Met Val Lys Glu Thr Lys Gln Leu Leu Glu Ala Ser
                770                 775                 780

Ala Arg Leu Ala Ala Glu Asn Thr Ser Leu Val Ala Glu Ala Leu Val
785                 790                 795                 800

Gly Gln Thr Ser Glu Met Val Ala Ser Asn Ala Ile Val Ser Lys Ile
                805                 810                 815

Thr Ser Ser Ile Thr Gln Pro Ser Ser Lys Thr Ser Tyr Gly Ser Gly
                820                 825                 830
```

```
Ser Ser Thr Thr Ser Asn Leu Ile Ser Asp Val Asp Glu Ser Thr Gln
        835                 840                 845

Arg Ala Leu Lys Ala Gly Val Val Met Leu Ala Ala Val Gly Leu Thr
    850                 855                 860

Gly Phe Arg Phe Arg Lys Glu Ser Lys
865                 870

<210> SEQ ID NO 71
<211> LENGTH: 2622
<212> TYPE: DNA
<213> ORGANISM: Artificial Sequence
<220> FEATURE:
<223> OTHER INFORMATION: GAS57Variant

<400> SEQUENCE: 71
atggacttag aacaaacgaa gccaaaccaa gttaagcaga aaattgcttt aacctcaaca      60
attgctttat tgagtgccag tgtaggcgta tctcaccaag tcaaagcaga tgatagagcc     120
tcaggagaaa cgaaggcgag taatactcac gacgatagtt taccaaaacc agaaacaatt     180
caagaggcaa aggcaactat tgatgcagtt gaaaaaactc tcagtcaaca aaaagcagaa     240
ctgacagagc ttgctaccgc tctgacaaaa actactgctg aaatcaacca cttaaaagag     300
cagcaagata tgaacaaaaa gctttaacc tctgcacaag aaatttacac taatactctt     360
gcaagtagtg aggagacgct attagcccaa ggagccgaac atcaaagaga gttaacagct     420
actgaaacag agcttcataa tgctcaagca gatcaacatt caaagagac tgcattgtca     480
gaacaaaaag ctagcatttc agcagaaact actcgagctc aagatttagt ggaacaagtc     540
aaaacgtctg aacaaaatat tgctaagctc aatgctatga ttagcaatcc tgatgctatc     600
actaaagcag ctcaaacggc taatgataat acaaaagcat taagctcaga attggagaag     660
gctaaagctg acttagaaaa tcaaaaagct aaagttaaaa agcaattgac tgaagagttg     720
gcagctcaga aagctgctct agcagaaaaa gaggcagaac ttagtcgtct taaatcctca     780
gctccgtcta ctcaagatag cattgtgggt aataatacca tgaaagcacc gcaaggctat     840
cctcttgaag aacttaaaaa attagaagct agtggttata ttggatcagc tagttacaat     900
aattattaca agagcatgc agatcaaatt attgccaaag ctagtccagg taatcaatta     960
aatcaatacc aagatattcc agcagatcgt aatcgctttg ttgatcccga taatttgaca    1020
ccagaagtgc aaaatgagct agcgcagttt gcagctcaca tgattaatag tgtaagaaga    1080
caattaggtc taccaccagt tactgttaca gcaggatcac aagaattgc aagattactt    1140
agtaccagct ataagaaaac tcatggtaat acaagaccat catttgtcta cggacagcca    1200
ggggtatcag gcattatgg tgttgggcct catgataaaa ctattattga agactctgcc    1260
ggagcgtcag gctcattcg aaatgatgat aacatgtacg agaatatcgg tgcttttaac    1320
gatgtgcata ctgtgaatgg tattaaacgt ggtatttatg acagtatcaa gtatatgctc    1380
tttacagatc atttcacgg aaatacatac ggccatgcta ttaacttttt acgtgtagat    1440
aaacataacc ctaatgcgcc tgtttacctt ggattttcaa ccagcaatgt aggatctttg    1500
aatgaacact ttgtaatgtt tccagagtct aacattgcta accatcaacg ctttaataag    1560
acccctataa aagccgttgg aagtacaaaa gattatgccc aaagagtagg cactgtatct    1620
gatactattg cagcgatcaa aggaaaagta agctcattag aaaatcgttt gtcggctatt    1680
catcaagaag ctgatattat ggcagcccaa gctaaagtaa gtcaacttca aggtaaatta    1740
gcaagcacac ttaagcagtc agacagctta aatctccaag tgagacaatt aaatgatact    1800
```

```
aaaggttctt tgagaacaga attactagca gctaaagcaa aacaagcaca actcgaagct   1860
actcgtgatc aatcattagc taagctagca tcgttgaaag ccgcactgca ccagacagaa   1920
gccttagcag agcaagccgc agccagagtg acagcactgg tggctaaaaa agctcatttg   1980
caatatctaa gggactttaa attgaatcct aaccgccttc aagtgatacg tgagcgcatt   2040
gataatacta agcaagattt ggctaaaact acctcatctt tgttaaatgc acaagaagct   2100
ttagcagcct tacaagctaa acaaagcagt ctagaagcta ctattgctac cacagaacac   2160
cagttgactt tgcttaaaac cttagctaac gaaaaggaat atcgccactt agacgaagat   2220
atagctactg tgcctgattt gcaagtagct ccacctctta cgggcgtaaa accgctatca   2280
tatagtaaga tagatactac tccgcttgtt caagaaatgg ttaaagaaac gaaacaacta   2340
ttagaagctt cagcaagatt agctgctgaa aatacaagtc ttgtagcaga agcgcttgtt   2400
ggccaaacct ctgaaatggt agcaagtaat gccattgtgt ctaaaatcac atcttcgatt   2460
actcagccct catctaagac atcttatggc tcaggatctt ctacaacgag caatctcatt   2520
tctgatgttg atgaaagtac tcaaagagct cttaaagcag gagtcgtcat gttggcagct   2580
gtcggcctca caggatttag gttccgtaag gaatctaagt ga                      2622
```

<210> SEQ ID NO 72
<211> LENGTH: 410
<212> TYPE: PRT
<213> ORGANISM: Artificial Sequence
<220> FEATURE:
<223> OTHER INFORMATION: GAS57Variant

<400> SEQUENCE: 72

```
Met Ile Lys Arg Leu Ile Ser Leu Val Val Ile Ala Leu Phe Phe Ala
1               5                   10                  15

Ala Ser Thr Val Ser Gly Glu Glu Tyr Ser Val Thr Ala Lys His Ala
            20                  25                  30

Ile Ala Val Asp Leu Glu Ser Gly Lys Val Leu Tyr Glu Lys Asp Ala
        35                  40                  45

Lys Glu Val Val Pro Val Ala Ser Val Ser Lys Leu Leu Thr Thr Tyr
    50                  55                  60

Leu Val Tyr Lys Glu Val Ser Lys Gly Lys Leu Asn Trp Asp Ser Pro
65                  70                  75                  80

Val Thr Ile Ser Asn Tyr Pro Tyr Glu Leu Thr Thr Asn Tyr Thr Ile
                85                  90                  95

Ser Asn Val Pro Leu Asp Lys Arg Lys Tyr Thr Val Lys Glu Leu Leu
            100                 105                 110

Ser Ala Leu Val Val Asn Asn Ala Asn Ser Pro Ala Ile Ala Leu Ala
        115                 120                 125

Glu Lys Ile Gly Gly Thr Glu Pro Lys Phe Val Asp Lys Met Lys Lys
    130                 135                 140

Gln Leu Arg Gln Trp Gly Ile Ser Asp Ala Lys Val Val Asn Ser Thr
145                 150                 155                 160

Gly Leu Thr Asn His Phe Leu Gly Ala Asn Thr Tyr Pro Asn Thr Glu
                165                 170                 175

Pro Asp Asp Glu Asn Cys Phe Cys Ala Thr Asp Leu Ala Ile Ile Ala
            180                 185                 190

Arg His Leu Leu Leu Glu Phe Pro Glu Val Leu Lys Leu Ser Ser Lys
        195                 200                 205

Ser Ser Thr Ile Phe Ala Gly Gln Thr Ile Tyr Ser Tyr Asn Tyr Met
    210                 215                 220
```

Leu Lys Gly Met Pro Cys Tyr Arg Glu Gly Val Asp Gly Leu Phe Val
225                 230                 235                 240

Gly Tyr Ser Lys Lys Ala Gly Ala Ser Phe Val Ala Thr Ser Val Glu
            245                 250                 255

Asn Gln Met Arg Val Ile Thr Val Val Leu Asn Ala Asp Gln Ser His
        260                 265                 270

Glu Asp Asp Leu Ala Ile Phe Lys Thr Thr Asn Gln Leu Leu Gln Tyr
    275                 280                 285

Leu Leu Ile Asn Phe Gln Lys Val Gln Leu Ile Glu Asn Asn Lys Pro
290                 295                 300

Val Lys Thr Leu Tyr Val Leu Asp Ser Pro Glu Lys Thr Val Lys Leu
305                 310                 315                 320

Val Ala Gln Asn Ser Leu Phe Phe Ile Lys Pro Ile His Thr Lys Thr
            325                 330                 335

Lys Asn Thr Val His Ile Thr Lys Lys Ser Ser Thr Met Ile Ala Pro
        340                 345                 350

Leu Ser Lys Gly Gln Val Leu Gly Arg Ala Thr Leu Gln Asp Lys His
    355                 360                 365

Leu Ile Gly Gln Gly Tyr Leu Asp Thr Pro Pro Ser Ile Asn Leu Ile
370                 375                 380

Leu Gln Lys Asn Ile Ser Lys Ser Phe Phe Leu Lys Val Trp Trp Asn
385                 390                 395                 400

Arg Phe Val Arg Tyr Val Asn Thr Ser Leu
            405                 410

<210> SEQ ID NO 73
<211> LENGTH: 337
<212> TYPE: PRT
<213> ORGANISM: Artificial Sequence
<220> FEATURE:
<223> OTHER INFORMATION: GAS57Variant2

<400> SEQUENCE: 73

Met Lys Ser Phe Ser Leu Thr Phe Ser Phe Leu Asn Leu Leu Lys Tyr
1               5                   10                  15

Gly Thr Ile Lys Val Met Thr Lys Glu Phe His His Val Thr Val Leu
            20                  25                  30

Leu His Glu Thr Val Asp Met Leu Asp Ile Lys Pro Asp Gly Ile Tyr
        35                  40                  45

Val Asp Ala Thr Leu Gly Gly Ser Gly His Ser Ala Tyr Leu Leu Ser
    50                  55                  60

Lys Leu Gly Glu Glu Gly His Leu Tyr Cys Phe Asp Gln Asp Gln Lys
65                  70                  75                  80

Ala Ile Asp Asn Ala Gln Val Thr Leu Lys Ser Tyr Ile Asp Lys Gly
            85                  90                  95

Gln Val Thr Phe Ile Lys Asp Asn Phe Arg His Leu Lys Ala Arg Leu
        100                 105                 110

Thr Ala Leu Gly Val Asp Glu Ile Asp Gly Ile Leu Tyr Asp Leu Gly
    115                 120                 125

Val Ser Ser Pro Gln Leu Asp Glu Arg Glu Arg Gly Phe Ser Tyr Lys
    130                 135                 140

Gln Asp Ala Pro Leu Asp Met Arg Met Asp Arg Gln Ser Leu Leu Thr
145                 150                 155                 160

Ala Tyr Glu Val Val Asn Thr Tyr Pro Phe Asn Asp Leu Val Lys Ile
            165                 170                 175

```
Phe Phe Lys Tyr Gly Glu Asp Lys Phe Ser Lys Gln Ile Ala Arg Lys
                180                 185                 190

Ile Glu Gln Ala Arg Ala Ile Lys Pro Ile Glu Thr Thr Thr Glu Leu
            195                 200                 205

Ala Glu Leu Ile Lys Ala Lys Pro Ala Lys Glu Leu Lys Lys Lys
210                 215                 220

Gly His Pro Ala Lys Gln Ile Phe Gln Ala Ile Arg Ile Glu Val Asn
225                 230                 235                 240

Asp Glu Leu Gly Ala Ala Asp Glu Ser Ile Gln Asp Ala Met Glu Leu
                245                 250                 255

Leu Ala Leu Asp Gly Arg Ile Ser Val Ile Thr Phe His Ser Leu Glu
            260                 265                 270

Asp Arg Leu Thr Lys Gln Leu Phe Lys Glu Ala Ser Thr Val Asp Val
        275                 280                 285

Pro Lys Gly Leu Pro Leu Ile Pro Glu Asp Met Lys Pro Lys Phe Glu
290                 295                 300

Leu Val Ser Arg Lys Pro Ile Leu Pro Ser His Ser Glu Leu Thr Ala
305                 310                 315                 320

Asn Lys Arg Ala His Ser Ala Lys Leu Arg Val Ala Lys Lys Ile Arg
                325                 330                 335

Lys

<210> SEQ ID NO 74
<211> LENGTH: 644
<212> TYPE: PRT
<213> ORGANISM: Artificial Sequence
<220> FEATURE:
<223> OTHER INFORMATION: GAS57Variant3

<400> SEQUENCE: 74

Ala Asp Glu Leu Ser Thr Met Ser Glu Pro Thr Ile Thr Asn His Ala
1               5                   10                  15

Gln Gln Gln Ala Gln His Leu Thr Asn Thr Glu Leu Ser Ser Ala Glu
                20                  25                  30

Ser Lys Ser Gln Asp Thr Ser Gln Ile Thr Leu Lys Thr Asn Arg Glu
            35                  40                  45

Lys Glu Gln Ser Gln Asp Leu Val Ser Glu Pro Thr Thr Thr Glu Leu
        50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190
```

```
Phe Asp Ala Glu Ala Glu Pro Lys Ala Ile Lys Lys His Lys Ile Tyr
            195                 200                 205
Arg Pro Gln Ser Thr Gln Ala Pro Lys Glu Thr Val Ile Lys Thr Glu
        210                 215                 220
Glu Thr Asp Gly Ser His Asp Ile Asp Trp Thr Gln Thr Asp Asp Asp
225                 230                 235                 240
Thr Lys Tyr Glu Ser His Gly Met His Val Thr Gly Ile Val Ala Gly
                245                 250                 255
Asn Ser Lys Glu Ala Ala Ala Thr Gly Glu Arg Phe Leu Gly Ile Ala
            260                 265                 270
Pro Glu Ala Gln Val Met Phe Met Arg Val Phe Ala Asn Asp Ile Met
        275                 280                 285
Gly Ser Ala Glu Ser Leu Phe Ile Lys Ala Ile Glu Asp Ala Val Ala
290                 295                 300
Leu Gly Ala Asp Val Ile Asn Leu Ser Leu Gly Thr Ala Asn Gly Ala
305                 310                 315                 320
Gln Leu Ser Gly Ser Lys Pro Leu Met Glu Ala Ile Glu Lys Ala Lys
                325                 330                 335
Lys Ala Gly Val Ser Val Val Ala Ala Gly Asn Glu Arg Val Tyr
            340                 345                 350
Gly Ser Asp His Asp Asp Pro Leu Ala Thr Asn Pro Asp Tyr Gly Leu
        355                 360                 365
Val Gly Ser Pro Ser Thr Gly Arg Thr Pro Thr Ser Val Ala Ala Ile
370                 375                 380
Asn Ser Lys Trp Val Ile Gln Arg Leu Met Thr Val Lys Glu Leu Glu
385                 390                 395                 400
Asn Arg Ala Asp Leu Asn His Gly Lys Ala Ile Tyr Ser Glu Ser Val
                405                 410                 415
Asp Phe Lys Asp Ile Lys Asp Ser Leu Gly Tyr Asp Lys Ser His Gln
            420                 425                 430
Phe Ala Tyr Val Lys Glu Ser Thr Asp Ala Gly Tyr Asn Ala Gln Asp
        435                 440                 445
Val Lys Gly Lys Ile Ala Leu Ile Glu Arg Asp Pro Asn Lys Thr Tyr
450                 455                 460
Asp Glu Met Ile Ala Leu Ala Lys Lys His Gly Ala Leu Gly Val Leu
465                 470                 475                 480
Ile Phe Asn Asn Lys Pro Gly Gln Ser Asn Arg Ser Met Arg Leu Thr
                485                 490                 495
Ala Asn Gly Met Gly Ile Pro Ser Ala Phe Ile Ser His Glu Phe Gly
            500                 505                 510
Lys Ala Met Ser Gln Leu Asn Gly Asn Gly Thr Gly Ser Leu Glu Phe
        515                 520                 525
Asp Ser Val Val Ser Lys Ala Pro Ser Gln Lys Gly Asn Glu Met Asn
530                 535                 540
His Phe Ser Asn Trp Gly Leu Thr Ser Asp Gly Tyr Leu Lys Pro Asp
545                 550                 555                 560
Ile Thr Ala Pro Gly Gly Asp Ile Tyr Ser Thr Tyr Asn Asp Asn His
                565                 570                 575
```

```
Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Ser Pro Arg
625                 630                 635                 640

Gln Gln Gly Ala

<210> SEQ ID NO 75
<211> LENGTH: 1932
<212> TYPE: DNA
<213> ORGANISM: Artificial Sequence
<220> FEATURE:
<223> OTHER INFORMATION: GAS57Variant

<400> SEQUENCE: 75
gcagatgagc taagcacaat gagcgaacca acaatcacga atcacgctca acaacaagcg      60
caacatctca ccaatacaga gttgagctca gctgaatcaa atctcaaga cacatcacaa     120 atcactctca agacaaatcg tgaaaaagag caatcacaag atctagtctc tgagccaacc     180
acaactgagc tagctgacac agatgcagca tcaatggcta atacaggttc tgatgcgact     240
caaaaaagcg cttctttacc gccagtcaat acagatgttc acgattgggt aaaaaccaaa     300
ggagcttggg acaagggata caaggacaa ggcaaggttg tcgcagttat tgacacaggg     360
atcgatccgg cccatcaaag catgcgcatc agtgatgtat caactgctaa agtaaaatca     420
aaagaagaca tgctagcacg ccaaaaagcc gccggtatta attatgggag ttggataaat     480
gataaagttg tttttgcaca taattatgtg aaaatagcg ataatatcaa agaaaatcaa     540
ttcgaggatt ttgatgagga ctgggaaaac tttgagtttg atgcagaggc agagccaaaa     600
gccatcaaaa aacacaagat ctatcgtccc caatcaaccc aggcaccgaa agaaactgtt     660
atcaaaacag aagaaacaga tggttcacat gatattgact ggacacaaac agacgatgac     720
accaaatacg agtcacacgg tatgcatgtg acaggtattg tagccggtaa tagcaaagaa     780
gccgctgcta ctggagaacg cttttttagga attgcaccag aggcccaagt catgttcatg     840
cgtgtttttg ccaacgacat catgggatca gctgaatcac tctttatcaa agctatcgaa     900
gatgccgtgg ctttaggagc agatgtgatc aacctgagtc ttggaaccgc taatggggca     960
cagcttagtg gcagcaagcc tctaatggaa gcaattgaaa aagctaaaaa agccggtgta    1020
tcagttgttg tagcagcagg aaatgagcgc gtctatggat ctgaccatga tgatccattg    1080
gcgacaaatc cagactatgg tttggtcggt tctcccctcaa caggtcgaac accaacatca    1140
gtggcagcta taaacagtaa gtgggtgatt caacgtctaa tgacggtcaa agaattagaa    1200
aaccgtgccg atttaaacca tggtaaagcc atctattcag agtctgtcga ctttaaagac    1260
ataaaagata gcctaggtta tgataaatcg catcaatttg cttatgtcaa agagtcaact    1320
gatgcgggtt ataacgcaca agacgttaaa ggtaaaattg ctttaattga acgtgatccc    1380 aataaaaccct atgacgaaat gattgctttg gctaagaaac atggagctct gggagtactt    1440
atttttaata caagcctgg tcaatcaaac cgctcaatgc gtctaacagc taatgggatg    1500
gggataccat ctgctttcat atcgcacgaa tttggtaagg ccatgtccca attaaatggc    1560
aatggtacag gaagtttaga gtttgacagt gtggtctcaa aagcaccgag tcaaaaaggc    1620
aatgaaatga atcatttttc aaatttgggc ctaacttctg atggctattt aaaacctgac    1680
```

```
attactgcac caggtggcga tatctattct acctataacg ataaccacta tggtagccaa    1740
acaggaacaa gtatggcctc tcctcagatt gctggcgcca gccttttggt caaacaatac    1800
ctagaaaaga ctcagccaaa cttgccaaaa gaaaaaattg ctgatatcgt taagaaccta    1860
ttgatgagca atgctcaaat tcatgttaat ccagagacaa aaacgaccac ctcaccgcgt    1920
cagcaagggg ca                                                       1932
```

OUTER MEMBRANE VESICLES

This application is the U.S. National Phase of International Application No. PCT/EP2013/069415, filed Sep. 18, 2013 and published in English, which claims the benefit of U.S. Provisional Application No. US provisional applications U.S. 61/702,296, filed Sep. 18, 2012, and of U.S. Provisional Application No. 61/799,311, filed Mar. 15, 2013. The complete contents of all of the foregoing applications which are hereby incorporated herein by reference for all purposes.

SEQUENCE LISTING

The instant application contains a Sequence Listing which was submitted in ASCII format in PCT application PCT/EP2013/069415 and is hereby incorporated by reference in its entirety. Said ASCII copy, created on, Dec. 18, 2013 is named "PAT055225-WO-PCT Sequence Listing 2" and is 164,692 bytes in size.

TECHNICAL FIELD

This invention relates to vesicles from Gram-negative bacteria. The vesicles comprise heterologous proteins in their lumens. The vesicles are particularly useful in immunogenic compositions, e.g. vaccines.

BACKGROUND ART

Gram-negative bacteria can spontaneously release outer membrane vesicles (OMVs) during growth due to the turgor pressure of the cell envelope. The formation of such OMVs can be facilitated by disruption of certain bacterial components e.g. references 1 and 2 disrupted the *E. coli* Tol-Pal system to provide strains which release vesicles into the culture medium during growth. OMVs can also be produced by disruption of whole bacteria. Known OMV production methods include methods which use detergent treatment (e.g. with deoxycholate) [3 & 4], detergent-free methods [5], or sonication [6], etc.

OMVs are rich in immunogenic cell surface-associated, periplasmic and secreted antigens and have been used as vaccines, e.g. against *Neisseria meningitidis* serogroup B [7]. They are particularly suited for this use because the vesicles contain compounds that act as adjuvants, eliciting strong immune responses against the antigens. In this way, the vesicles are a closer mimic of the native bacterium for the immune system than purified antigenic proteins or other bacterial components. OMVs therefore remain an attractive target for vaccines and other immunogenic compositions. It has been suggested that the immunogenic properties of some protein antigens can be increased by engineering OMVs to display multiple antigens on the surfaces of OMVs by using ClyA as a fusion partner [8].

Several attempts have been made to target heterologous proteins, and in particular heterologous antigens, to OMVs. However, to date antigens that are foreign to the parental bacteria remain notably absent from OMVs largely because of challenges associated with the transport of heterologous proteins to the vesicles [11]. Most attempts to target heterologous proteins to OMVs have relied on covalent linkage of the heterologous proteins to integral membrane proteins. Examples of such covalently-linked heterologous proteins include fusions of the FLAG epitope to the full-length sequence of OmpA (outer membrane protein A), fusions of the FLAG epitope to the full-length sequence of PagP (PhoPQ-activated gene P) [9], and fusions of GFP to ClyA (Cytolysin) [10]. By virtue of their covalent linkages to membrane proteins, the resulting fusion proteins are targeted to the outer membrane and are thus included in the OMVs. These methods have drawbacks, in particular because it is difficult to overexpress a large amount of an integral membrane protein without detrimental effects of the transformed bacterium.

Targeting periplasmic proteins to OMVs has also proven to be difficult. A fusion of GFP to a Tat (twin arginine transporter) signal sequence resulted in overexpression of GFP that was targeted to the periplasm, but GFP fluorescence was barely above background fluorescence levels in OMVs [11], suggesting that the GFP was either not incorporated into the OMVs or was non-functional in the OMV because of incorrect folding.

There remains a need to develop a method suitable for expressing heterologous proteins in OMVs, and in particular a method to express antigenic proteins in OMVs. There also remains a need for alternative or improved OMVs, particularly for use in vaccines.

DISCLOSURE OF THE INVENTION

The inventors have discovered that targeting heterologous proteins to the lumen of OMVs overcomes many of the problems associated with targeting heterologous proteins to the membrane of OMVs. Surprisingly, the inventors have also found that OMVs containing heterologous proteins that are in the lumen are capable of eliciting immune responses to the proteins when administered to a mammal.

Thus, the invention provides an outer membrane vesicle (OMV) from a Gram-negative bacterium, wherein the OMV comprises at least one heterologous protein that is free in its lumen, and the OMV is capable of eliciting an immune response to the heterologous protein when administered to a mammal.

The invention also provides a method of preparing an OMV of the invention, the method comprising the step of expressing the heterologous protein in the periplasm of the Gram-negative bacterium. The invention further provides an OMV obtained or obtainable by this method.

The invention also provides a pharmaceutical composition comprising (a) an OMV of the invention and (b) a pharmaceutically acceptable carrier.

The invention also provides a method of generating an immune response in a mammal, the method comprising administering an effective amount of an OMV from a Gram-negative bacterium to the mammal, wherein the OMV comprises at least one heterologous protein in its lumen, and wherein the immune response is to the heterologous protein in the OMV. In some embodiments of this aspect of the invention, the protein is free in the lumen of the OMV. The invention also provides a method of generating an immune response in a mammal comprising administering a pharmaceutical composition of the invention to the mammal, wherein the immune response is to the heterologous protein in the OMV.

OMVs

The present invention provides an outer membrane vesicle (OMV) from a Gram-negative bacterium, wherein the OMV comprises at least one heterologous protein that is free in its lumen, and the OMV is capable of eliciting an immune response to the heterologous protein when administered to a mammal.

OMVs are well known in the art and are spontaneously released into culture medium by bacteria. 'Native OMVs'

('NOMVs' [12]), microvesicles (MVs [13]), detergent-extracted OMVs (DOMVs), mutant-derived OMVs (m-OMV), and blebs, which are outer-membrane protrusions that remain attached to bacteria prior to release as MVs ([14]; [15]), all form part of the invention and are collectively referred to as OMVs herein.

OMVs of the invention can be obtained from any suitable Gram-negative bacterium. The Gram-negative bacterium is typically *E. coli*. However, instead of *E. coli* it may be a different Gram-negative bacterium. Preferred Gram-negative bacteria for use in the invention include bacteria that are not pathogenic in humans. For example, the bacteria may be commensalistic in humans. However, in some embodiments bacteria are used that are not typically found in human hosts at all. Exemplary species for use in the invention include species in any of genera *Escherichia, Shigella, Neisseria, Moraxella, Bordetella, Borrelia, Brucella, Chlamydia Haemophilus, Legionella, Pseudomonas, Yersinia, Helicobacter, Salmonella, Vibrio,* etc. In particular, the bacterium may be a *Shigella* species (such as *S. dysenteriae, S. flexneri, S. boydii* or *S. sonnei*). Alternatively, it may be a *Neisseria* species, particularly a non-pathogenic species such as *N. bacilliformis, N. cinerea, N. elongata, N. flavescens, N. lactamica, N. macacae, N. mucosa, N. polysaccharea, N. sicca* or *N. subflava*, and in particular *N. lactamica*. Alternatively, a pathogenic species of *Neisseria* may be used, e.g. *N. gonorrhoeae* or *N. meningitidis*. In other examples, the bacterium may be *Bordetella pertussis, Borrelia burgdorferi, Brucella melitensis, Brucella ovis, Chlamydia psittaci, Chlamydia trachomatis, Moraxella catarrhalis, Haemophilus influenzae* (including non-typeable stains), *Legionella pneumophila, Pseudomonas aeruginosa, Yersinia enterocolitica, Helicobacter pylori, Salmonella enterica* (including serovars *typhi* and *typhimurium*, as well as serovars *paratyphi* and *enteritidis*), *Vibrio cholerae, Proteus, Citrobacter, Serratia, Erwinia, Pasteurella* etc. Photosynthetic Gram-negative bacteria may also be used. Typically, the bacterium is a competent strain. This feature facilitates genetic modification of the bacterium.

In a particular embodiment, the Gram-negative bacterium is a "hyperblebbing" strain of that bacterium. Hyperblebbing Gram-negative bacteria from which blebs may more easily be made in higher yield and may be more homogeneous in nature are described in WO 02/062378. For example, the blebs may be derived from bacteria selected from the group consisting of *Neisseria meningitidis, Neisseria lactamica, Neisseria gonorrhoeae, Helicobacter pylori, Salmonella typhi, Salmonella typhimurium, Vibrio cholerae, Shigella* spp., *Haemophilus influenzae, Bordetella pertussis, Pseudomonas aeruginosa* and *Moraxella catarrhalis*.

In a specific embodiment, the bacterium is an *E. coli* ompA mutant and/or *E. coli* tolR mutant. In some embodiments, the bacterium is selected from *E. coli* BL21(DE3) ΔompA, *E. coli* BL21(DE3)ΔompAΔtolR, *E. coli* BL21 (DE3)ΔtolR, *E. coli* ΔnlpI, or *E. coli* ΔdegP. The Δ symbol is used herein to refer to a bacterial strain from which the coding sequence of the gene recited after the Δ symbol has been deleted. Thus, a bacterial strain which is "ΔompA" does not comprise the coding sequence for the ompA gene. Likewise, a bacterial strain which is "ΔtolR" does not comprise the coding sequence for the tolR gene. The entire coding sequence may be deleted. However, the coding sequence may alternatively be deleted in part. For example, the N-terminal half or the C-terminal half may be deleted. Alternatively, the ompA and/or tolR genes may be mutated by the introduction of one or more substitutions and/or insertions.

The *E. coli* ΔtolR mutant strains and *E. coli* ΔompA mutant strains overproduce OMVs relative to wild type *E. coli*. Thus, the mutation of the ompA gene and/or one or more components of the Tol-Pal complex results in the mutant bacterium producing an increased number of OMVs compared to its respective wild type strain which carries a wild type ompA gene and/or Tol-Pal complex. OmpA is an integral membrane protein and is the most abundant of the outer membrane proteins in *E. coli*. It is, therefore, surprising that an *E. coli* lacking the OmpA protein is viable. Indeed, according to Murakami et al. [16], an *E. coli* ompA single mutant cannot promote vesicle release.

Heterologous Protein

The heterologous protein of the invention is targeted to and expressed in the periplasm of the Gram-negative bacterium such that the heterologous protein is in the lumen of the OMV. In some embodiments, the heterologous protein is free in the lumen of the OMV.

The protein may be an amino acid polymer of any length. The amino acid polymer may be linear or branched, it may comprise modified amino acids, and it may be interrupted by non-amino acids. The terms also encompass an amino acid polymer may have been modified naturally or by intervention; for example, by disulfide bond formation, additional glycosylation, partial or complete deglycosylation, lipidation, acetylation, phosphorylation, or any other manipulation or modification, such as conjugation with a labelling component. Also included within the definition are, for example, proteins containing one or more analogues of an amino acid (including, for example, unnatural amino acids, etc.), as well as other modifications known in the art. Proteins can occur as single chains or associated chains. Proteins in the context of the invention can be naturally or non-naturally glycosylated (i.e. the polypeptide has a glycosylation pattern that differs from the glycosylation pattern found in the corresponding naturally occurring polypeptide).

As used herein, the term "heterologous" means that the protein is from a species that is different from the species of bacterium from which the OMV is obtained (the heterologous organism). Typically, the protein is an antigen from a pathogen genus different from the genus of bacterium from which the OMV is obtained.

In a specific embodiment of the invention, the heterologous protein is an immunogenic protein which can elicit an immune response in the recipient. In a specific embodiment, the immunogenic protein, and thus the heterologous protein, comprises or consists of an antigen. The antigen may elicit an immune response against a protist, a bacterium, a virus, a fungus, or any other pathogen including multicellular pathogens, or a parasite (or, in some embodiments, against an allergen; and in other embodiments, against a tumor antigen). The immune response may comprise an antibody response (usually including IgG) and/or a cell-mediated immune response. The polypeptide antigen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The antigen will typically be a surface polypeptide e.g. an adhesin, a hemagglutinin, an envelope glycoprotein, a spike glycoprotein, etc.

In some embodiments the antigen elicits an immune response against one of these bacteria:

*Neisseria meningitidis*: useful antigens include, but are not limited to, membrane proteins such as adhesins, autotransporters, toxins, iron acquisition proteins, factor H binding protein (fHbp or 741), *Neisseria* Heparin-Binding Antigen (NHBA or 287), NadA (or 961), 953/936 and *Neisseria meningitides* serogroup B by (fHbp). A combination of three useful polypeptides is disclosed in reference 17.

*Streptococcus pneumoniae*: useful polypeptide antigens are disclosed in reference 18. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful antigens include, but are not limited to, the polypeptides disclosed in references 19 and 20, e.g. GAS25-574, such as GAS 25 (SEQ ID:41, SEQ ID:42), GAS40 (SEQ ID:43, SEQ ID:44, SEQ ID:45, SEQ ID:46, SEQ ID:47, SEQ ID:48, SEQ ID:49, SEQ ID:50, SEQ ID:51, SEQ ID:52, SEQ ID:53, SEQ ID:54, SEQ ID:55, SEQ ID:56, SEQ ID: 57, SEQ ID:58, SEQ ID:59, SEQ ID:60, SEQ ID:61, SEQ ID:62, SEQ ID:63, SEQ ID:64, SEQ ID:65, SEQ ID:66, SEQ ID: 67, SEQ ID:68, SEQ ID:69, SEQ ID:70), GAS57 (SEQ ID:39, SEQ ID:40, SEQ ID:71, SEQ ID:72, SEQ ID:73, SEQ ID:74; SEQ ID:75),88, 23, 99, 97, 24, 5, 208, 193, 67, 64, 101, 205, 268, 68, 189, 165 or 201.

*Moraxella catarrhalis*.

*Bordetella pertussis*: Useful *pertussis* antigens include, but are not limited to, acellular or whole-cell *pertussis* antigens, *pertussis* holotoxin or toxoid (PT), filamentous haemagglutinin (FHA), pertactin, and agglutinogens 2 and 3.

*Staphylococcus aureus*: Useful antigens include, but are not limited to, the polypeptides disclosed in reference 21, such as a hemolysin, esxA, esxB, esxAB, ferrichrome-binding protein (sta006) and/or the sta011 lipoprotein.

*Clostridium tetani*: the typical antigen is tetanus toxoid.

*Cornynebacterium diphtheriae*: the typical antigen is diphtheria toxoid.

*Haemophilus influenzae*: Useful antigens include, but are not limited to, the polypeptides disclosed in references 22 and 23.

*Pseudomonas aeruginosa*

*Streptococcus agalactiae*: useful antigens include, but are not limited to, the polypeptides disclosed in reference 19, such as 67, 80, 1523, 3, 328 or 211.

*Chlamydia trachomatis*: Useful antigens include, but are not limited to, PepA, LcrE, ArtJ, DnaK, CT398, OmpH-like, L7/L12, OmcA, AtoS, CT547, Eno, HtrA and MurG (e.g. as disclosed in reference 24. LcrE [25] and HtrA [26] are two preferred antigens.

*Chlamydia pneumoniae*: Useful antigens include, but are not limited to, the polypeptides disclosed in reference 27.

*Helicobacter pylori*: Useful antigens include, but are not limited to, CagA, VacA, NAP, and/or urease[28].

*Escherichia coli*: Useful antigens include, but are not limited to, antigens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC polypeptide antigens are disclosed in references 29 and 30. Useful MNEC antigens are disclosed in reference 31. A useful antigen for several *E. coli* types is AcfD [32].

*Bacillus anthracis*

*Yersinia pestis*: Useful antigens include, but are not limited to, those disclosed in references 33 and 34.

*Staphylococcus epidermidis*, e.g. type I, II and/or III capsular polysaccharide obtainable from strains ATCC-31432, SE-360 and SE-10

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae*.

*Francisella*, such as *F. novicida, F. philomiragia, F. tularensis*.

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Mycobacterium leprae*

*Rickettsia*

*Listeria monocytogenes*

*Vibrio cholerae*

*Salmonella typhi*

*Borrelia burgdorferi*

*Porphyromonas gingivalis*

*Klebsiella*

*Rickettsia prowazekii*.

In some embodiments the antigen is an antigen from *Chlamydia, Streptococcus, Pseudomonas, Shigella, Campylobacter, Salmonella, Neisseria* or *Helicobacter*.

In some embodiments the antigen elicits an immune response against one of these viruses:

Orthomyxovirus: Useful antigens can be from an influenza A, B or C virus, such as the hemagglutinin, neuraminidase or matrix M2 proteins. Where the antigen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral antigens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: Viral antigens include, but are not limited to, those derived from Orthopoxvirus such as *Variola vera*, including but not limited to, *Variola major* and *Variola minor*.

Picornavirus: Viral antigens include, but are not limited to, those derived from Picornaviruses, such as *Enteroviruses, Rhinoviruses, Heparnavirus, Cardioviruses* and *Aphthoviruses*. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral antigens include, but are not limited to, those derived from an *Orthobunyavirus*, such as California encephalitis virus, a *Phlebovirus*, such as Rift Valley Fever virus, or a *Nairovirus*, such as Crimean-Congo hemorrhagic fever virus.

Heparnavirus: Viral antigens include, but are not limited to, those derived from a Heparnavirus, such as hepatitis A virus (HAV) e.g. inactivated virus, hepatitis B virus e.g. the surface and/or core antigens or hepatitis C virus.

Filovirus: Viral antigens include, but are not limited to, those derived from a filovirus, such as an Ebola virus (including a Zaire, Ivory Coast, Reston or Sudan ebolavirus) or a Marburg virus.

Togavirus: Viral antigens include, but are not limited to, those derived from a Togavirus, such as a *Rubivirus*, an *Alphavirus*, or an Arterivirus. This includes rubella virus.

Flavivirus: Viral antigens include, but are not limited to, those derived from a *Flavivirus*, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral antigens include, but are not limited to, those derived from a *Pestivirus*, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. A composition can include hepatitis B virus surface antigen (HBsAg).

Other hepatitis viruses: A composition can include an antigen from a hepatitis C virus, delta hepatitis virus, hepatitis E virus, or hepatitis G virus.

Rhabdovirus: Viral antigens include, but are not limited to, those derived from a Rhabdovirus, such as a Lyssavirus (e.g. a Rabies virus) and Vesiculovirus (VSV). An example of a Rabies antigen is lyophilised inactivated virus.

Caliciviridae: Viral antigens include, but are not limited to, those derived from Calciviridae, such as Norwalk virus (*Norovirus*), and Norwalk-like Viruses, such as Hawaii Virus and Snow Mountain Virus.

Coronavirus: Viral antigens include, but are not limited to, those derived from a SARS *coronavirus*, avian infectious bronchitis (IBV), Mouse hepatitis virus (MHV), and Porcine transmissible gastroenteritis virus (TGEV). The *coronavirus* antigen may be a spike polypeptide.

Retrovirus: Viral antigens include, but are not limited to, those derived from an Oncovirus, a Lentivirus (e.g. HIV-1 or HIV-2) or a Spumavirus, e.g. gp120, gp140 or gp160

Reovirus: Viral antigens include, but are not limited to, those derived from an Orthoreovirus, a Rotavirus, an Orbivirus, or a Coltivirus.

Parvovirus: Viral antigens include, but are not limited to, those derived from Parvovirus B19.

Herpesvirus: Viral antigens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral antigens include, but are not limited to, those derived from *Papillomaviruses* and *Polyomaviruses*. The (human) *papillomavirus* may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral antigens include those derived from adenovirus serotype 36 (Ad-36).

In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, Cunninghamella spp, Saksenaea spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the antigen elicits an immune response against a parasite from the *Plasmodium* genus, such as *P. falciparum, P. vivax, P. malariae* or *P. ovale*. Thus the invention may be used for immunising against malaria. In some embodiments the antigen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the antigen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale,* and *Sorghum,* the orders of Asterales and Urticales including herbs of the genera *Ambrosia, Artemisia,* and *Parietaria.* Other important inhalation allergens are those from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and *Ctenocepphalides,* and those from mammals such as cat, dog and horse, venom allergens including such originating from stinging or biting insects such as those from the taxonomic order of Hymenoptera including bees (*Apidae*), wasps (*Vespidea*), and ants (*Formicoidae*).

In some embodiments the antigen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor antigens include, but are not limited to, p15, Hom/Mel-40, H-Ras, E2A-PRL, H4-RET, IGH-IGK, MYL-RAR, Epstein Barr virus antigens, EBNA, human *papillomavirus* (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

In a further specific example, the heterologous protein is β lactamase (TEM1), fHbp from *Neisseria meningitides*, the double mutant of extracellular cholesterol depending streptolysin O (Slo-dm) from *Streptococcus pyogenes*, the cell envelope serine protease SpyCep from *Streptococcus pyogenes*, or the putative surface exclusion protein Spy0269 from *Streptococcus pyogenes*.

The heterologous protein may be a soluble protein, a peripheral membrane protein or an integral membrane protein when expressed in the heterologous organism from which it is derived, i.e. when present in its native environment. For example, if the heterologous protein is derived from a Gram-negative bacterium, it may be a cytoplasmic, periplasmic or membrane-associated protein in the native Gram-negative bacterium. However, when present in the OMV, the heterologous protein is in the lumen of the OMV, and preferably free in the lumen of the OMV. Therefore, the heterologous protein may be modified, as compared to the wild-type protein, for example by deleting any membrane anchor(s).

The term "in the lumen" of the OMV encompasses both proteins that are membrane associated but not surface exposed, and proteins that are free in the lumen of the OMV. The heterologous protein is generally free in the lumen of the OMV in the present invention. By "free in the lumen" it is meant that the heterologous protein is not integrally associated with the membrane of the OMV. Integral association with the membrane describes those proteins that require the use of a detergent or other apolar solvent to dissociate the protein from the membrane. A review of membrane anchors for integral association with the membrane can be found in reference 35. A protein that is free in the lumen of the OMV may be associated with the membrane or an integral membrane protein by non-covalent interactions or may not associate with the membrane of the OMV at all. For example, the protein may loosely or temporarily associate with the membrane, e.g. via hydrophobic, electrostatic, ionic and/or other non-covalent interactions with the lipid bilayer and/or to an integral protein.

One advantage of the heterologous protein being in the lumen of OMV, rather than being associated with the membrane and exposed, is that it may be protected from protease degradation in vivo. This protection may in turn result in more efficient B cell activation.

In a particular embodiment, the heterologous protein is a soluble protein. By "soluble protein" it is meant that the protein does not form any association with lipid membrane. A soluble protein does not contain a membrane anchor such as a peptide transmembrane domain, other peptide membrane anchoring domain, or a non-peptide membrane anchor such as a lipid.

The OMV is capable of eliciting an immune response to the heterologous protein when administered to a mammal. The immune response may be a cellular or a humoral immune response. Typically, the immune response is an antibody response.

In one embodiment, the OMV of the invention is capable of eliciting an immune response against the pathogen from which the heterologous protein is derived. For example, the heterologous protein preferably elicits a T-cell immune response that can neutralise the infection and/or virulence of the pathogen from which the heterologous protein is derived. Preferred heterologous proteins for use in the invention are therefore those which are recognised by the cellular immune system upon infection with a pathogen of interest. More preferred are those heterologous proteins which elicit a protective T-cell immune response against a pathogen of interest.

In one embodiment, the OMV of the invention is capable of eliciting antibodies that recognise a pathogen from which the heterologous protein is derived. For example, the heterologous protein preferably elicits antibodies that can bind to, and preferably neutralise the infection and/or virulence of the pathogen from which the heterologous protein is derived. Preferred heterologous proteins for use in the invention are therefore those which are recognised by antisera upon infection with a pathogen of interest. More preferred are those heterologous proteins which elicit a protective immune response against a pathogen of interest.

In some embodiments, the heterologous protein is immunogenic when it is presented in the OMV but is not immunogenic when administered in purified form.

In one embodiment, the heterologous proteins of the invention are functionally active in the lumen of the OMV and/or upon release from the lumen of the OMV (e.g. by detergent-mediated disruption of the OMV). Functional activity is an indicator that the heterologous protein is folded correctly and has the same or substantially the same tertiary and quaternary structure as the same protein in its native state. By "functionally active" it is meant that the heterologous protein retains at least 50% or more of at least one biological activity of the same protein when expressed in its native environment (e.g. in the organism from which it is derived). For example, the heterologous protein can be considered to be functionally active if it retains at least 50%, 60%, 70%, 80%, 90% or more or of at least one biological activity of the same protein when expressed in its native environment.

In embodiments in which the heterologous protein comprises or consists of a fragment of a wild type protein or of a variant thereof, the fragment or variant may be functionally active. By "fragment of a wild type protein" it is meant that the heterologous protein comprises or consists of at least 7 consecutive amino acids from the wild type protein. In some embodiments, the fragment consists of at least 7, 8, 9, 10, 20, 30, 40 or more amino acids from the wild type protein. The fragment may consist of at least 10%, 20%, 30%, 40%, 50%, 60%, 70%, 80%, 90%, 95% or more of the wild type protein.

Preferably, the fragment is an immunogenic fragment of the heterologous protein. By "immunogenic fragment" it is meant that the fragment has at least one epitope in common with the heterologous protein. The term "epitope" encompasses any kind of epitope and includes both B-cell and T-cell epitopes, and both linear and discontinuous epitopes. In one embodiment, an antibody that binds specifically to the heterologous protein also binds specifically to the immunogenic fragment, i.e. the heterologous protein and immunogenic fragment thereof both contain the epitope to which that antibody binds. By "binds specifically", it is meant that the antibodies bind to the heterologous protein of the invention with substantially greater affinity than to BSA. Preferably, the affinity is at least 100-fold, $10^3$-fold, $10^4$-fold, $10^5$-fold, $10^6$-fold etc. greater for the heterologous protein of the invention than for BSA.

Epitopes present in heterologous proteins can be determined and/or predicted using any methods known in the art. For example, epitope prediction software such as EpiToolKit, which is a web server for computational immunomics [36]. This epitope prediction software provides several methods for predicting potential T-cell eptiopes, both for MHC Class I and MHC Class II binding epitopes.

The presence of B-cell epitopes can also be predicted using any known method in the art, for example as described in references [37, 38 and 39]. The presence of continuous linear epitopes and/or discontinuous epitopes can be predicted using the methods described therein.

By "variant of a wild type protein" it is meant that the heterologous protein comprises or consists of a full length protein, e.g. a protein with the same number of amino acids as the wild-type protein, or a fragment of the wild type protein that contains one or more variations in amino acid sequence when compared to the wild type sequence. A variant may have at least 50%, 60%, 70%, 80%, 90%, 95% or more sequence identity to the wild type protein. In some embodiments, the variant is also functionally active.

The heterologous protein may be fused to a fusion partner, i.e. the heterologous protein may be part of a fusion protein. Fusion proteins may comprise a sequence -X-Y- or -Y-X-, wherein: -X- is a heterologous protein as defined above, and -Y- is an additional polypeptide sequence. In one particular Embodiment -Y- is a protein tag that aids detection of the heterologous protein such as 6×HIS, FLAG, HA, GST, GFP or another fluorescent protein, and/or luciferase or any suitable polypeptide which aids in the function of the heterologous protein. When the heterologous protein is part of a fusion protein, the entire fusion protein will be in the lumen of the OMV. In some embodiments, the fusion protein will be free in the lumen of the OMV.

The OMV of the present invention comprises at least one heterologous protein in the lumen of the OMV. The OMV may therefore contain at least 1, 2, 3, 4, 5, 6, 7, 8, 9, 10 or more heterologous proteins in the lumen of the OMV, and preferably free in the lumen of the OMV. In addition to the at least one heterologous protein in the lumen of the OMV, the OMV of the invention may also comprise at least one heterologous protein associated with the membrane of the OMV. For example, the OMV of the invention may comprise at least one heterologous protein in the lumen of the OMV and 1, 2, 3, 4, 5, 6, 7, 8, 9, 10 or more heterologous proteins associated with the membrane of the OMV.

In a particular embodiment, the heterologous proteins comprise the double mutant of extracellular cholesterol depending streptolysin O (Slo-dm) from *Streptococcus pyogenes* and the putative surface exclusion protein Spy0269 from *Streptococcus pyogenes*. In a further particular embodiment, the heterologous proteins comprise the double mutant of extracellular cholesterol depending streptolysin O (Slo-dm) from *Streptococcus pyogenes*, the cell envelope serine protease SpyCEP from *Streptococcus pyogenes*, and the putative surface exclusion protein Spy0269 from *Streptococcus pyogenes*.

Methods of Preparing OMVs of the Invention

The invention also provides a method of preparing an OMV of the invention, the method comprising the step of expressing the heterologous protein in the periplasm of the Gram-negative bacterium.

In a particular embodiment, the heterologous protein is expressed in the periplasm of the Gram-negative bacterium using an expression vector comprising a nucleic acid sequence encoding the heterologous protein operatively linked to a nucleic acid encoding a signal sequence of a periplasmic protein.

Targeting of the heterologous proteins can be achieved by fusing the signal sequence of a protein which is naturally found in the periplasm and/or OMVs to a heterologous protein. Protein translocation through the inner membrane and to the periplasm may, for example, be accomplished by way of one of three pathways: SecB-dependent (SEC), signal recognition particle (SRP) or twin-arginine translocation (TAT). Any of these pathways can be used.

An example of a periplasmic signal sequence that can be used in the present invention is the signal sequence of OmpA. However, other possible signal sequences could be used including the Tat signal sequence, and the DsbA signal sequence. Export to the periplasm can be optimised using a series of vectors, each targeting a different export pathway. For example, the ACES Signal Sequence Expression Vectors [40] can be used to optimise translocation of the heterologous protein to the periplasm.

In some embodiments, the native signal sequence of the heterologous protein is replaced by the signal sequence of a periplasmic protein. In other embodiments, the heterologous protein is fused to the signal sequence of the periplasmic protein without replacing the native signal sequence, if present.

Specific embodiments of this aspect of the invention include using an expression vector comprising a nucleic acid sequence encoding the signal sequence of OmpA operably linked to a nucleic acid encoding the heterologous protein, for example the pET-OmpA plasmid shown in FIG. 1. In this embodiment, the OmpA signal sequence may have the nucleotide sequence ATGAAAAAGACAGCTATCGCGAT-TGCAGTGGCACTGGCTGGTTTCGCTACCG-TAGCGCAGG CC (SEQ ID NO:1). In this embodiment, the plasmid is a pET21b-derived plasmid. However, any other suitable plasmid backbone known in the art can also be used. Suitable plasmid backbones include pGEX, pUC19, pALTR, pET, pQE, pLEX, pHAT or any other plasmid vector that is cablable of replication in gram-negative bacteria.

Any Gram-negative bacteria that are capable of producing OMVs, for example those mentioned herein, can be transformed with the expression vectors described above in order to produce OMVs comprising the heterologous protein in their lumen, and preferably free in their lumen Methods for preparing OMVs are known in the art, and any suitable method can be used to generate OMVs of the invention. These methods generally involve a step of obtaining vesicles from a culture of the bacterium. The OMVs can be obtained by disruption of or blebbing from the outer membrane of the bacterium to form vesicles therefrom. OMVs can also be prepared artificially from bacteria, for example by sarkosyl-extraction of OMVs from 'ΔGNA33' meningococci, as described in reference 41. 'Native OMVs' ('NOMVs' [42]), microvesicles (MVs [43]), detergent-extracted OMVs (DOMVs), mutant-derived OMVs (m-OMV), and blebs, which are outer-membrane protrusions that remain attached to bacteria prior to release as MVs ([44]; [45]), all form part of the invention and are collectively referred to as OMVs herein.

OMVs (including blebs, MVs and NOMVs) include naturally-occurring membrane vesicles that form spontaneously during bacterial growth and are released into culture medium. Preferably, the OMVs of the invention are naturally occurring OMVs because separation of spontaneously-released OMVs from the culture medium is more convenient than methods which involve deliberate disruption of the outer membrane (e.g. by detergent treatment or sonication) to produce artificially induced OMVs. Moreover, they are substantially free from inner membrane and cytoplasmic contamination. OMVs typically have a diameter of 35-120 nm by electron microscopy e.g. 50 nm diameter and can be purified from the culture medium. The purification ideally involves separating the OMVs from living and/or intact bacteria e.g. by size-based filtration using a filter, such as a 0.22 µm filter, which allows the OMVs to pass through but which does not allow intact bacteria to pass through, or by using low speed centrifugation to pellet cells while leaving the blebs in suspension. A preferred method involving a two stage size filtration process is described in ref 46.

Thus, unlike the culture medium, OMV-containing compositions of the invention will generally be substantially free from whole bacteria, whether living or dead. The size of the OMVs means that they can readily be separated from whole bacteria by filtration e.g. as typically used for filter sterilisation. Although OMVs will pass through a standard 0.22 µm filters, these can rapidly become clogged by other material, and so it may be useful to perform sequential steps of filter sterilisation through a series of filters of decreasing pore size before using a 0.22 µm filter. Examples of preceding filters would be those with pore size of 0.8 µm, 0.45 µm, etc.

In an alternative embodiment, OMVs may be prepared artificially from bacteria, and may be prepared using detergent treatment (e.g. with deoxycholate or sarkosyl), or by non-detergent means (e.g. see reference 47). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate[48 & 49] being preferred for treating *Neisseria*) at a pH sufficiently high not to precipitate the detergent [50]. Other techniques may be performed substantially in the absence of detergent [47] using techniques such as sonication, homogenisation, microfluidisation, cavitation, osmotic shock, grinding, French press, blending, etc. Methods using no or low detergent can retain useful antigens such as NspA [47]. Thus a method may use an OMV extraction buffer with about 0.5% deoxycholate or lower e.g. about 0.2%, about 0.1%, <0.05% or zero.

A useful process for OMV preparation is described in reference 51 and involves ultrafiltration on crude OMVs, rather than instead of high speed centrifugation. The process may involve a step of ultracentrifugation after the ultrafiltration takes place.

The invention provides an OMV obtained or obtainable by the methods described above.

Pharmaceutical Compositions

The invention provides a pharmaceutical composition comprising (a) an OMV of the invention and (b) a pharmaceutically acceptable carrier. The invention also provides a process for preparing such a composition, comprising the step of admixing OMVs of the invention with a pharmaceutically acceptable carrier.

The invention also provides a container (e.g. vial) or delivery device (e.g. syringe) pre-filled with a pharmaceutical composition of the invention. The invention also provides a process for providing such a container or device, comprising introducing into the container or device a vesicle-containing composition of the invention.

The immunogenic composition may include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref 52.

Bacteria can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

A pharmaceutical carrier may include a temperature protective agent, and this component may be particularly useful in adjuvanted compositions (particularly those containing a mineral adjuvant, such as an aluminium salt). As described in reference 53, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

The composition is preferably sterile. It is preferably pyrogen-free. It is preferably buffered e.g. at between pH 6 and pH 8, generally around pH 7. Compositions of the invention may be isotonic with respect to humans.

Immunogenic compositions comprise an immunologically effective amount of immunogenic vesicles, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Previous work with vesicle vaccines (e.g. for meningococcus) offers pharmaceutical, posological and formulation guidance for compositions of the invention. The concentration of vesicles in compositions of the invention will generally be between 10 and 500 µg/ml, preferably between 25 and 200 µg/ml, and more preferably about 50 µg/ml or about 100 µg/ml (expressed in terms of total protein in the vesicles). A dosage volume of 0.5 ml is typical for injection.

The composition may be administered in conjunction with other immunoregulatory agents. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref 57], or mixtures of different mineral compounds, with the compounds taking any suitable form (e.g. gel, crystalline, amorphous, etc.), and with adsorption being preferred. The mineral containing compositions may also be formulated as a particle of metal salt.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at $1070\ cm^{-1}$ and a strong shoulder at $3090\text{-}3100\ cm^{-1}$ [chapter 9 of ref 57]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at $3164\ cm^{-1}$ (e.g. at 200° C.) indicates the presence of structural hydroxyls [ch. 9 of ref 57].

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

B. Oil Emulsions

Oil emulsion compositions suitable for use as adjuvants in the invention include squalene-water emulsions, such as MF59™ [Chapter 10 of ref. 57; see also ref. 54] (5% Squalene, 0.5% TWEEN™ 80, and 0.5% SPAN™ 85, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolisable) and biocompatible. The oil droplets in the emulsion are generally less than 5 μm in diameter, and advantageously the emulsion comprises oil droplets with a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising squalene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the TWEEN™s), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON™ X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as BRIJ™ surfactants), such as triethyleneglycol monolauryl ether (BRIJ™ 30); and sorbitan esters (commonly known as the SPAN™s), such as sorbitan trioleate (SPAN™ 85) and sorbitan monolaurate. Preferred surfactants for including in the emulsion are TWEEN™ 80 (polyoxyethylene sorbitan monooleate), SPAN™ 85 (sorbitan trioleate), lecithin and TRITON™ X-100. As mentioned above, detergents such as TWEEN™ 80 may contribute to the thermal stability seen in the examples below. Mixtures of surfactants can be used e.g. TWEEN™ 80/SPAN™ 85 mixtures. A combination of a polyoxyethylene sorbitan ester such as polyoxyethylene sorbitan monooleate (TWEEN™ 80) and an octoxynol such as t-octylphenoxypolyethoxyethanol (TRITON™ X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN™ 80) 0.01 to 1%, in particular about 0.1%; octyl- or nonylphenoxy polyoxyethanols (such as TRITON™ X-100, or other detergents in the TRITON™ series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, TWEEN™ 80, and SPAN™ 85. The composition of the emulsion by volume can be about 5% squalene, about 0.5% polysorbate 80 and about 0.5% SPAN™ 85. In weight terms, these ratios become 4.3% squalene, 0.5% polysorbate 80 and 0.48% SPAN™ 85. This adjuvant is known as 'MF59™' [54-56], as described in more detail in Chapter 10 of ref. 57 and chapter 12 of ref. 58. The MF59™ emulsion advantageously includes citrate ions e.g. 10 mM sodium citrate buffer.

An emulsion comprising squalene, an α-tocopherol, and polysorbate 80. These emulsions may have from 2 to 10% squalene, from 2 to 10% tocopherol and from 0.3 to 3% TWEEN™ 80, and the weight ratio of squalene:tocopherol is preferably <1 (e.g. 0.90) as this provides a more stable emulsion. Squalene and TWEEN™ 80 may be present volume ratio of about 5:2, or at a weight ratio of about 11:5. One such emulsion can be made by dissolving TWEEN™ 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a TRITON™ detergent (e.g. TRITON™ X-100). The emulsion may also include a 3d-MPL (see below). The emulsion may contain a phosphate buffer.

An emulsion comprising a polysorbate (e.g. polysorbate 80), a TRITON™ detergent (e.g. TRITON™ X-100) and a tocopherol (e.g. an α-tocopherol succinate). The emulsion may include these three components at a mass ratio of about 75:11:10 (e.g. 750 μg/ml polysorbate 80, 110 μg/ml TRITON™ X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC™ L12"). The emulsion can be formulated in phosphate buffered saline, pH 7.4. This emulsion is a useful delivery vehicle for muramyl dipeptides, and has been used with threonyl-MDP in the "SAF-1" adjuvant [59] (0.05-1% Thr-MDP, 5% squalane, 2.5% PLURONIC™ L121 and 0.2% polysorbate 80). It can also be used without the Thr-MDP, as in the "AF" adjuvant [60] (5% squalane, 1.25% PLURONIC™ L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'SPAN™ 80'). The emulsion is preferably thermoreversible and/or has at least 90% of the oil droplets (by volume) with a size less than 200 nm [61]. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 62, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN™ 80 or SPAN™ 80). Additives may be included, such as QuilA™ saponin, cholesterol, a saponin-lipophile conjugate (such as GPI-0100, described in reference 63, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [64].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [64].

An emulsion in which a saponin (e.g. QuilA™ or QS21) and a sterol (e.g. a cholesterol) are associated as helical micelles [65].

Antigens and adjuvants in a composition will typically be in admixture at the time of delivery to a patient. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

C. Saponin Formulations [Chapter 22 of Ref 57]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree has been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 66. Saponin formulations may also comprise a sterol, such as cholesterol [67].

Combinations of saponins and cholesterols can be used to form unique particles called immunostimulating complexes (ISCOMs; see chapter 23 of ref. 57; also refs 68 & 69). ISCOMs typically also include a phospholipid such as phosphatidylethanolamine or phosphatidylcholine. Any known saponin can be used in ISCOMs. Preferably, the ISCOM includes one or more of QuilA™, QHA & QHC. Optionally, the ISCOMS may be devoid of additional detergent [70].

A review of the development of saponin based adjuvants can be found in refs. 71 & 72.

D. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref 73. Such "small particles" of 3dMPL are small enough to be sterile filtered through a 0.22 μm membrane [73]. Other non-toxic LPS derivatives include monophosphoryl lipid A mimics, such as aminoalkyl glucosaminide phosphate derivatives e.g. RC-529 [74,75].

Lipid A derivatives include derivatives of lipid A from *Escherichia coli* such as OM-174. OM-174 is described for example in refs. 76 & 77.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 78, 79 and 80 disclose possible analog substitutions e.g. replacement of guanosine with 2'-deoxy-7-deazaguanosine. The adjuvant effect of CpG oligonucleotides is further discussed in refs. 81-86.

The CpG sequence may be directed to TLR9, such as the motif GTCGTT or TTCGTT [87]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 88-90. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 91-93.

A particularly useful adjuvant based around immunostimulatory oligonucleotides is known as IC-31™ [94-96]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 2). The polycationic polymer may be a peptide comprising 11-mer amino acid sequence KLKLLLLLKLK (SEQ ID NO: 3). This combination of SEQ ID NOs: 6 and 7 provides the IC-31™ adjuvant.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or *pertussis* ("PT"). The use of detoxified ADP-ribosylating toxins as mucosal adjuvants is described in ref 97 and as parenteral adjuvants in ref 98. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 99-106. A useful CT mutant is or CT-E29H [107]. Numerical reference for amino acid substitutions is preferably based on the alignments of the A and B subunits of ADP-ribosylating toxins set forth in ref 108, specifically incorporated herein by reference in its entirety.

E. Human Immunomodulators

Human immunomodulators suitable for use as adjuvants in the invention include cytokines, such as interleukins (e.g. IL-1, IL-2, IL-4, IL-5, IL-6, IL-7, IL-12 [109], etc.) [110], interferons (e.g. interferon-γ), macrophage colony stimulating factor, and tumor necrosis factor. A preferred immunomodulator is IL-12.

F. Bioadhesives and Mucoadhesives

Bioadhesives and mucoadhesives may also be used as adjuvants in the invention. Suitable bioadhesives include esterified hyaluronic acid microspheres [111] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [112].

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes (Chapters 13 & 14 of ref. 57)

Examples of liposome formulations suitable for use as adjuvants are described in refs. 113-115.

I. Imidazoquinolone Compounds.

Examples of imidazoquinolone compounds suitable for use adjuvants in the invention include Imiquamod and its homologues (e.g. "Resiquimod 3M"), described further in refs. 116 and 117.

The invention may also comprise combinations of aspects of one or more of the adjuvants identified above. For example, the following adjuvant compositions may be used in the invention: (1) a saponin and an oil-in-water emulsion [118]; (2) a saponin (e.g. QS21)+a non-toxic LPS derivative (e.g. 3dMPL) [119]; (3) a saponin (e.g. QS21)+a non-toxic LPS derivative (e.g. 3dMPL)+a cholesterol; (4) a saponin (e.g. QS21)+3dMPL+IL-12 (optionally +a sterol) [120]; (5) combinations of 3dMPL with, for example, QS21 and/or oil-in-water emulsions [121]; (6) SAF, containing 10% squalane, 0.4% TWEEN™ 80, 5% pluronic block PLURONIC™-block polymer L121, and thr-MDP, either microfluidized into a submicron emulsion or vortexed to generate a larger particle size emulsion. (7) RIBI™ adjuvant system (RAS), (RIBI™ Immunochem) containing 2% squalene, 0.2% TWEEN™ 80, and one or more bacterial cell wall components from the group consisting of monophosphorylipid A (MPL), trehalose dimycolate (TDM), and cell wall skeleton (CWS), preferably MPL+CWS (DETOX™); and (8) one or more mineral salts (such as an aluminum salt)+a non-toxic derivative of LPS (such as 3dMPL).

Other substances that act as immunostimulating agents are disclosed in chapter 7 of ref 57.

An aluminium hydroxide adjuvant is useful, and antigens are generally adsorbed to this salt. Oil-in-water emulsions comprising squalene, with submicron oil droplets, are also preferred, particularly in the elderly. Useful adjuvant combinations include combinations of Th1 and Th2 adjuvants such as CpG & an aluminium salt, or resiquimod & an aluminium salt. A combination of an aluminium salt and 3dMPL may be used.

Immunisation

In addition to providing immunogenic compositions as described above, the invention also provides a method for raising an immune response in a mammal, comprising administering an immunogenic composition of the invention to the mammal Typically, the immune response is an antibody response. The antibody response is preferably a protective antibody response. The invention also provides compositions of the invention for use in such methods.

The invention also provides a method for protecting a mammal against a bacterial infection and/or disease, comprising administering to the mammal an immunogenic composition of the invention.

The invention provides compositions of the invention for use as medicaments (e.g. as immunogenic compositions or as vaccines). It also provides the use of OMVs of the invention in the manufacture of a medicament for preventing a bacterial infection in a mammal.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

Efficacy of therapeutic treatment can be tested by monitoring bacterial infection after administration of the composition of the invention. Efficacy of prophylactic treatment can be tested by monitoring immune responses against immunogenic proteins in the vesicles or other antigens after administration of the composition. Immunogenicity of compositions of the invention can be determined by administering them to test subjects (e.g. children 12-16 months age) and then determining standard serological parameters. These immune responses will generally be determined around 4 weeks after administration of the composition, and compared to values determined before administration of the composition. Where more than one dose of the composition is administered, more than one post-administration determination may be made.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

BRIEF DESCRIPTION OF DRAWINGS

FIG. 5 FIGS. 5A-B: show the results from the Western blots for Bla (FIG. 5A) and fHbp (FIG. 5B). Empty OMVs were also loaded as a negative control. Comparing the chemiluminescence signals with those from the known amounts of purified proteins, demonstrated that 30 µg of OMVs contain approximately 240 ng Bla.

MODES FOR CARRYING OUT THE INVENTION

Figure 1:
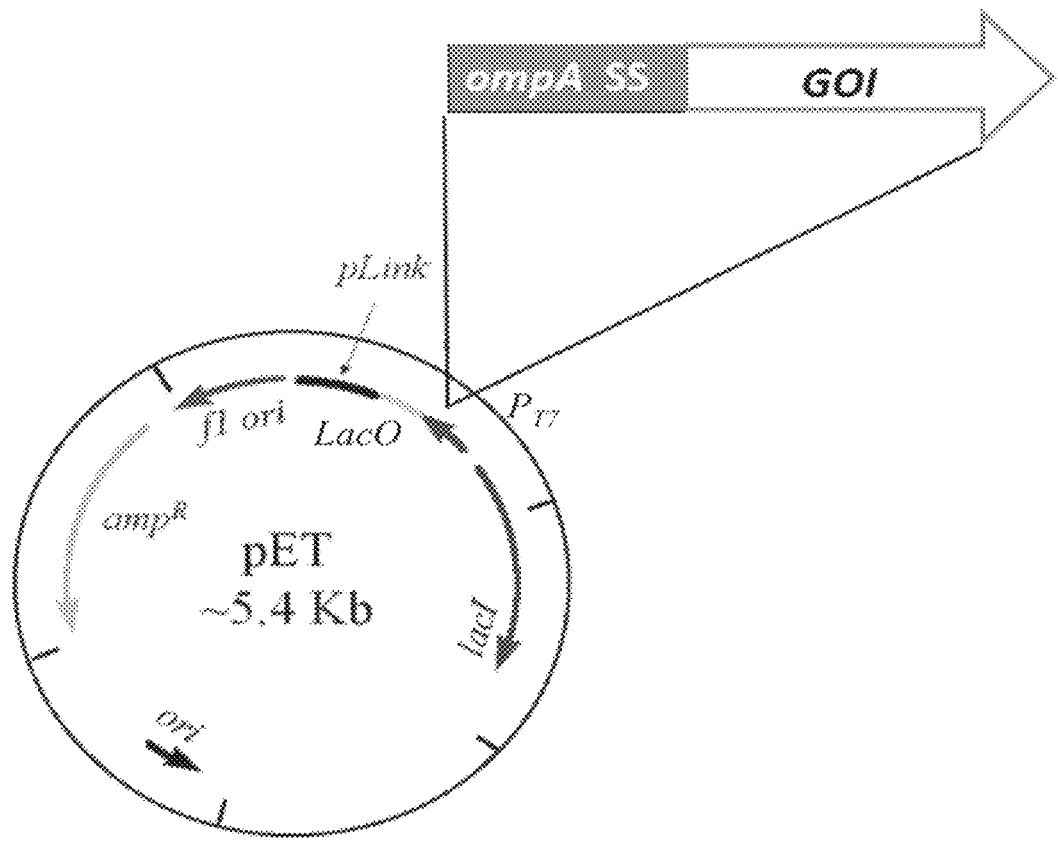
FIG. 1: shows a map of pET-OmpA plasmid, which is a pET21b-derivative plasmid containing the nucleic acid sequence encoding the E. coli OmpA signal sequence (SS) fused to a gene of interest (GOI) encoding a heterologous protein. The OmpA LS targets the protein encoded by the GOI into the lumen of OMVs.

Example 1—Expression of Heterologous Proteins into *E. coli* OMVs

Generation of *E. coli* BL21(DE3) ΔtolR and ΔompA ko Mutants

Recombination-prone BL21(DE3) cells were produced by using the highly proficient homologous recombination system (red operon) [122]. Briefly, electrocompetent bacterial cells were transformed with 5 μg of plasmid pAJD434 by electroporation (5.9 ms at 2.5 kV). Bacteria were then grown for 1 h at 37° C. in 1 ml of SOC broth and then plated on Luria-Bertani (LB) plates containing trimethoprim (100 μg/ml). Expression of the red genes carried by pAJD434 was induced by adding 0.2% L-arabinose to the medium.

ΔtolR and ΔompA *E. coli* BL21 mutant strains, which are known to spontaneously produce a large amount of OMVs, were produced by replacing ompA and tolR coding sequences with kanamycin (kmr) and chloramphenicol (cmr) resistance cassettes, respectively. A three-step PCR protocol was used to fuse the upstream and downstream regions of ompA and tolR to the kmr and cmr genes, respectively. Briefly, the upstream and downstream regions of the tolR and ompA gene were amplified from BL21(DE3) genomic DNA with the specific primer pairs tolR-1/tolR-2 and tolR-3/tolR-4; ompA-1/ompA-2 and ompA-3/ompA 4, respectively (Table 1). The kmr cassette was amplified from plasmid pUC4K using the primers PUC4K-rev and PUC4K-for and cmr was amplified using primers CMR-for/CMR-rev. Finally, 100 ng of each of the three amplified fragments were fused together by mixing in a PCR containing the ¼ primers.

Linear fragments in which the antibiotic resistance gene was flanked by the tolR/ompA upstream and downstream regions were used to transform the recombination-prone BL21(DE3) *E. coli* strain, which was made electrocompetent by three washing steps in cold water. Transformation was by an electroporation of 5.9 ms at 2.5 kV. Transformants were selected by plating the cells on LB plates containing 30 μg/ml of kanamycin or 20 μg/ml chloramphenicol. The deletion of the tolR and ompA genes was confirmed by PCR-amplification of genomic DNA using primers pairs tolR-1/PUC4K-rev and PUC4K-for/tolR-4; ompA-1/CMR-rev and CMR-for/ompA-4.

TABLE 1

Oligonucleotide primers:

| Name | Sequence | SEQ ID NO |
|---|---|---|
| GAS25-F | ACCGTAGCGCAGGCCAACAAACAAAACACTGCTAGTACAG | 4 |
| GAS25-R | GTGATGGTGATGTTACTACTTATAAGTAATCGAACCATATG | 5 |
| SpyCEP-F3 | ACCGTAGCGCAGGCCGCAGCAGATGAGCTAAGCACAATGAGCGAACC | 6 |
| SpyCEP-R3 | GTGATGGTGATGTTATTAGGCTTTTGCTGTTGCTGAGGTCGTTGACTTGGTTGG | 7 |
| Bla-omp-F | ACCGTAGCGCAGGCCCGGTAAGATCCTTGAGATTTTTCG | 8 |
| Bla-omp-R | GTGATGGTGATGTTATTACCAATGCTTAATCAGTGAGGC | 9 |
| fHbp-F | ACCGTAGCGCAGGCCGTCGCCGCCGACATCG | 10 |
| fHbp-R | GTGATGGTGATGTTATTATTGCTTGGCGGCAAGGC | 11 |
| omprev | GGCCTGCGCTACGGTAGCGAAA | 12 |
| nohisflag | TAACATCACCATCACCATCACGATTACAAAGA | 13 |
| tolR-1 | TCTGGAATCGAACTCTCTCG | 14 |
| tolR-2 | ATTTTGAGACACAACGTGGCTTTCATGGCTTACCCCTTGTTG | 15 |
| tolR-3 | TTCACGAGGCAGACCTCATAAACATCTGCGTTTCCCTTG | 16 |
| tolR-4 | TTGCTTCTGCTTTAACTCGG | 17 |
| ompA-1 | GATCGGTTGGTTGGCAGAT | 18 |

TABLE 1-continued

Oligonucleotide primers:

| Name | Sequence | SEQ ID NO |
|---|---|---|
| ompA-2 | CACCAGGATTTATTTATTCTGCGTTTTGCGCCTCGTTATCAT | 19 |
| ompA-3 | TACTGCGATGAGTGGCAGGCGCAGGCTTAAGTTCTCGTC | 20 |
| ompA-4 | AAAATCTTGAAAGCGGTTGG | 21 |
| PUC4K-rev | AAAGCCACGTTGTGTCTC | 22 |
| PUC4K-for | TGAGGTCTGCCTCGTGAA | 23 |
| CMR-for | CGCAGAATAAATAAATCCTGGTG | 24 |
| CMR-rev | CCTGCCACTCATCGCAGTA | 25 |
| Spy0269-F | ACCGTAGCGCAGGCCGATGATAGAGCCTCAGGAGAAACG | 26 |
| Spy0269-R | GTGATGGTGATGTTATCACTTAGATTCCTTACGGAACC | 27 |
| Spy0269-fus3 | GATTACTTATAAGTAGAGAAGGAGATATACATATGAAAAAGACAGC | 28 |
| Slo-fus-F | AACAAACAAAACACTGCTAGTACAG | 29 |
| Slo-fus-R3 | TATACTCCTTCTCTACTTATAAGTAATCGAACCATATG | 30 |
| Spy0269-fus-R | TCACTTAGATTCCTTACGGAACC | 31 |
| Spycep-fus-F | AAGGAATCTAAGTGAGAAGGAGATATACATAGTGAGAATGAAAAAGACAGC | 32 |

Example 2—Plasmid Construction

Five heterologous proteins from different bacterial species, both Gram positive and Gram-negative, and belonging to different cellular compartments were selected as model proteins to determine whether heterologous proteins can be incorporated into E. coli OMVs in their native conformations. These proteins included: (1) the periplasmic TEM1 beta lactamase (Bla) from E. coli, (2) the factor H-binding protein (fHbp) lipoprotein from Neisseria meningitidis, (3) the extracellular cholesterol depending streptolysin O (Slo also called GAS25) from Streptococcus pyogenes, (4) the cell envelope serine protease SpyCEP (also called GAS57) from Streptococcus pyogenes and (5) the putative surface exclusion protein Spy0269 (also known GAS40) also from Streptococcus pyogenes. The nucleic acid coding sequences for each of these five proteins were cloned into the pET-OmpA plasmid using the polymerase incomplete primer extension (PIPE) cloning method [123]. The pET-OmpA plasmid (as provided in e.g. [124] and [125]) is a pET21b-derived plasmid.

Briefly, Slo-dm (slo double mutant, SEQ ID:42) was PCR-amplified from plasmid pET21-Slo-dm, which contains the slo-dm gene, using the GAS25-F/GAS25-R primers (see Table 1). The SpyCEP gene (a double mutant sequence is also provided as SEQ ID:40) was PCR-amplified from the M1 GAS strain ISS3348 using SpyCEP-F3/SpyCEP-R3 primers, which were designed to exclude the C-terminal LPXTG motif cell-wall anchor (located at aa 1614-1647). The spy0269 (SEQ ID:44) gene was PCR amplified from the M1 GAS strain ISS3348 using spy0269-F/spy0269-R primers. Primers for fHbp gene amplification were designed to exclude the lipobox (which is located at aa 17-25 in fHbp) in order to avoid membrane anchoring. In order to target the proteins to the periplasm, the sequences encoding the signal sequences of each of these proteins was removed and replaced with the E. coli OmpA signal sequence (SS) (see FIG. 1). Bla and fHbp were amplified from pET21b and Neisseria meningitidis MC58 genome respectively using primers Bla-omp-F/Bla-omp-R and fHbp-F/fHbp-R, respectively. pET-OmpA plasmid was amplified by PCR using primers omprev/nohisflag. In this way plasmids pET-21_Bla (SEQ ID:37), pET-21_slo (SEQ ID:33), pET-21_SpyCEP (SEQ ID:34), pET-21_fHbp (SEQ ID:36) and pET21_spy0269 (SEQ ID:35) were generated.

Example 3—Expression of the Heterologous Proteins into ΔtolR and ΔompA Mutants, OMVs and Total Lysates Preparation In order to investigate whether the Bla, slo, SpyCEP, fHbp and Spy0269 proteins are packaged into OMVs, the ΔtolR and ΔompA E. coli BL21 strains were transformed with the pET-21_Bla, pET-21_slo, pET-21_SpyCEP, pET-21_fHbp plasmids and pET21_spy0269. As a negative control, the ΔtolR and ΔompA E. coli BL21 strains were transformed with the pET-OmpA empty vector.

Figure 2:
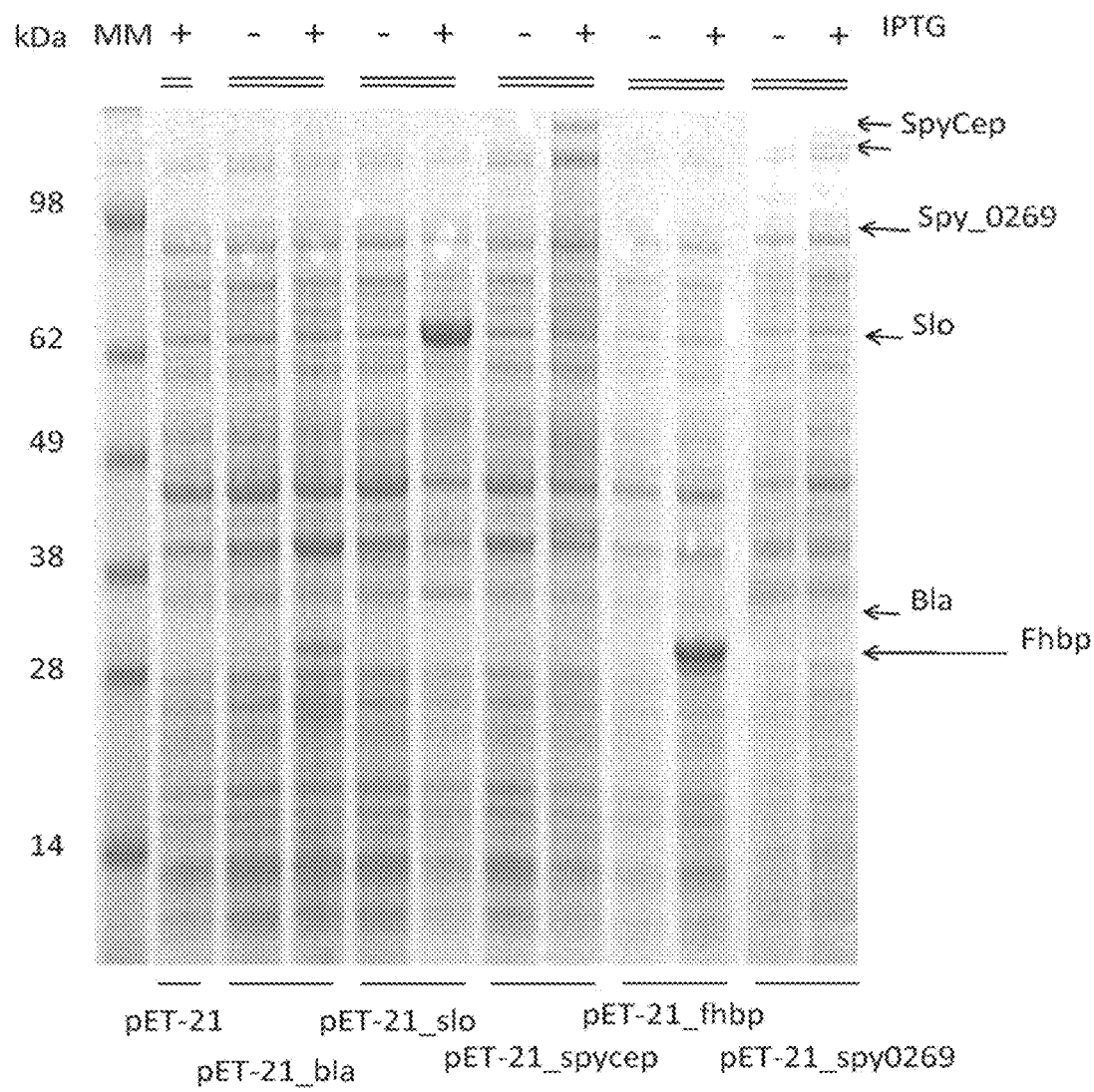
FIG. 2: shows the results of SDS-polyacrylamide gel electrophoresis (SDS-PAGE) of total lysates of cultures before and after induction with 1 mM IPTG. Bands corresponding to SpyCEP, Slo, Bla, fHbp and Spy0269 are highlighted by arrows.

All the strains were grown in liquid cultures until logarithmic phase and induction of expression of the genes was carried out by adding 1 mM IPTG (isopropyl-beta-D-thio-galactopyranoside). FIG. 2 shows the SDS-polyacrylamide gel electrophoresis (SDS-PAGE) of total lysates of these cultures before and after induction with 1 mM IPTG. Bands corresponding to Bla, slo, SpyCEP, fHbp and Spy0269 proteins are present in all induced samples and are indicated by arrows. Thus, all five of the tested heterologous proteins were successfully induced in E. coli.

Figure 3:
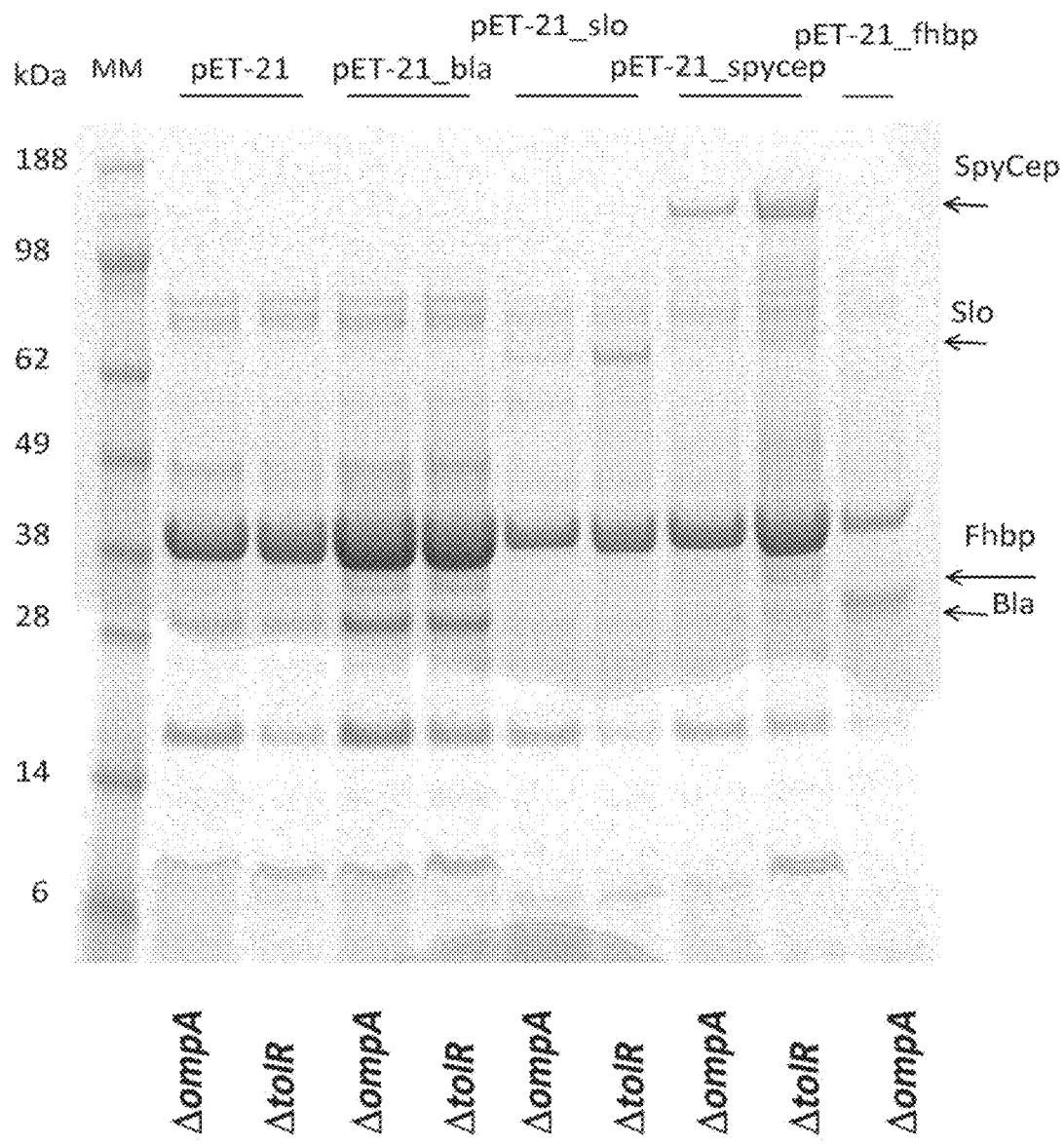
FIG. 3: shows an SDS-PAGE of 30 µg OMVs prepared by ultracentrifugation of culture supernatant of the transformed ΔtolR and ΔompA strains. Bands corresponding to the weight of SpyCEP, Slo, Bla and fHbp are indicated by arrows.

Using an overnight culture of each transformant, 200 ml of LB medium was inoculated at $OD_{600}$=0.05. Cultures were grown until the $OD_{600}$=0.5 and then expression of the recombinant proteins was induced by addition of 1 mM IPTG, followed by a further incubation of 2 hours. For OMV preparations, cells were harvested by centrifugation at 8,000×g for 20 minutes. The resulting supernatant was filtered through a 0.22 μm pore size filter (Millipore). The filtrates were then subjected to high speed centrifugation (200,000×g for 2 hours) and the pellets containing the OMVs were resuspended in PBS with protease inhibitors (Roche). For mice immunization, when indicated, OMVs were sonicated in a hypotonic buffer (10 mM Tris pH 7.5, 1.5 mM $MgCl_2$, 10 mM KCl) by 10 bursts of 30 seconds each, followed by cooling on ice. Total lysates were prepared from 1 ml of culture, which was centrifuged at 13,000×g for 5 minutes. The pellet was resuspended in SDS-PAGE sample loading buffer, heated at 100° C. for 5 minutes and loaded onto a 4-12% polyacrylamide gel (Invitrogen). Gels were run in MES buffer (Invitrogen) and stained with Comassie Blue. FIG. 3 shows the polyacrylamide gels for approximately 30 mg OMVs obtained from ΔtolR and ΔompA strains which contain plasmids to express the different heterologous proteins. Bands corresponding to the weight of SpyCEP, Slo, Bla and fHbp are indicated by arrows. To confirm protein identification, the bands were excised and digested with trypsin and the resulting proteolytic peptides were then analysed by matrix-assisted laser desorption ionization—time of flight (MALDI-TOF).

Briefly, protein bands were excised from the gels, washed with 50 mM ammonium bicarbonate-acetonitrile (50/50, vol/vol), and air dried. Dried spots were digested for 2 h at 37° C. in 12 µl of 0.012-µg/µl sequencing-grade modified trypsin (sequencing grade modified porcine trypsin; Promega, Madison, Wis.) in 5 mM ammonium bicarbonate. After digestion, 0.6 µl of the digested product was loaded on a matrix-prespotted Anchorchip (PAC 384 HCCA; Bruker-Daltonics, Bremen, Germany) and air-dried. Spots were washed with 0.6 µl of a solution containing 70% ethanol and 0.1% trifluoroacetic acid. Mass spectra were acquired with an ultraflex MALDI-TOF mass spectrometer (Bruker-Daltonics). Spectra were externally calibrated by using the combination of standards present on the PAC chip (Bruker-Daltonics). Monoisotopic peptide matching and protein searching were performed automatically using a licensed version of the MASCOT software (Matrix Sciences, London, United Kingdom) run on a local database. The MASCOT search parameters used were as follows: (i) allowed number of missed cleavages=1; (ii) variable posttranslational modification=methionine oxidation; and (iii) peptide tolerance=100 ppm. Only significant hits, as defined by MASCOT probability analysis, were considered. The MASCOT software identified the bands as corresponding to Bla, Slo, SpyCEP and fHbp proteins respectively. These results confirm that Bla, Slo, SpyCEP and fHbp can all be expressed and incorporated into OMVs produced both by ΔtolR and ΔompA E. coli strains.

Example 4—Quantification of Heterologous Proteins into OMVs

In order to quantify the amount of heterologous proteins incorporated in the E. coli OMVs, Western blot analysis was performed.

30 µg OMVs containing the heterologous proteins were loaded onto 4-12% SDS-polyacrylamide gels along with increasing concentration (20-80 ng) of the corresponding purified protein. Empty OMVs were also loaded as a negative control. The polyacrylamide gels were then transferred onto nitrocellulose filter by standard methods [126]. The filters were blocked overnight at 4° C. by agitation in blocking solution (10% skimmed milk and 0.05% TWEEN™ in PBS), followed by incubation for 90 minutes at 37° C. with a 1:1000 dilution of the required antibody (anti-Bla (Abcam), anti-slo, anti-SpyCEP and anti-fHbp) in 3% skimmed milk and 0.05% TWEEN™ in PBS. After three washing steps in PBS-TWEEN™, the filters were incubated in a 1:2000 dilution of peroxidase-conjugated anti-mouse immunoglobulin (Dako) in 3% skimmed milk and 0.05% TWEEN™ in PBS for an hour, and after three washing steps, the resulting signal was detected by using the SuperSignal West Pico chemiluminescent substrate (Pierce).

Figure 4A:
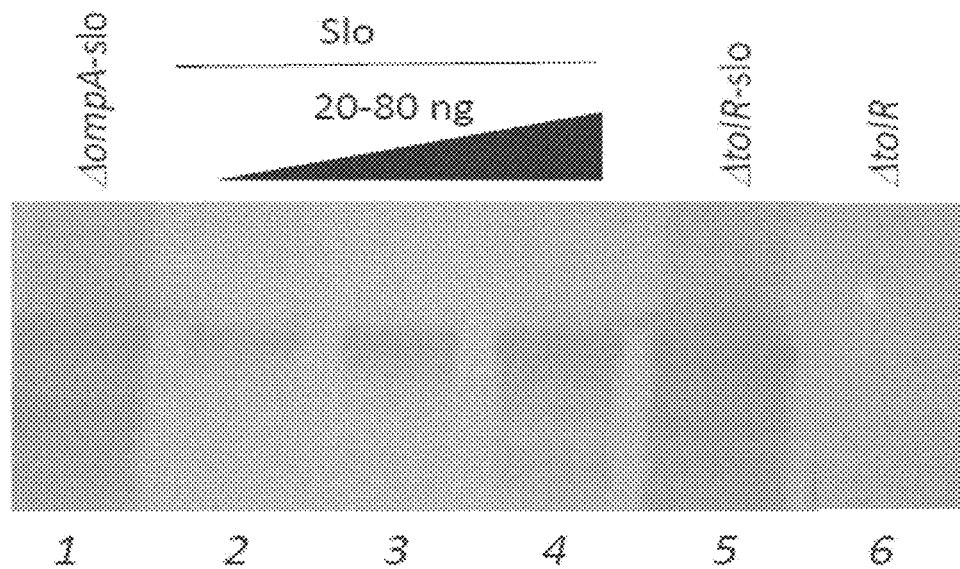
FIGS. 4A-B: show the results from the Western blots for Slo (FIG. 4A) and SpyCEP (FIG. 4B). Empty OMVs were also loaded as a negative control. Comparing the chemiluminescence signals with those from the known amounts of purified proteins, demonstrated that 30 µg of OMVs contain approximately 240 ng Slo-dm, 240 ng SpyCEP.
Figure 4B:
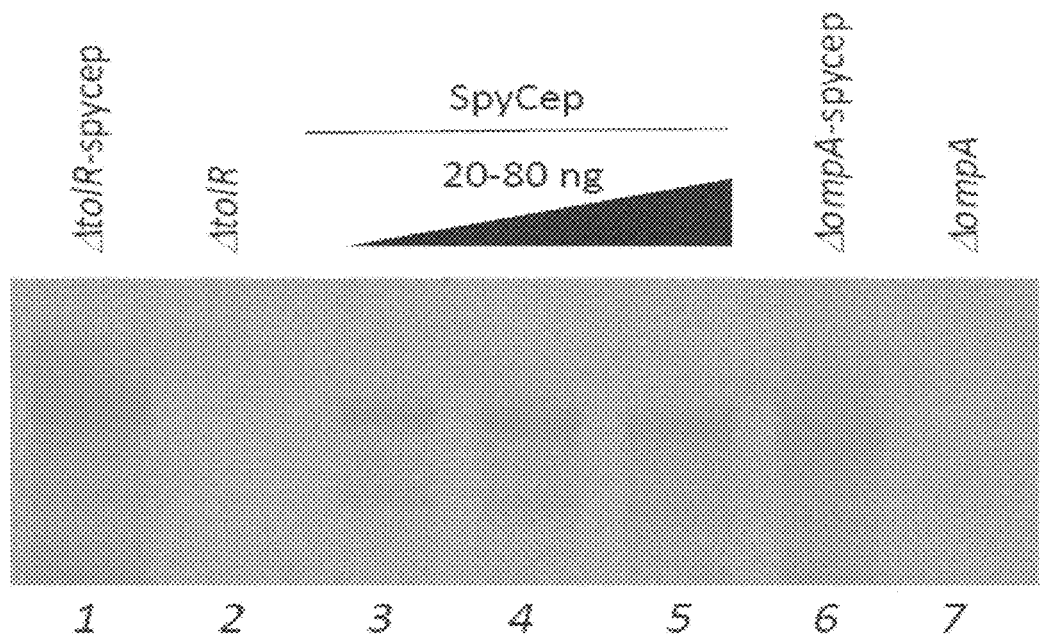
Figure 5A:
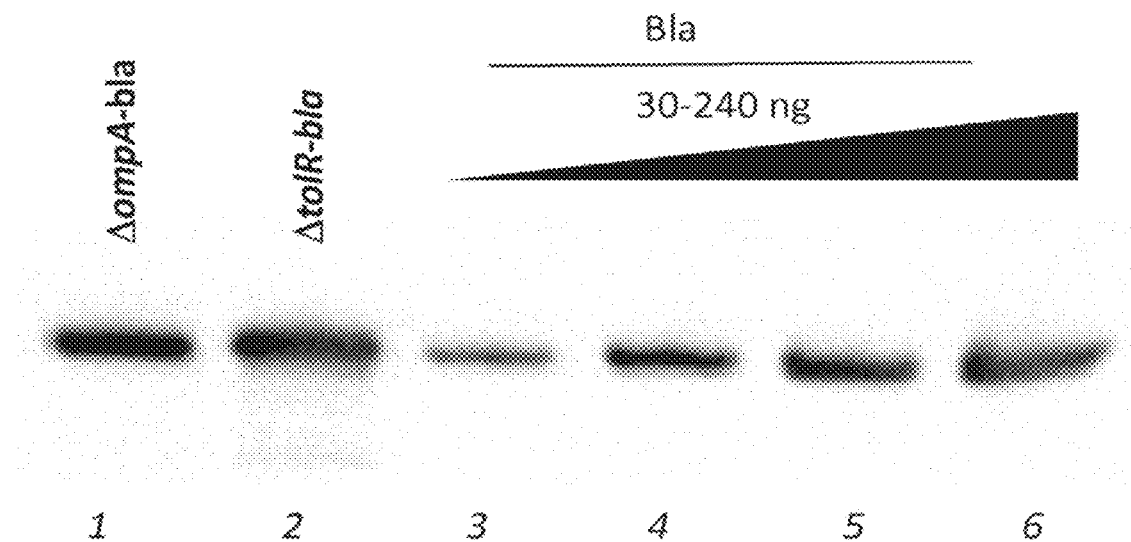
Figure 5B:
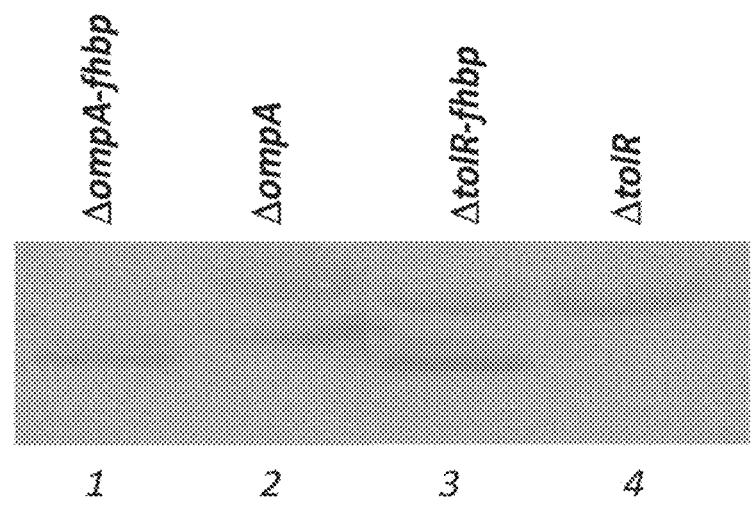

FIG. 4 and FIG. 5 show the results from the four different Western blots performed. As expected from the MALDI-TOF analysis, all the OMV preparations contain the heterologous proteins selected. Comparing the chemiluminescence signals with those from the known amounts of purified proteins, demonstrated that 30 mg of OMVs contain approximately 240 ng of Slo, SpyCEP and Bla.

Example 5—Heterologous Proteins are Localized in the OMVs Periplasm

As described above, the signal sequences of all four of the heterologous proteins were replaced by the E. coli OmpA signal sequence in order to target the proteins into the E. coli periplasm. It was therefore important to confirm that the proteins are expressed as luminal components of OMVs rather than attached to the extracellular surface of OMVs.

In order to test this, 100 µg/ml proteinase K (Fermentas) was added to 15 µg intact and solubilized (in 1% SDS) OMVs expressing Slo-dm or SpyCEP, and the mixture was then incubated at 37° C. for 10 minutes. After proteinase K deactivation with 10 mM phenylmethylsulfonyl fluoride (PMSF; Sigma Aldrich) samples were loaded on a 4-12% polyacrylamide gel and Western blot analysis was performed with the required antibody to detect the presence of the heterologous proteins.

Figure 6A:
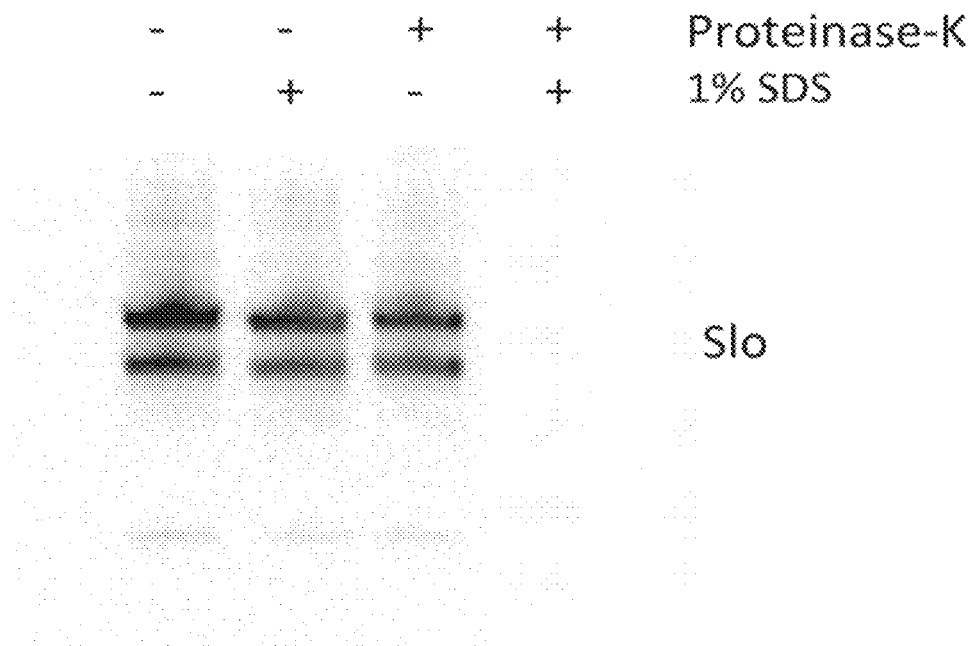
FIGS. 6A-B: show Western blots showing that the Slo (FIG. 6A) and SpyCEP (FIG. 6B) are expressed as luminal components of OMVs, rather than attached to their extracellular surface. 100 µg/ml proteinase K was added to 15 µg intact and solubilized (in 1% SDS) vesicles expressing Slo or SpyCEP and incubated at 37° C. 10 minutes. Protein degradation was detected by Western blot analysis.
Figure 6B:
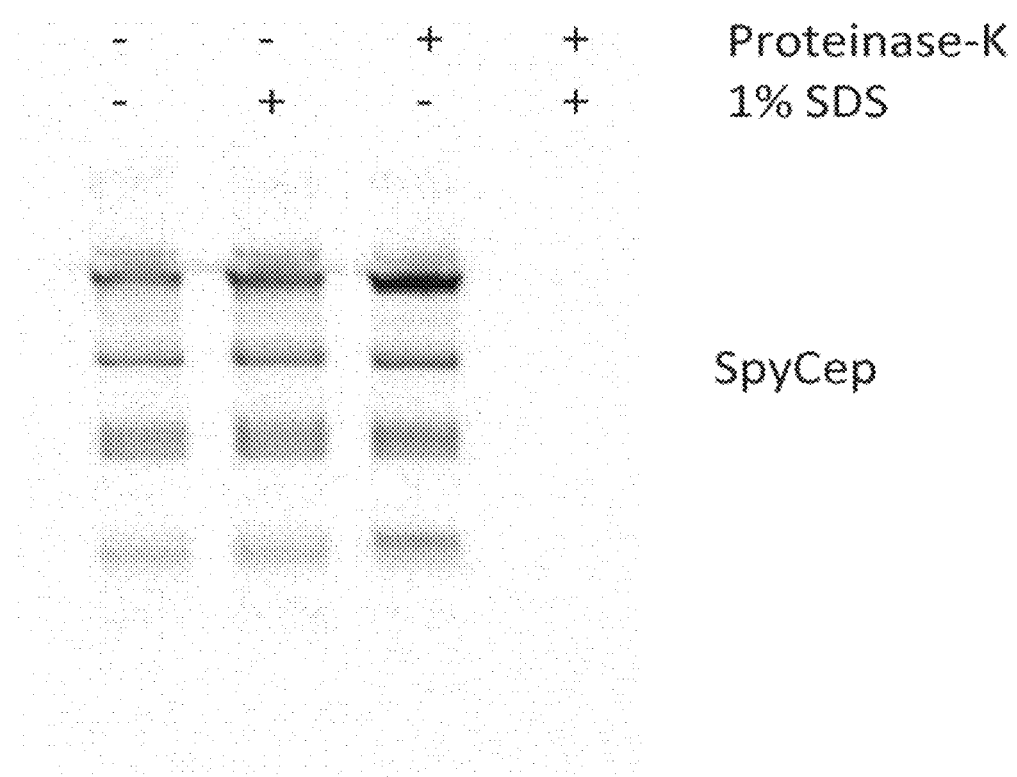
Figure 7:
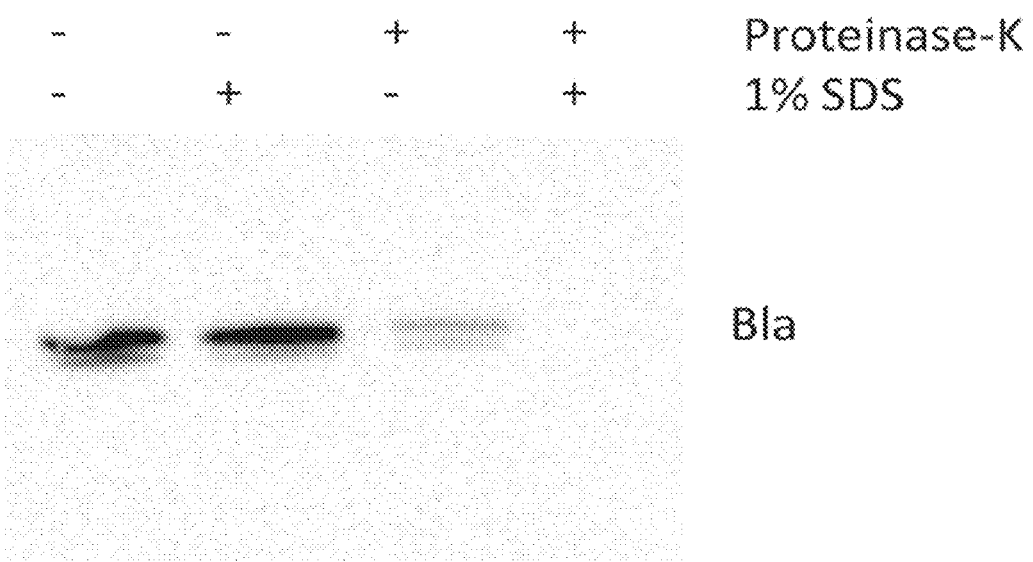
FIG. 7: shows a Western blot showing that Bla is expressed as a luminal component of OMVs, rather than attached to their extracellular surface. 100 µg/ml proteinase K was added to 15 µg intact and solubilized (in 1% SDS) OMVs expressing Bla and incubated at 37° C. 10 minutes. Protein degradation was detected by Western blot analysis.

FIG. 6 and FIG. 7 show that Slo-dm, SpyCEP and Bla were all protected from proteinase K-mediated degradation in unsolubilised OMVs (but not in solubilized OMVs), demonstrating than they are both expressed as periplasmic proteins in the lumen of E. coli OMVs.

Example 6—OMVs Containing SpyCEP are Able to Hydrolyse IL-8

Figure 8A:
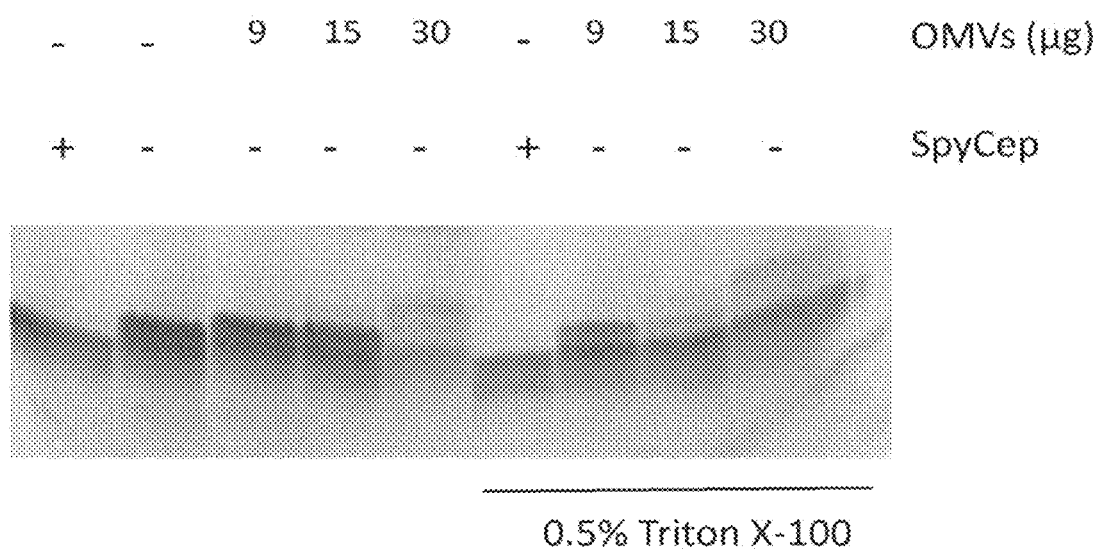
FIG. 8A: shows SpyCEP activity of SpyCEP-containing OMVs which have been solubilized with 0.5% TRITON™ X-100. OMVs expressing the SpyCep protein were incubated at different concentration with 50 µg/ml IL-8 at 37° C. for 2 hours. SpyCep wild type protein was used as positive control at 10 µg/ml and hydrolysis of IL-8 was analyzed by SDS-PAGE.
Figure 8B:
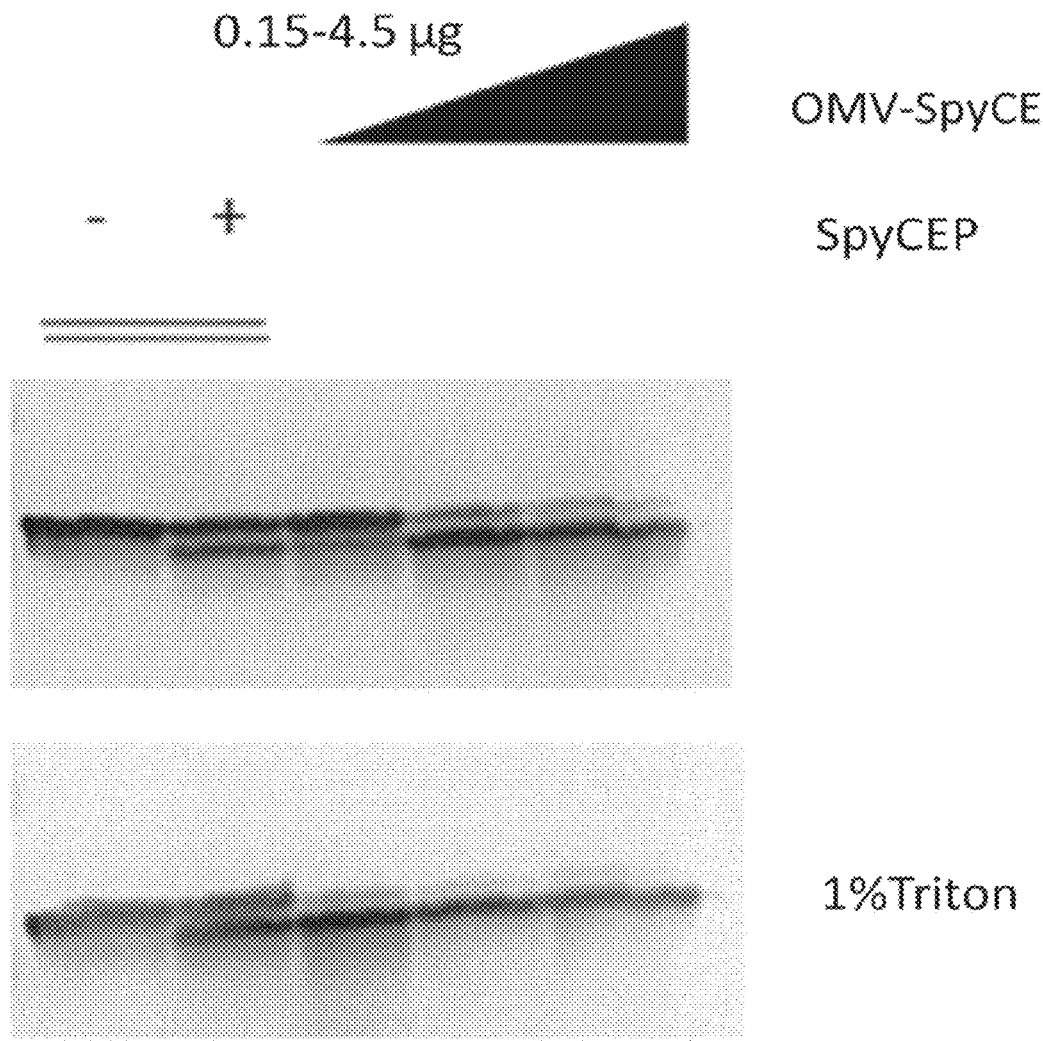
FIG. 8B: shows SpyCEP activity of SpyCEP-containing OMVs which have been solubilized with 1% TRITON™ X-100. OMVs expressing the SpyCep protein were incubated at different concentration with 50 µg/ml IL-8 at 37° C. for 2 hours. SpyCep wild type protein was used as positive control at 10 µg/ml and hydrolysis of IL-8 was analyzed by SDS-PAGE.

SpyCEP has been reported to hydrolyse IL-8, converting it into a 6-kDa inactive fragment [127]. To determine whether SpyCEP maintains this hydrolytic activity in the OMV preparation, OMVs expressing the SpyCEP protein were incubated at different concentrations with human IL-8 (50 µg/ml) at 37° C. for 2 hours. The SpyCEP wild type protein (at a concentration of 10 µg/ml) was used as positive control. IL-8 was incubated with 10 ng/ml GAS57 purified protein (which is known to hydrolyse IL-8), as a positive control. The hydrolytic products were analysed using an 18% SDS-PAGE with silver staining. In order to test whether an active form of the SpyCEP protein is located inside the OMVs, leakage of SpyCEP from the OMV lumen was induced by permeabilising the OMVs in 0.5% TRITON™ X-100 at room temperature for 20 minutes (see FIG. 8A). An additional experiment was conducted in which the OMVs were permeabilised using 1% TRITON™ X-100 (see FIG. 8B), As shown in FIGS. 8A and 8B, IL-8 was almost completely cleaved after 2 hours incubation with 30 µg OMVs containing SpyCEP. Thus, SpyCEP's biological activity is preserved in OMVs. Retention of functional activity indicates that the heterologous protein is correctly folded in the OMV and will therefore display the same or substantially the same structural epitopes as the wild-type protein in its native environment. The IL-8 hydrolysis activity was increased in permeabilised OMVs, suggesting that an active form of SpyCEP is located inside OMVs. Retention of functional activity indicates that the heterologous protein is correctly folded in the OMV and will therefore display the same or substantially the same antigens as the wild-type protein in its native environment.

Example 7—OMVs Containing Bla and Slo

OMVs expressing Bla were incubated with the chromogenic substrate nitrocefin and the Bla activity was measured as described herein. OMV preparations were incubated with nitrocefin (0.5 mg/ml; Oxoid, Thermo Scientific, Cambridge, United Kingdom) for 30 min at 37° C. in the dark. The chromogen hydrolysis and subsequent color change of supernatants were determined immediately with the Tecan spectrophotometer at OD485. The enzymatic activity was estimated using a standard curve, where OD485 was related to the amount of nitrocefin hydrolyzed. This was quantified using recombinant β-lactamase (VWR).

Figure 9A:
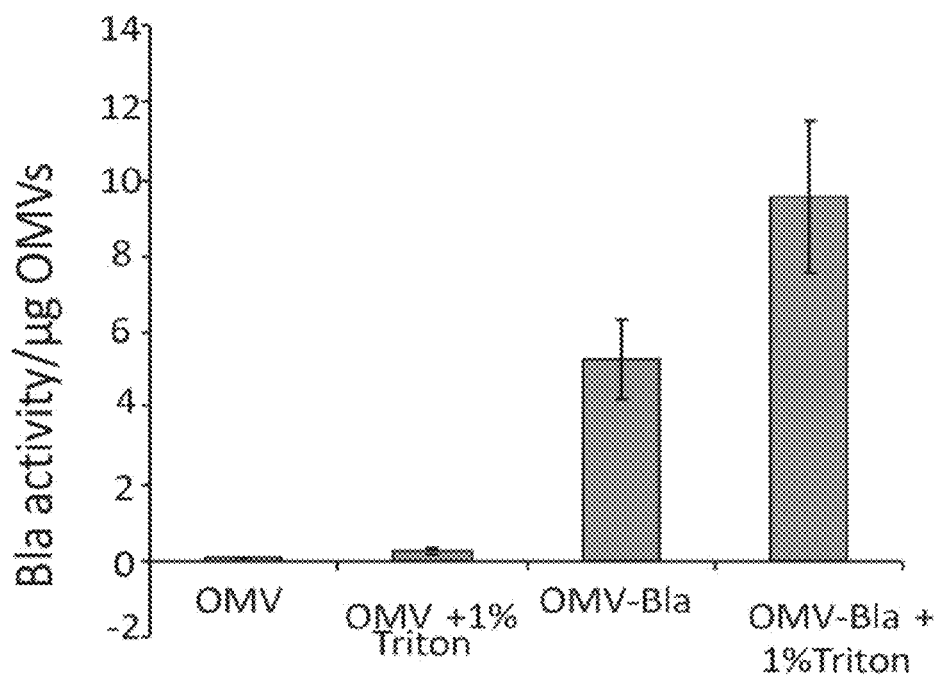
FIG. 9A: shows the Bla activity of Bla-containing OMVs and empty OMVs. OMV preparations were incubated with nitrocefin (0.5 mg/ml; Oxoid, Thermo Scientific, Cambridge, United Kingdom) for 30 min at 37° C. in the dark. The chromogen hydrolysis and subsequent color change of supernatants were determined immediately with the Tecan spectrophotometer at $OD_{485}$. The enzymatic activity was estimated using a standard curve, where $OD_{485}$ was related to the amount of nitrocefin hydrolyzed. This was quantified using recombinant β-lactamase (VWR).

FIG. 9A shows that empty OMVs showed no Bla activity, whereas Bla activity was shown in Bla-containing OMVs. Hence, the biological activity of Bla is preserved in OMVs.

In order to test whether an active form of the Bla is located inside the OMVs, leakage of Bla from the OMV lumen was induced by permeabilising the OMVs in 1% TRITON™ X-100 at room temperature for 20 minutes. As shown in FIG. 9A, Bla activity was increased in permeabilised OMVs, suggesting that an active form of Bla is located inside OMVs.

Slo hemolytic activity was tested by incubating OMVs expressing the wild type (wt) form of the toxin with sheep blood erythrocytes, using the following method. Serial dilutions of the samples were prepared in 96-well plates with U-shaped bottoms using PBS+0.5% BSA as dilution buffer. 1 ml of sheep blood was washed three times in PBS (with centrifugation at 3000×g), and blood cells were finally suspended in 5 ml of PBS. 50 µl of this suspension was added to 50 µl of each diluted samples and incubated at 37° C. for 30 min. Water was used to give 100% haemolysis, and PBS+BSA 0.5% was used as negative control. Plates were then centrifuged for 5 min at 1,000×g, and the supernatant was carefully transferred to 96-well flat-bottomed plates to read the absorbance at 540 nm [128].

Figure 9B:
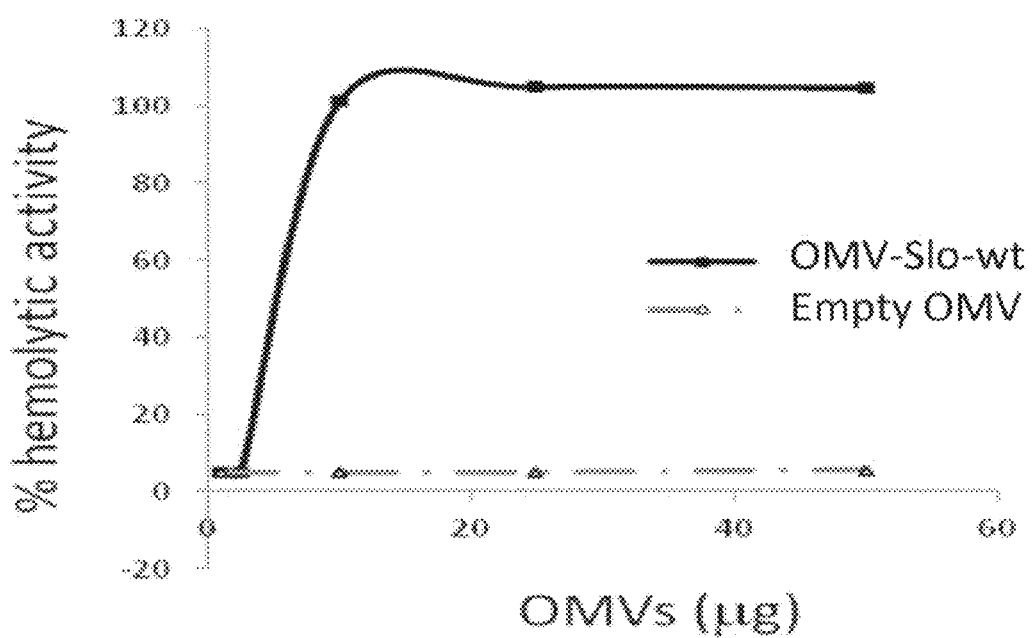
FIG. 9B: shows the hemolytic activity, expressed as is the ratio between the absorbance (OD 540 nm) of blood incubated with OMVs and the absorbance of blood incubated with water (100% hemolysis), of wild type (wt) Slo-containing OMVs and empty OMVs when incubated with sheep blood erythrocytes.

As shown in FIG. 9B, negative control empty OMVs showed no hemolytic activity, whereas Slo-wt containing OMVs show high levels of hemolytic activity, which was dependent on the amount of OMVs present. Hence, the biological activity of Slo is preserved in OMVs. Retention of functional activity of Slo and Bla indicates that these heterologous proteins are correctly folded in the OMV and will therefore display the same or substantially the same antigens as the wild-type protein in its native environment.

Example 8—Antibody Titers Elicited in Mice Immunized with Slo and SpyCEP in Engineered OMVs To examine the immunogenicity of Slo and SpyCEP in *E. coli* OMVs, groups of 8 CD1 5-week old female mice were immunized intraperitoneally on days 0, 21 and 35 with 25 µg of sonicated or unsonicated OMVs over-expressing the Slo or SpyCEP proteins. All samples were formulated with 2 mg/ml alum hydroxide as adjuvant. Control mice were immunized with PBS and adjuvant. Positive control groups consisted of mice immunized with 20 µg of recombinant purified Slo or SpyCEP proteins. To test the OMVs adjuvanticity, mice were also immunized with 25 µg of empty OMVs or with 25 µg of empty OMVs plus 20 µg of Slo or SpyCEP antigen.

Sera were collected before the first immunization (pre-immune sera) and after each of the 3 immunizations (post1, post2 and post3 sera), and ELISA titers were analysed. ELISAs were performed using 96-well Maxisorp plates (Nunc, Thermo Fisher Scientific) coated with 3 µg/ml or 2 µg/ml of Slo or SpyCEP protein, respectively, in PBS. Plates were incubated for 2 h at room temperature, then washed three times with TPBS (0.05% TWEEN™ 20 in PBS, pH 7.4) and blocked with 250 µl/well of 2% BSA (Sigma-Aldrich) for 1 h at room temperature. Each incubation step was followed by triple TPBS wash. Serum samples were initially diluted 1:500-1:1000 in 2% BSA in TPBS, transferred onto coated-blocked plates (200 µE) and serially diluted (by two-fold) followed by 2 h incubation at 37° C. Then 100 µl/well of 1:2000 diluted alkaline phosphatase-conjugated goat anti-mouse IgG were added and left for 2 h at 30° C. Bound alkaline phosphatase was visualized by adding 100 µl/well of 3 mg/mL para-nitrophenyl-phosphate disodium hexahydrate (Sigma-Aldrich) in 1 M diethanolamine buffer (pH 9.8). After 10 min of development at room temperature, plates were analysed at 405 nm in a microplate spectrophotometer. Antibody titres were calculated by interpolating ODs onto a reference calibration curve, and expressed in ELISA units (EU) per mL.

Figure 10A:
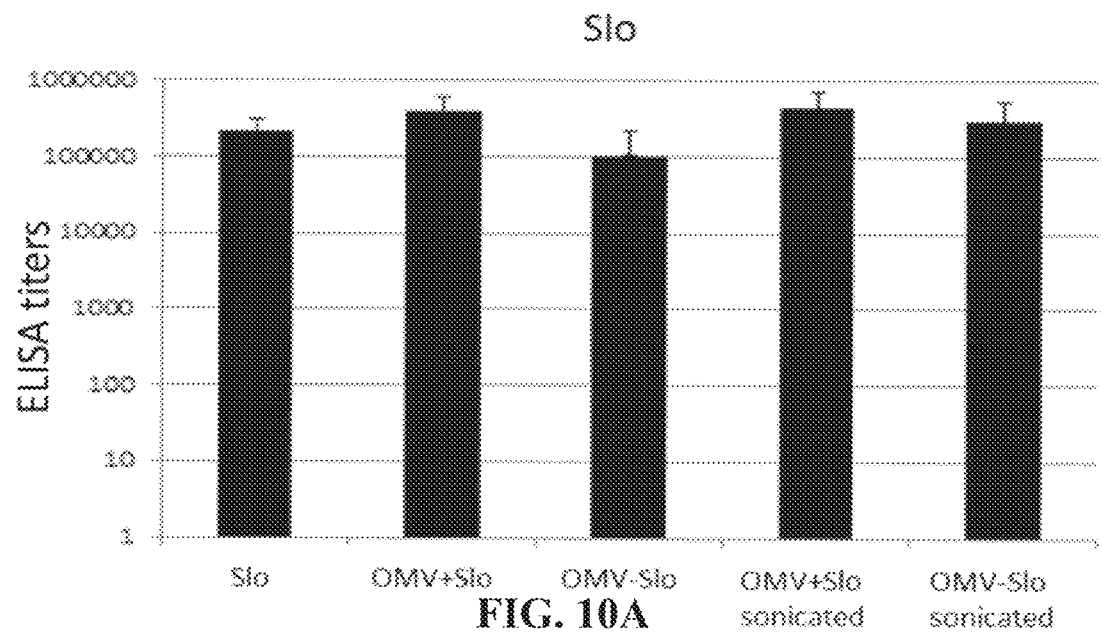
FIGS. 10A-B: show the geometric mean of the ELISA titers obtained from the 8 mice for each group of Slo (FIG. 10A) and SpyCEP (FIG. 10B) immunizations after the third immunization (day 49).
Figure 10B:
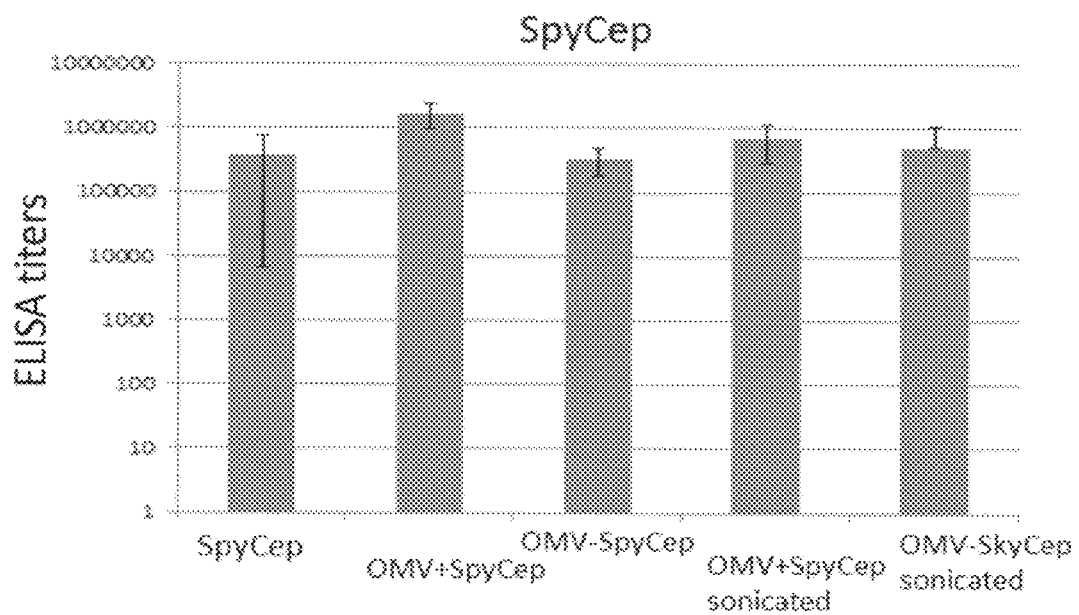

FIG. 10 shows the geometric mean of the ELISA titers obtained from the 8 mice for each group of immunizations after the third immunization (day 49). Sera from mice immunized with PBS and adjuvant alone or with empty OMVs gave negative results. As shown in FIG. 10, the antibody response to all five preparations was statistically equivalent, suggesting that engineered OMV preparations are able to induce antibody against Slo and SpyCEP antigens.

Example 9—OMV-SpyCEP Immune Serum Inhibits SpyCEP Mediated Processing of IL-8

Sera obtained from mice immunized with PBS alone, empty OMVs, OMV-SpyCEP and OMV+SpyCEP were tested for their capacity to neutralize IL-8 proteolytic activity of SpyCEP. To perform this IL-8 inhibition assay, SpyCEP (0.1 µg/ml) and IL-8 (1 µg/ml) were incubated with pools of mice polyclonal serum from the 8 immunized mice for each group at five different dilutions (1:2.5, 1:5, 1:10, 1:20, and 1:40) at 37° C. for 2 hours in PBS, 0.5 mg/ml BSA. As controls, SpyCEP was incubated with buffer only, and sera without SpyCEP were used. The amount of uncleaved IL-8 was quantified after 2 h by ELISA (human IL-8 Immunoassay kit, Invitrogen) and expressed as a percentage of uncleaved IL-8 in the reaction (incubation with SpyCEP) compared with IL-8 in the control reaction (incubation with buffer only).

Figure 11:
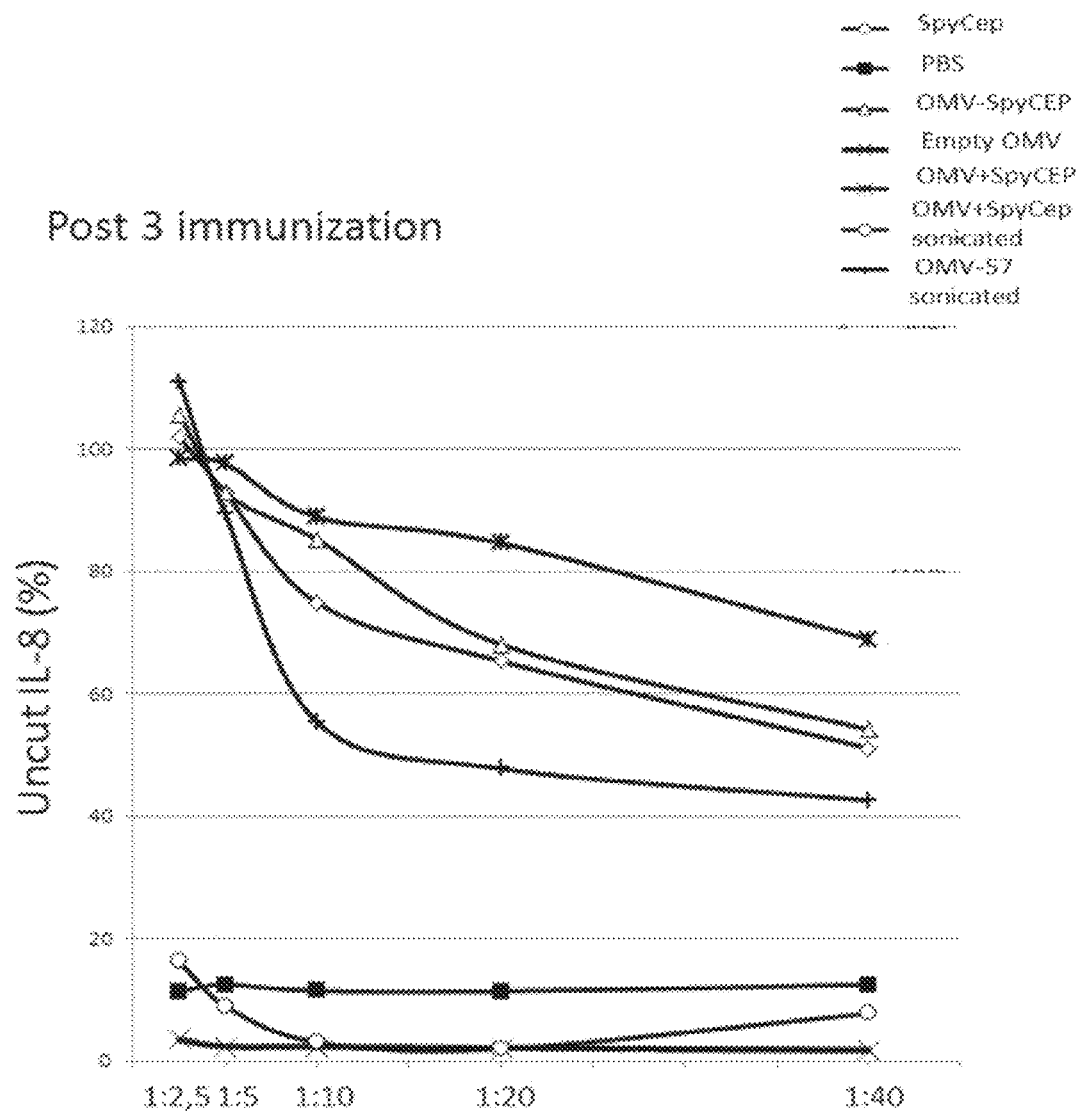
FIG. 11: shows the percentage amount of uncleaved IL-8 in the presence of 100 ng of recombinant SpyCEP and different dilutions of immune sera collected after 3 (post 3) immunization as determined by the ELISA assay.
Figure 12A:
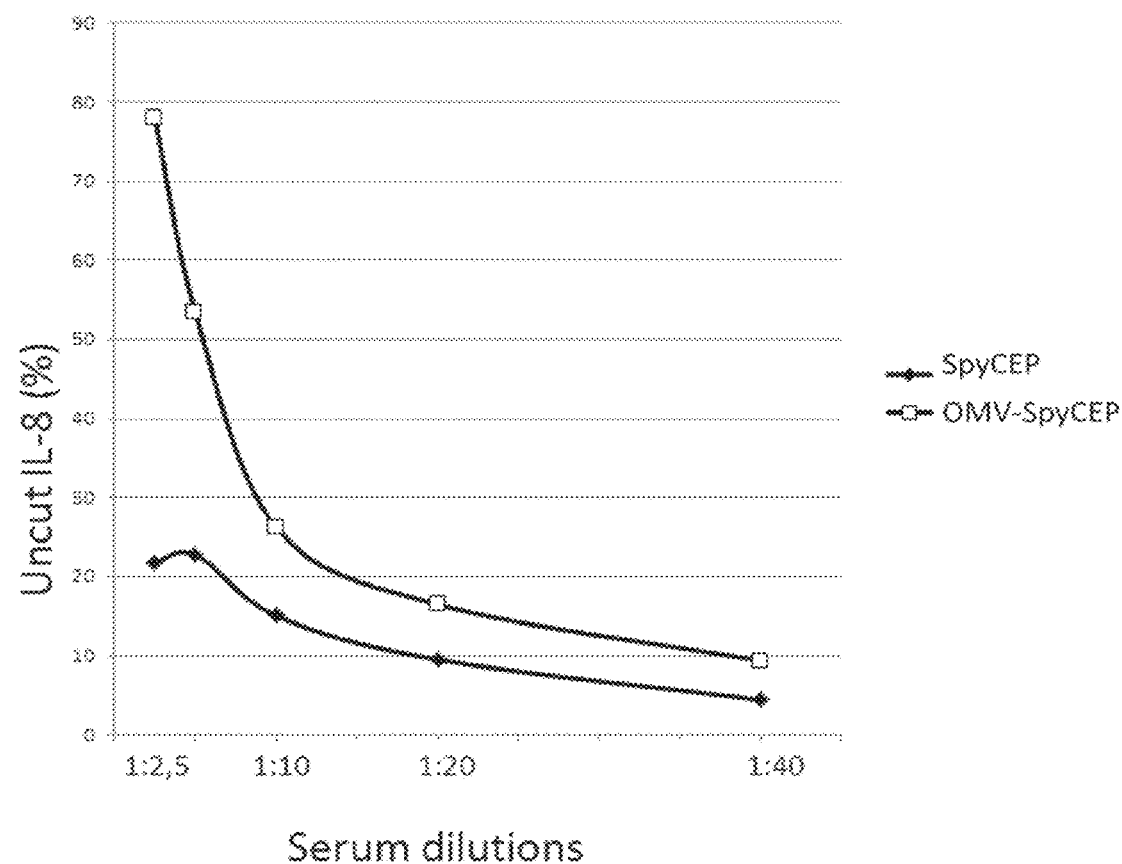
FIG. 12A: shows the percentage amount of uncleaved IL-8 in the presence of 100 ng of recombinant SpyCEP and different dilutions of immune sera collected after 2 (post 2) immunization as determined by the ELISA assay.
Figure 12B:
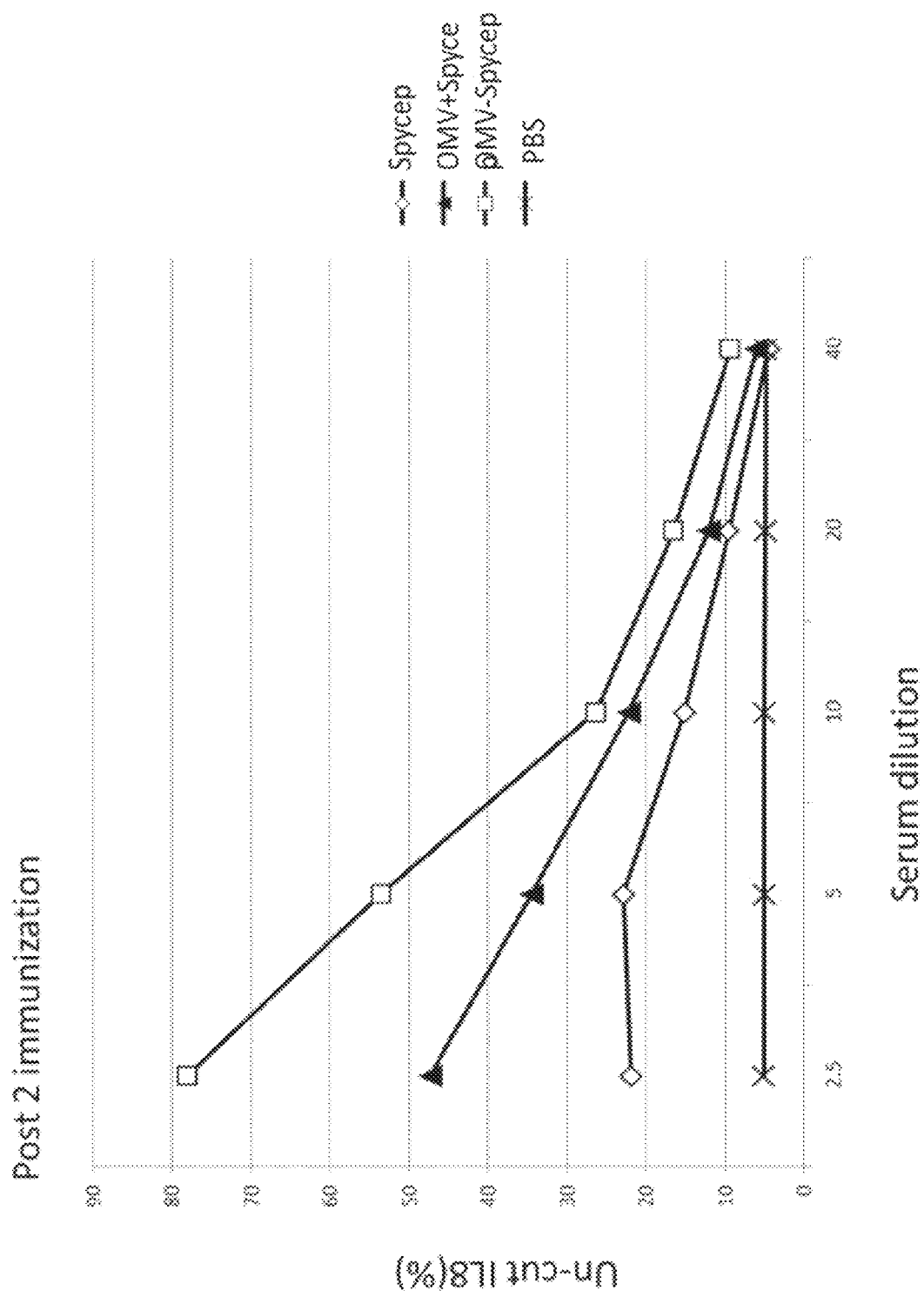
FIG. 12B: shows the percentage amount of uncleaved IL-8 in the presence of recombinant SpyCEP or different dilutions of immune sera collected after 2 (post 2) immunization with SpyCep containing OMVs or empty OMV and SpyCep as determined by the ELISA assay. PBS was used as a negative control.

FIGS. 11, 12A and 12B show the percent of uncleaved IL-8 in the presence of 100 ng of recombinant SpyCEP and different dilutions of immune sera collected after 3 (post 3) and 2 (post 2) immunizations, respectively, as determined by the ELISA assay.

Sera from mice immunized with recombinant SpyCEP, as positive control, and with engineered OMVs containing SpyCEP (OMV-SpyCEP) were able to neutralize SpyCEP proteolytic activity in a dose-dependent manner and gave statistically equivalent results.

Example 10—OMV-Slo Immune Serum Inhibits Slo Mediated Haemolysis

Sera obtained from mice immunized with PBS alone, empty OMVs, OMV-Slo, 20 µg Slo and 0.5 µg Slo (corresponding approximately to the amount of Slo contained in 20 µg OMVs) were tested for their capacity to neutralize the haemolysis activity of Slo. To perform this assay, Slo (60 ng) was incubated with pooled polyclonal serum from the 8 immunized mice for each group at six different dilutions (1:31.25; 1:63; 1:125; 1:250; 1:500 and 1:1000) for 20 minutes at room temperature in PBS, 0.5 mg/ml BSA. 1 ml of sheep blood was washed three times in PBS (with centrifugation at 3000×g), and the blood cells were finally suspended in 5 ml of PBS. 50 µl of this suspension was added to each of the samples and the samples were incubated at 37° C. for 30 min 60 ng Slo was used as a positive control to give 100% haemolysis, and PBS+BSA 0.5% was used as a negative control. Plates were then centrifuged for 5 min at 1,000×g, and the supernatant was transferred to 96-well flat-bottomed plates and the absorbance measured at 540 nm [128].

Figure 13:
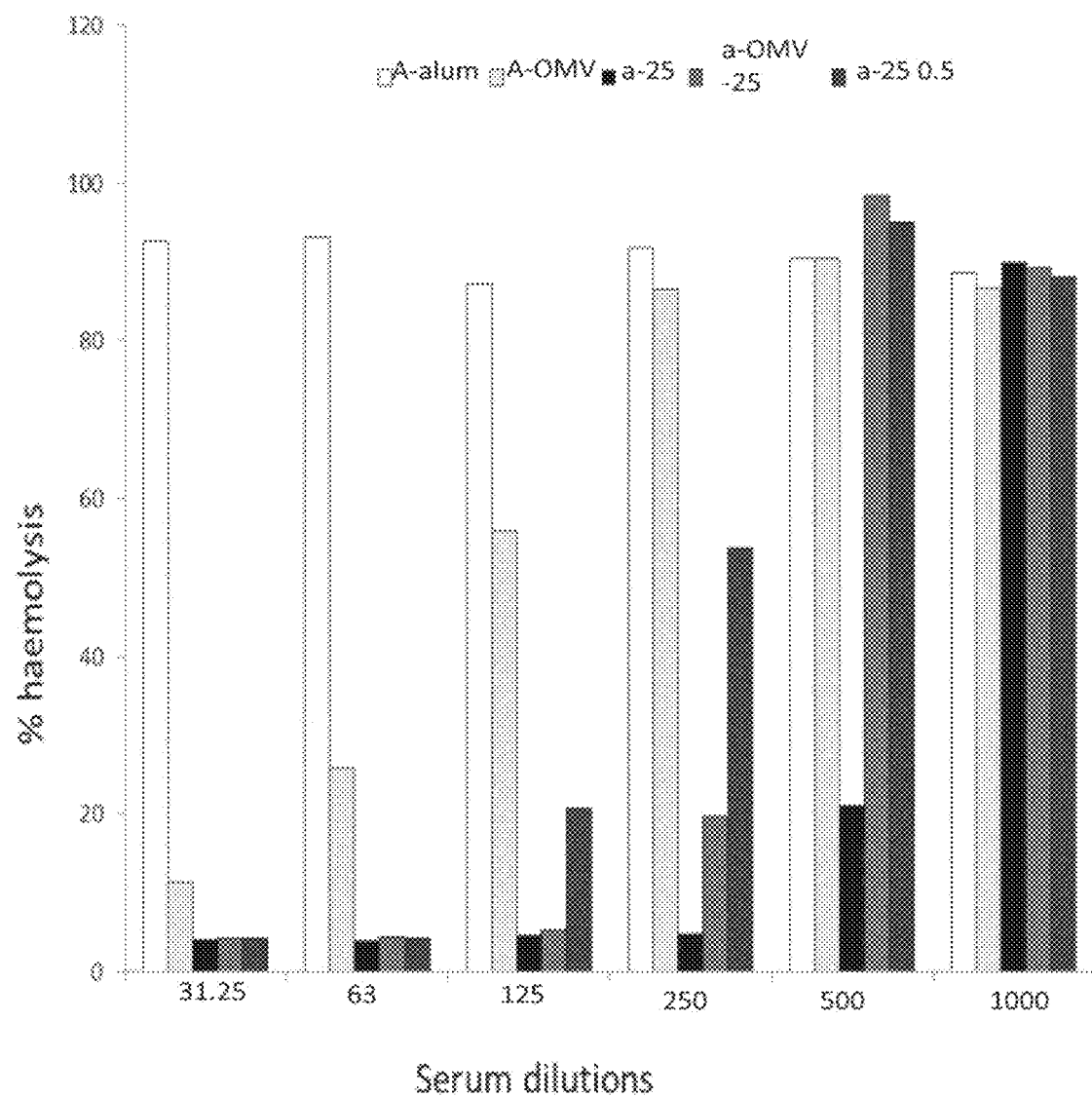
FIG. 13: shows the percentage amount of haemolysis in the presence of different dilutions of immune sera collected from mice immunized with recombinant Slo, as a positive control, or with engineered OMVs containing Slo (OMV-Slo).

FIG. 13 shows the percent of haemolysis provided by each sample at different sera dilutions. Sera from mice immunized with recombinant Slo, as positive control, and with engineered OMVs containing Slo (OMV-Slo) were able to neutralize the hemolytic activity of Slo in a dose-dependent manner and gave statistically equivalent results.

Example 11—OMVs Carrying Foreign Antigens in their Lumen Elicit Strong Protective Responses Having demonstrated that even if recombinant antigens are present in the lumen of OMVs immunization with such OMVs induce antigen-specific functional antibodies, we lastly asked the question whether immunization can also induce antigen-specific protective immunity. To test this, female CD1 5-week old mice were immunized intraperitoneally on days 0, 21 and 35 with a vaccine formulation including 25 µg of OMV carrying either Slo or SpyCEP formulated in alum hydroxide. As positive controls mice were also immunized with 25 µg OMVs carrying Slo and SpyCEP sonicated just before absorption to Alum Hydroxide, and with recombinant Slo, recombinant SpyCEP and recombinant M protein from M1 strain (20 µg each), all formulated in Alum Hydroxide. Three weeks after the third immunization, mice were infected intraperitoneally with 200 µl of a bacterial suspension containing about 2.5E+06 CFU of M1 3348 strain. Mice were monitored on a daily basis for 6 days after treatment and euthanized when they exhibited defined humane endpoints that had been pre-established for the study in agreement with Novartis Animal Welfare Policies.

Figure 14:
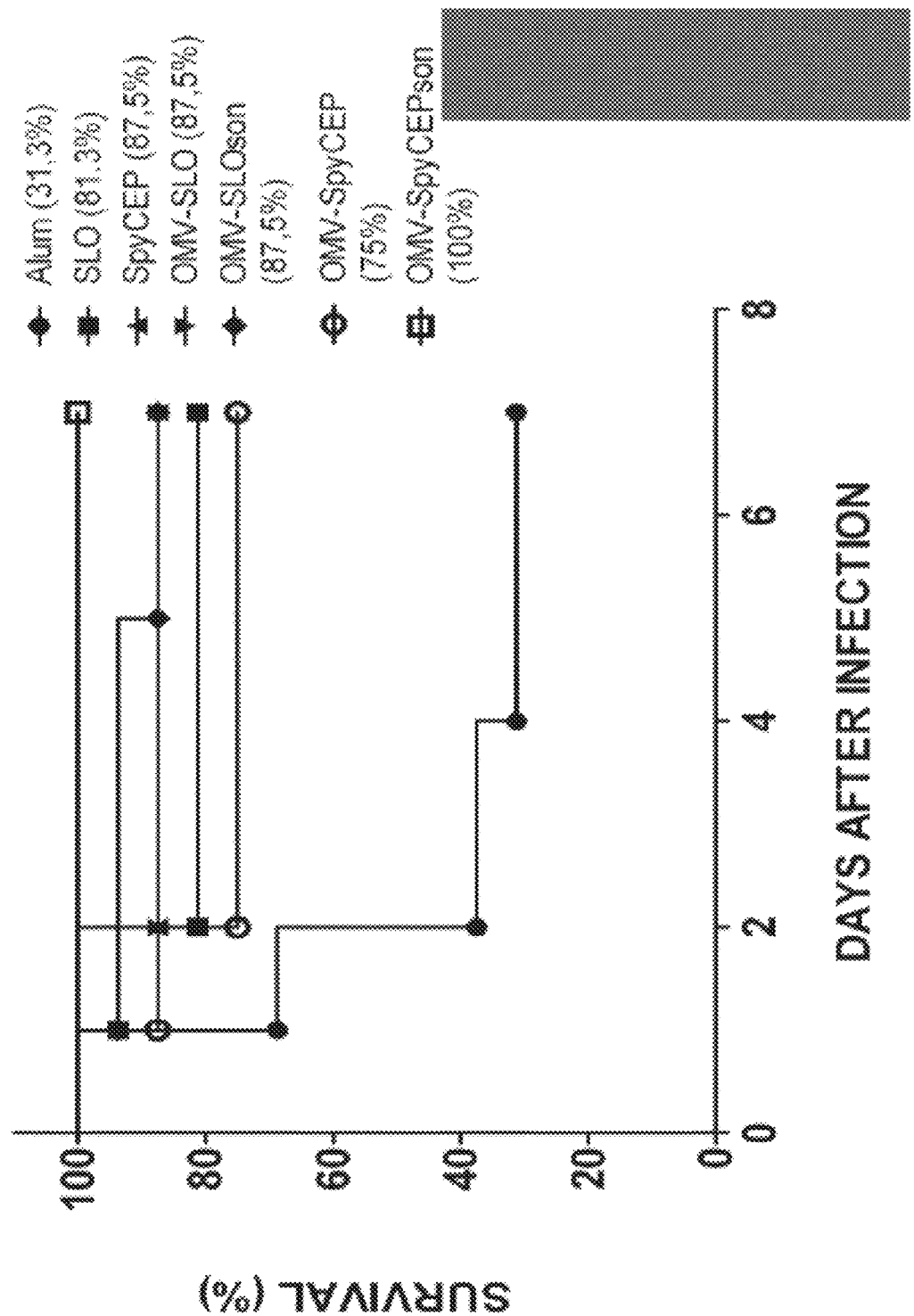
FIG. 14: shows a survival plot of samples of 8 mice immunized with OMVs carrying Slo and SpyCEP, with or without sonication before adsorption to Alum. The survival plots of mice immunized with recombinant Slo and SpyCEP adsorbed to Alum are used as a control.

As shown in the FIG. 14, which reports data from experiments in which 8 mice per group were used, OMVs carrying Slo and SpyCEP gave a protection of 87.5% and 75%, respectively, if not sonicated, very comparable with the 87.5% and 100% protection values obtained if OMVs were sonicated before absorption to Alum and immunization. This protection also similar to what obtained with recombinant Slo and SpyCEP (81.3% and 87.5% respectively) absorbed to Alum, a remarkable result considering that the recombinant OMVs carry approximately 0.2-0.4 µg of Slo and SpyCEP approximately 100-fold less than what has been used for the immunization with recombinant Slo and SpyCEP.

Figure 15A:
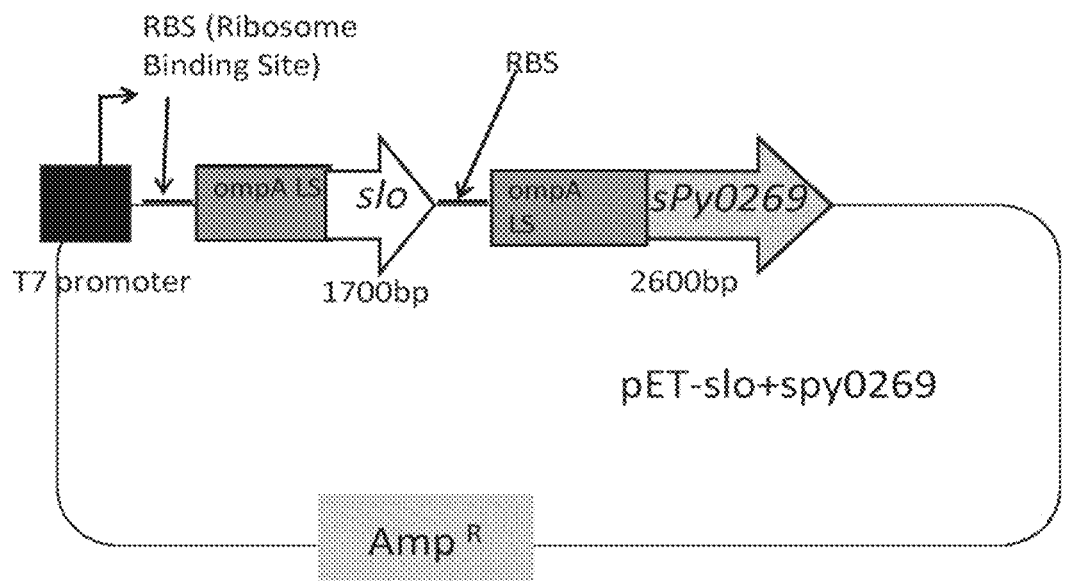
FIG. 15A: shows a map of the pET-slo+spy0269 plasmid.

Example 12—Generation of a Bi-Cistronic Construct for Expression of Spy0269 and Slo-Dm, and a Tri-Cistronic Construct for Expression of Spy0269, Slo and SpyCEP, in the OMV Lumen To generate the bi-cistronic construct, slo-dm and spy0269 genes were amplified from pET-21_slo and pET-21_spy0269 using slo-fus-F/slo-fus-R3 and Spy0269-fus3/Spy0269-R primers respectively. Generated fragments were phopshorylated, ligated and cloned into a pET-OmpA plasmid using the PIPE cloning method [123] generating a pET-slo+spy0269 plasmid (SEQ ID:38) (FIG. 15A).

The Slo-dm and Spy0269 proteins were cloned into the pET-OmpA plasmid under the same T7 promoter, to generate a bi-cistronic construct. An OmpA leader sequence was cloned upstream of each gene, so that its expression was directed to the lumen of the OMVs that were subsequently produced (see below).

Figure 15B:
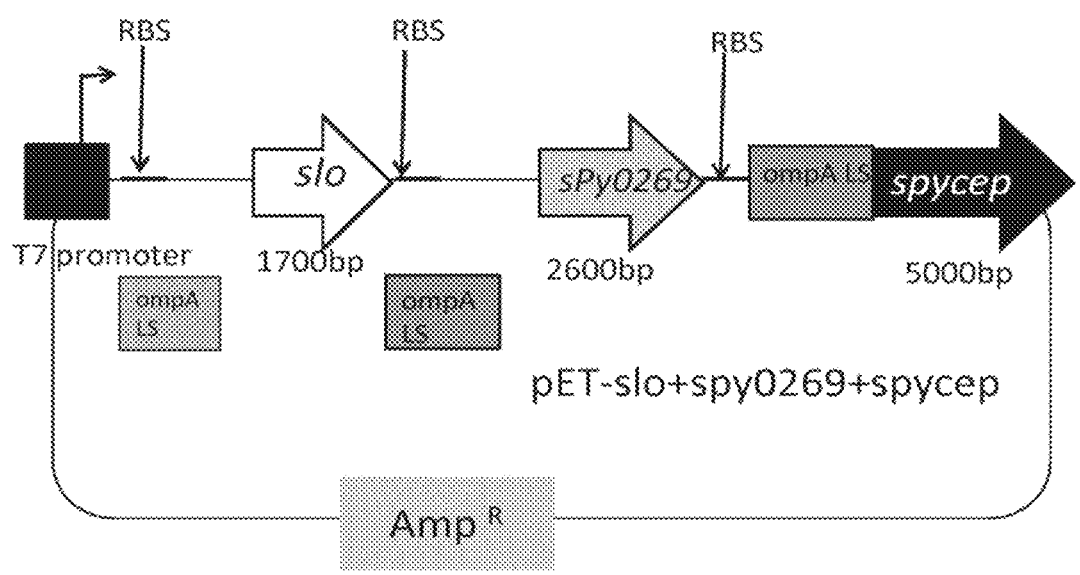
FIG. 15B FIG. 15B: shows a map of the pET-slo+spy0269+spycep plasmid.

To generate the tri-cistronic construct, the pET-spy0269+slo plasmid was amplified with nohisflag/Spy0269-fus-R primers and spycep gene was amplified from pET-21 spycep plasmid using spycep-fus-F/spycep-R3 primers and cloned into the plasmid using the PIPE cloning method. Generated fragments were phopshorylated, ligated and cloned into pET-OmpA plasmid using the PIPE cloning method [123] generating pET-slo+spy0269+spycep plasmid (FIG. 15B).

Figure 16A:
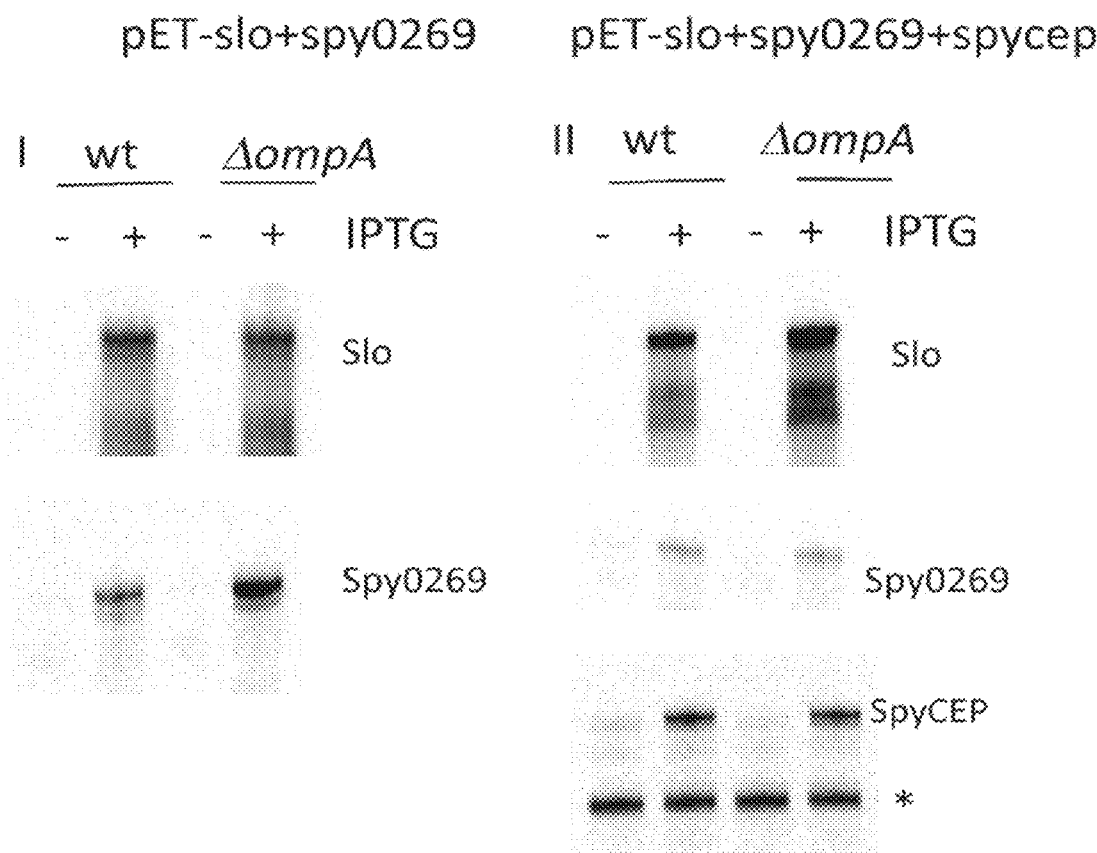
FIG. 16A FIG. 16A: shows Western blots showing that all of the proteins are expressed from the bi-cistronic and the tri-cistronic constructs after induction with IPTG.

The resulting plasmids were transformed into ΔompA and wild type E. coli BL21 mutant strains for protein induction and OMV preparation. Expression of the cloned genes was induced by adding 1 mM IPTG to the cultures. Western blots were performed on total lysates to verify protein expression. FIG. 16A panel I and panel II shows that all of the cloned proteins from the bi-cistronic and the tri-cistronic construct are expressed after induction with IPTG.

Figure 16B:
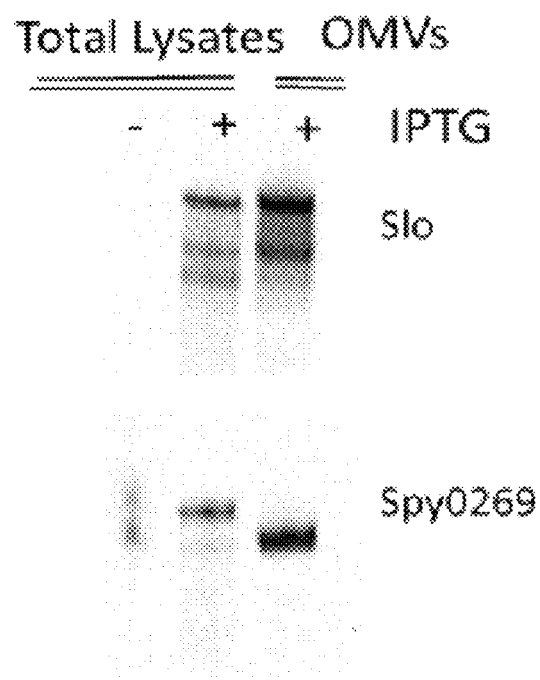
FIG. 16B: shows Western blots showing that both Slo and Spy0269 proteins are expressed and present into the OMVs.

OMVs were prepared, as described above, from the ΔompA and wild type strains containing the bi-cistronic construct. The Western blot results of FIG. 16B show that both Slo and Spy0269 proteins are expressed and present into the OMVs.

Variant sequences of spy0269 (GAS40) are provided in SEQ IDs:43 to 69. Variant sequences of spyCEP (GAS57) are provided in SEQ IDs:71 to 75 and a detoxified or enzymatically inactive mutant (GAS57 D151A-S617A) is provided in SEQ IDs:39 and 40. The slo (GAS25) W535F-P427L double mutant is provide in SEQ IDs:41 and 42.

REFERENCES

[1] WO2006/046143
[2] Berlanda Scorza et al. (2008) Mol Cell Proteomics 7:473-85
[3] European patent 0011243
[4] Fredriksen et al. (1991) NIPH Ann. 14(2):67-80
[5] WO2004/019977
[6] Hozbor et al. (1999) Curr Microbiol 38:273-8
[7] Tan et al. (2010) N Engl J Med 362(16):1511-20
[8] Collins, B S (2011) Discov Med 12(62):7-15
[9] WO 2010/010983
[10] Chen, D J et al. (2010) PNAS 107:3099-3104
[11] Ketsy, N C and Kuehn, M J (2004) J Biol Chem 279:2069-2076
[12] Katial et al. 2002, Infect Immun, 70: 702-707
[13] WO 02/09643
[14] Beveridge, 1999, J. Bacteriol. 181: 4725-4733
[15] Moe et al. 2002, Infect. Immun. 70:6021-6031
[16] Murakami et al. Oral Microbiol. Immunol. 2007, 22: 356-360
[17] Giuliani et al. (2006) Proc Natl Acad Sci USA 103(29): 10834-9.
[18] WO2009/016515.
[19] WO02/34771.
[20] WO2005/032582.
[21] WO2010/119343.
[22] WO2006/110413.
[23] WO2005/111066.
[24] WO2005/002619.
[25] WO2006/138004.
[26] WO2009/109860.
[27] WO02/02606.
[28] WO03/018054.
[29] WO2006/091517.
[30] WO2008/020330.
[31] WO2006/089264.
[32] WO2009/104092.
[33] WO2009/031043.

[34] WO2007/049155.
[35] Alberts et al., (2008) Molecular Biology of The Cell, 5th Ed, page 630
[36] M. Feldhahn et al (2008) Nucleic Acid Research 2008 Jul. 1; 36(Web Server issue): W519-22.
[37] Larsen et al (2006) Immunome Res 2:2
[38] Haste Andersen P, et al (2006) Protein Sci 15:2558-2567.
[39] Ponomarenko J V et al (2008). BMC Bioinformatics 9:514
[40] Broedel, Jr., S. E. and Papciak, S. M. (2007). ACES™ Signal Sequence and YebF Expression Systems. Athena Environmental Sciences, Inc., Technical Brief, December 2007, athenaes.com available under the directory osc/TechBrief_ACESSignalSeqUWeb.pdf
[41] Infect Immun. 72: 1914-1919, 2004
[42] Katial et al. 2002, Infect Immun, 70: 702-707
[43] WO 02/09643
[44] Beveridge, 1999, J. Bacteriol. 181: 4725-4733
[45] Moe et al. 2002, Infect. Immun 70:6021-6031
[46] WO2011/036562
[47] WO2004/019977
[48] European patent 0011243
[49] Fredriksen et al. (1991) NIPH Ann. 14(2):67-80
[50] WO01/91788
[51] WO2005/004908
[52] Gennaro (2000) Remington: The Science and Practice of Pharmacy. 20th edition, ISBN: 0683306472
[53] WO2006/110603
[54] WO90/14837
[55] Podda & Del Giudice (2003) Expert Rev Vaccines 2:197-203
[56] Podda (2001) Vaccine 19: 2673-2680
[57] Vaccine Design: The Subunit and Adjuvant Approach (eds. Powell & Newman) Plenum Press 1995 (ISBN 0-306-44867-X)
[58] Vaccine Adjuvants: Preparation Methods and Research Protocols (Volume 42 of Methods in Molecular Medicine series). ISBN: 1-59259-083-7. Ed. O'Hagan
[59] Allison & Byars (1992) Res Immunol 143:519-25
[60] Hariharan et al. (1995) Cancer Res 55:3486-9
[61] US-2007/014805
[62] WO95/11700
[63] U.S. Pat. No. 6,080,725
[64] WO2006/113373
[65] WO2005/097181
[66] U.S. Pat. No. 5,057,540
[67] WO96/33739
[68] EP-A-0109942
[69] WO96/11711
[70] WO00/07621
[71] Barr et al. (1998) Advanced Drug Delivery Reviews 32:247-271
[72] Sjolanderet et al. (1998) Advanced Drug Delivery Reviews 32:321-338
[73] EP-A-0689454
[74] Johnson et al. (1999) Bioorg Med Chem Lett 9:2273-2278
[75] Evans et al. (2003) Expert Rev Vaccines 2:219-229
[76] Meraldi et al. (2003) Vaccine 21:2485-2491
[77] Pajak et al. (2003) Vaccine 21:836-842
[78] Kandimalla et al. (2003) Nucleic Acids Research 31:2393-2400
[79] WO02/26757
[80] WO99/62923
[81] Krieg (2003) Nature Medicine 9:831-835
[82] McCluskie et al. (2002) FEMS Immunology and Medical Microbiology 32:179-185
[83] WO98/40100
[84] U.S. Pat. No. 6,207,646
[85] U.S. Pat. No. 6,239,116
[86] U.S. Pat. No. 6,429,199
[87] Kandimalla et al. (2003) Biochemical Society Transactions 31 (part 3):654-658
[88] Blackwell et al. (2003) J Immunol 170:4061-4068
[89] Krieg (2002) Trends Immunol 23:64-65
[90] WO01/95935
[91] Kandimalla et al. (2003) BBRC 306:948-953
[92] Bhagat et al. (2003) BBRC 300:853-861
[93] WO03/035836
[94] Schellack et al. (2006) Vaccine 24:5461-72
[95] Lingnau et al. (2007) Expert Rev Vaccines 6:741-6
[96] WO2004/084938
[97] WO95/17211
[98] WO98/42375
[99] Beignon et al. (2002) Infect Immun 70:3012-3019
[100] Pizza et al. (2001) Vaccine 19:2534-2541
[101] Pizza et al. (2000) Int J Med Microbiol 290:455-461
[102] Scharton-Kersten et al. (2000) Infect Immun 68:5306-5313
[103] Ryan et al. (1999) Infect Immun 67:6270-6280
[104] Partidos et al. (1999) Immunol Lett 67:209-216
[105] Peppoloni et al. (2003) Expert Rev Vaccines 2:285-293
[106] Pine et al. (2002) J Control Release 85:263-270
[107] Tebbey et al. (2000) Vaccine 18:2723-34
[108] Domenighini et al. (1995) Mol Microbiol 15:1165-1167
[109] WO99/40936
[110] WO99/44636
[111] Singh et all (2001) J Cont Release 70:267-276
[112] WO99/27960
[113] U.S. Pat. No. 6,090,406
[114] U.S. Pat. No. 5,916,588
[115] EP-A-0626169
[116] Stanley (2002) Clin Exp Dermatol 27:571-577
[117] Jones (2003) Curr Opin Investig Drugs 4:214-218
[118] WO99/11241
[119] WO94/00153
[120] WO98/57659
[121] European patent applications 0835318, 0735898 and 0761231
[122] Maxson, M. E., and Darwin, A. J. (2004) J. Bacteriol 186:4199-4208
[123] Klock H. E., Lesley S. A. (2009) Methods Mol Biol 498:91-103
[124] Deng, T., Noel, J. P., Tsai, M. D. (1990) Gene 93:229-234
[125] Findlay, H. E., McClafferty, H., Ashley, R. H. (2005) BMC Microbiology 5:5
[126] [126] Sambrook J, Fritch, E F and Maniatis, T (1989) Mol Cloning: A Laboratory Manual (Cold Spring Harbor Laboratory Press, Cold Spring Harbor, N.Y., ed. 2
[127] Edwards R J, Taylor G W, Ferguson M, Murray S, Rendell N, Wrigley A, Bai Z, Boyle J, Finney S J, Jones A, Russell H H, Turner C, Cohen J, Faulkner L, Sriskandan S (2005) J Infect Dis 192: 783-790
[128] Bensi et al., (2012) Mol. Cell Proteomics

The invention claimed is:

1. A composition comprising an outer membrane vesicle (OMV) from a gram-negative bacterium and a heterologous protein in the lumen thereof,
    wherein the heterologous protein is a soluble bacterial or viral protein; and
    wherein the composition is capable of eliciting an immune response to the heterologous protein when administered to a mammal.

2. The composition of claim 1, wherein the heterologous protein is functionally active in the lumen of the OMV.

3. The composition of claim 1, wherein the immune response is an antibody response.

4. A method for preparing the composition of claim 1, the method comprising the step of
    expressing the heterologous protein in the periplasm of the gram-negative bacterium.

5. The method according to claim 4, comprising expressing the heterologous protein in the periplasm of the gram-negative bacterium from an expression vector comprising a nucleic acid sequence encoding the heterologous protein operatively linked to a nucleic acid encoding a signal sequence of a periplasmic protein.

6. The method according to claim 5, wherein the heterologous protein does not include a native signal sequence.

7. The method of claim 4, further comprising the step of isolating the OMV.

8. The composition of claim 1, wherein the gram-negative bacterium is selected from the group consisting of E. coli, N. meningitidis, Salmonella sp., and Shigella sp.

9. The composition of claim 1, wherein the gram-negative bacterium is a hyperblebbing strain of the gram-negative bacterium.

10. The composition of claim 9, wherein the gram-negative bacterium is a ΔtolR E. coli strain or a ΔompA E. coli strain.

11. The composition of claim 1, wherein the heterologous protein is an antigen.

12. The composition of claim 1, wherein the heterologous protein is a cytoplasmic protein or a periplasmic protein in the heterologous organism.

13. The composition of claim 1, wherein the heterologous protein is a membrane-associated protein comprising a membrane anchor in the heterologous organism wherein the membrane anchor is deleted.

14. A pharmaceutical composition comprising (a) the composition of claim 1, and (b) a pharmaceutically acceptable carrier.

15. The pharmaceutical composition according to claim 14, wherein the pharmaceutical composition is a vaccine.

16. A method of generating an immune response to a heterologous protein in a mammal, the method comprising a step of:
    administering the vaccine of claim 15 to the mammal in an amount effective to elicit an immune response to the heterologous protein.

* * * * *